(12) United States Patent
Kozubal et al.

(10) Patent No.: US 9,796,989 B2
(45) Date of Patent: Oct. 24, 2017

(54) ACIDOPHILIC FUSARIUM OXYSPORUM STRAINS, METHODS OF THEIR PRODUCTION AND METHODS OF THEIR USE

(71) Applicant: SUSTAINABLE BIOPRODUCTS HOLDINGS, LLC, Chicago, IL (US)

(72) Inventors: Mark A. Kozubal, Bozeman, MT (US); Richard E. Macur, Manhattan, MT (US); William P. Inskeep, Bozeman, MT (US)

(73) Assignee: SUSTAINABLE BIOPRODUCTS HOLDINGS, LLC, Chicago, IL (US)

( * ) Notice: Subject to any disclaimer, the term of this patent is extended or adjusted under 35 U.S.C. 154(b) by 0 days.

(21) Appl. No.: 14/790,948

(22) Filed: Jul. 2, 2015

(65) Prior Publication Data

US 2016/0002680 A1 Jan. 7, 2016

Related U.S. Application Data

(60) Provisional application No. 62/020,607, filed on Jul. 3, 2014, provisional application No. 62/061,076, filed on Oct. 7, 2014.

(51) Int. Cl.

| | | |
|---|---|---|
| *C12R 1/77* | (2006.01) | |
| *C12P 7/64* | (2006.01) | |
| *C12P 7/06* | (2006.01) | |
| *C12P 3/00* | (2006.01) | |
| *C12P 7/10* | (2006.01) | |

(52) U.S. Cl.
CPC ............. *C12P 7/649* (2013.01); *C12P 3/00* (2013.01); *C12P 7/065* (2013.01); *C12P 7/10* (2013.01); *C12P 7/6463* (2013.01); *C12P 2203/00* (2013.01); *Y02E 50/13* (2013.01); *Y02E 50/16* (2013.01); *Y02E 50/17* (2013.01)

(58) Field of Classification Search
CPC ...................................................... C12R 1/77
See application file for complete search history.

(56) References Cited

U.S. PATENT DOCUMENTS 5,258,293 A * 11/1993 Lynd .......................... C12P 7/10
                                                        435/161
2012/0052536 A1    3/2012 Medoff et al.

FOREIGN PATENT DOCUMENTS

WO       2010042842 A2     4/2010

OTHER PUBLICATIONS

Naim et al., Argricultural Wastes 14 (1985) 207-220, "Production of Lipids and Sterols by Fusarium oxysporum (Schlecht). Utilization of Some Agro-Industrial By-Products as Additives and Basal Medium".*
Kozubal, M. et al., "Isolation and Distribution of a Novel Iron-Oxidizing Crenarchaeon from Acidic Geothermal Springs in Yellowstone National Park", Appl. Environ. Microbiol., 2008, pp. 942-949, vol. 74.
Fisher et al., "Taxonomic importance of microconidial chains in Fusarium section Liseola and effects of water potential on their formation", Mycologia, 1983, pp. 693-698, vol. 75.
Klotz et al., "A medium for enhancement of chlamydospore formation in Fusarium species", Mycologia, 1988, pp. 108-109, vol. 80.
Nelson et al., "Taxonomy, Biology, and Clinical Aspects of Fusarium Species", Clinical Microbiology Reviews, 1994, pp. 479-504, vol. 7., No. 4.
Klinke et al., "Inhibition of ethanol-producing yeast and bacteria by degradation products produced during pre-treatment of biomass.", 2004, Appl Microbiol Biotechnol, pp. 10-26, vol. 66.
Hendricks et al., "Pretreatments to enhance the digestibility of lignocellulosic biomass.", 2009, Bioresource Technology, pp. 10-18, vol. 100.
Moran, M., "Biofuel Production Using an Acidophilic Fungus," MSU Student Research Celebration, Mar. 5, 2013,. Retrieved from the Internet<http://scholarworks.montana.edu/xmlui/handle/1/500> on Oct. 5, 2015.
Jannotia, S., "MSU graduate launches biofuels start-up, partners with university," MSU News Service, Feb. 15, 2013. Retrieved from the Internet<http://www.montana.edu/news/11756/msu-graduate-launches-blofuels-start-up-partners-with-university> on Oct. 5, 2015.
International Search Report, PCT application No. PCT/US2015/039100, dated Oct. 30, 2015, 4 pages.
Akpinar-Bayizit, A. et al., Single cell oil (SCO) production by *Fusarium* species using cheese whey as a substrate. Mljekarstvo 2014, 64 (2), pp. 111-118.
Bhatia, Iqbal et al., "Effect of Different Cultural Conditions on the Chemical Composition of Lipids of Fusarium oxysporumn", J. Sci. Fd Agric., 1978, 29, 611-618.
Merrill et al. "Lipids and Lipid-Like Compounds of Fusarium", Lipids of Pathogenic Fungi, 1996, pp. 200-217, CRC Press.

\* cited by examiner

*Primary Examiner* — Ruth Davis
(74) *Attorney, Agent, or Firm* — Gorman IP Law, APC

(57) ABSTRACT

The present invention provides isolated acidophilic *Fusarium oxysporum* strains, such as MK7, and their progeny, compositions comprising such strains and their progeny, methods of producing such strains and their progeny, and methods of using such strains and their progeny.

20 Claims, 7 Drawing Sheets

A

B

SEQUENCE LISTING

```
<160> NUMBER OF SEQ ID NOS: 1

<210> SEQ ID NO 1
<211> LENGTH: 962
<212> TYPE: DNA
<213> ORGANISM: Fusarium oxysporum strain MK7

<400> SEQUENCE: 1 ccgcgggaa  tactacctga  tccgaggtca  cattcagagt  tgggggttta  cggcttggcc      60
gcgccgcgta  ccagttgcga  gggttttact  actacgcaat  ggaagctgca  gcgagaccgc     120
cactagattt  cggggccggc  ttgccgcaag  ggctcgccga  tccccaacac  caaacccggg     180
ggcttgaggg  ttgaaatgac  gctcgaacag  gcatgcccgc  cagaatactg  gcgggcgcaa     240
tgtgcgttca  aagattcgat  gattcactga  attctgcaat  tcacattact  tatcgcattt     300
```

```
tgctgcgttc ttcatcgatg ccagaaccaa gagatccgtt gttgaaagtt ttgatttatt      360
tatggtttta ctcagaagtt acatatagaa acagagttta ggggtcctct ggcgggccgt      420
cccgttttac cgggagcggg ctgatccgcc gaggcaacaa ttggtatgtt cacaggggtt      480
tgggagttgt aaactcggta atgatccctc cgcagttctc acctacggat aggatcatta      540
ccgagtttac aactcccaaa cccctgtgaa catacccatt gttgcctcgg ccggatcagc      600
ccgctcccgg ttaaaacggg acggcccgcc agagtacccc taaactctgt ttctatatgt      660
aacttctgag taaaaccata aataaatcaa aactttcaac acgcatctct tgcttctgtc      720
atcgatgaag aacgcagcaa aatgcgatag tcatgtgatt gcacattcag tgaatcatcg      780
atcttgacgc acattgcgcc tgcagtattc tggcggtcat gcctgttcga gcgtcattca      840
gccctcagcc ctcggttgtg ttcgggatcg gcgagtcctg cgccagcgac cggatcagtg      900
gcgtctgcct gcgcctccat tgcggttaga gttaagccct cgcccacttg ttttacgcta      960
ac                                                                    962
```

ACIDOPHILIC FUSARIUM OXYSPORUM STRAINS, METHODS OF THEIR PRODUCTION AND METHODS OF THEIR USE

CROSS-REFERENCE TO RELATED APPLICATIONS

This application claims the benefit of U.S. provisional application No. 62/020,607, filed on Jul. 3, 2014, and U.S. provisional application 62/061,076, filed on Oct. 7, 2014, each of which is hereby incorporated by reference in its entirety for all purposes.

DESCRIPTION OF THE TEXT FILE SUBMITTED ELECTRONICALLY

The contents of the text file submitted electronically herewith are incorporated herein by reference in their entirety; A computer readable format copy of the Sequence Listing (filename: MONT_151_03US_ST25.txt, date recorded: Jul. 1, 2015, file size 2 kilobytes).

TECHNICAL FIELD

This application relates to novel isolated fungal strains of acidophilic *Fusarium oxysporum*, (e.g., MK7), their progeny, methods of producing such isolated fungal strains and their progeny, and methods of using such isolated fungal strains and their progeny to produce useful processes and products. For example, the isolated fungal strains and their progeny are useful for converting ligno-cellulosic feedstocks, algal biomass, and glycerol into energy-rich metabolites for bioenergy, for producing enzymes, antibiotics, specifically fatty acids and lipids (e.g. waxes) for commercial applications, dewaxing straw and for neutralizing acid and binding heavy metals.

BACKGROUND

*Fusarium* (synonyms: *Fusisporium*, *Pseudofusarium*, *Sporotrichella*) is a large genus of filamentous fungi widely distributed in soil and in association with plants. Most species are harmless saprobes and are relatively abundant members of the soil microbial community. Some species produce mycotoxins in cereal crops that can affect human and animal health if they enter the food chain. The main toxins produced by these *Fusarium* species are fumonisins and trichothecenes.

*Fusarium* strains isolated from nature have proven useful to mankind in a wide variety of technologies, including for use as food and for the production of antibiotics. The need still exists for new isolates of *Fusarium* for use in new and existing applications. The present invention provides a unique isolated strain of *Fusarium* and its progeny which are useful for a number of different purposes, including but not limited to bioenergy production, as biolubricants, for biorecovery of precious metals by biosorption, for remediation of mine waste, for dewaxing of wheat straw, for degradation of algal biomass, and glycerol containing waste products, and for antibiotic, siderphore, and plasticizer production.

SUMMARY

The present invention provides isolated fungal strains of acidophilic *Fusarium oxysporum*, such as the isolated strain designated as MK7, which has been deposited as ATCC Deposit No. PTA-10698, and/or its progeny. "Progeny" as used herein refers to any and all descendants by lineage which originate from the isolated strain no matter however or wherever produced. Included within the definition of "progeny" as used herein are any and all mutants of the isolated/deposited strain and its progeny, wherein such mutants have all of the physiological and morphological characteristics of the isolated/deposited strain and its progeny.

In one embodiment, the present invention provides an isolated ligno-cellulose degrading acidophilic fungal strain of *Fusarium oxysporum* or its progeny, wherein the isolated fungal strain of *Fusarium oxysporum* has at least the following identifying characteristics:
  a) the isolated strain is acidophilic and can grow at a pH ranging from about 0.7 to about 7.5; and
  b) ability to produce lipids from ligno-cellulosic feedstocks, carbon containing waste products, carbohydrates, or a combination thereof under aerobic or substantially aerobic conditions;

In one embodiment, the isolated strain of the present invention further comprises one or more the following additional identifying characteristics:
  c) ability to produce ethanol and/or hydrogen from ligno-cellulosic feedstocks, carbon containing waste products, carbohydrates, or a combination thereof under anaerobic or substantially anaerobic conditions;
  d) ability to tolerate Mn concentrations of up to 25 mM, As concentrations up to 250 mM or 300 mM, and Hg concentrations of up to 100 mM;
  e) ability to dewax wheat straw and other plant material;
  f) ability to produce lipids from algal feedstocks and from waste generated during biofuel production (e.g. processed algal biomass, glycerol) under aerobic or substantially aerobic conditions;
  g) ability to produce ethanol and/or hydrogen from algal feedstocks and from waste generated during biofuel production (e.g. processed algal biomass, glycerol) under anaerobic or substantially anaerobic conditions;
  h) ability to produce Diisooctyl phthalate (DIOP);
  i) ability to produce Hexanedioic acid, mono(2-ethylhexyl) ester; and
  j) comprising an 18S rRNA and ITS region DNA sequence that shares at least 98% identity to SEQ ID NO. 1.

In some embodiments, the ligno-cellulosic feedstocks utilized by the isolated strain and its progeny are selected from the group consisting of agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), ligno-cellulosic containing waste (e.g., newsprint, waste paper, brewing grains, used rubber tire (UTR), municipal organic waste, yard waste, clinical organic waste, and waste generated during the production of biofuels (e.g. processed algal biomass, glycerol), and combination thereof. In some embodiments, the carbohydrates are selected from the group consisting of monosaccharides, disaccharides, oligosaccharides, polysaccharides, and mixture thereof.

In some embodiments, the said isolated fungal strain and its progeny can grow and/or multiply at a pH ranging from about 0.7 to about 7.0. For example, the strains and progeny of the instant invention are able to grown and/or multiply at a pH of at least about 7.0, at least about 6.5, at least about 6.0, at least about 5.5, at least about 5.0, at least about 4.5, at least about 4.0, at least about 3.5, at least about 3.0, at least about 2.5, at least about 2.0, at least about 1.9, at least about 1.8, at least about 1.6, at least about 1.4, at least about 1.2, at least about 1.0, at least about 0.9, at least about 0.8, at least about 0.75, at least about 0.7, at least about 0.65, at least about 0.6, or at least about 0.55.

In some embodiments, the isolated fungal strain and its progeny are resistant to high concentrations of other metals selected from the group consisting Ag, Zn, Fe, Al, Be, Pb, Cu, Cr, Ni, Cd, Co, Ni, Pd, Pt, U, Th, Mo, Sn, Ti, As, Au, Se, Sb and Hg.

The isolated *Fusarium oxysporum* strain and its progeny of the present invention can be cultured in the absence of antibiotics with little or no contamination by other organisms, wherein said other organisms can be selected from the group consisting of other bacterial strains, genus or species, other fungi (e.g., yeasts, molds), algae, viruses, plants, insects, and any combination thereof.

The present invention also provides a biologically pure culture having one or more of the identifying characteristics of the isolated fungal strain of *Fusarium oxysporum* or its progeny as described herein. In one embodiment, the biologically pure culture comprises the isolated fungal strain of *Fusarium oxysporum*, designated as MK7, which has been deposited as ATCC Deposit No. PTA-10698, and/or progeny thereof. In one embodiment, said isolated fungal strain and/or progeny thereof is in the form of conidia, pycnidia, chlamydospores, fragments of hyphae, or any and all combinations thereof.

The present invention further provides a composition comprising an isolated fungal strain of *Fusarium oxysporum* and/or its progeny having at least one or more of the identifying characteristics as described herein. In one embodiment, the isolated fungal strain is MK7 and/or the progeny thereof. In one embodiment, said compositions comprise the isolated fungal strain and/or progeny thereof in the form of conidia, pycnidia, chlamydospores, fragments of hyphae, or any and all combinations thereof. In some embodiments, the composition further comprises one or more components selected from the group consisting of a medium that supports growth of the fungal strain, an acidification material, a manganese donor, a nutrient addition, and any and all mixtures thereof. In one embodiment, the medium is a solid. In another embodiment, the medium is a liquid.

The present invention also provides methods of producing useful products using said isolated fungus stain and/or its progeny, comprising:

a) making a mixture of one or more said isolated fungal strains and/or its progeny with a feedstock material selected from the group consisting of ligno-cellulosic feedstocks, carbon containing agricultural and municipal waste products, carbohydrates, sugar monomers, yeast extract, casamino acids, and a combination thereof in a container, wherein the material can support the growth of said isolated fungal strain; and b) growing said isolated fungal strain in said mixture to produce one or more useful products.

In one embodiment, the mixture is under aerobic conditions or substantially aerobic conditions. In another embodiment, the mixture is under anaerobic conditions or substantially anaerobic conditions.

In one embodiment, said useful products are one or more energy-rich metabolites. For example, the useful products produced using the fungi and methods of the present invention include but are not limited to biofuels, and/or precursors of biofuels. In one embodiment, the mixture is under aerobic conditions or substantially aerobic conditions, and said energy-rich metabolites are essentially lipids, wherein the lipids can be extracted from the biomass of the isolated fungal strains and/or its progeny. In one embodiment, said lipids are essentially fatty acids. In one embodiment, said fatty acids are essentially unsaturated fatty acids and/or saturated fatty acids. In one embodiment, said unsaturated fatty acids are selected from the group consisting of oleic acid (18:1), α-linolenic acid (18:3), eicosenoic acid (20:1), and a combination thereof. In one embodiment, said saturated fatty acids are selected from the group consisting of palmitic acids (16:0), stearic acids (18:0), arachidic acid (20:0), behenic acid (22:0), and any and all combinations thereof. In one embodiment, the mixture is under anaerobic conditions or substantially anaerobic conditions, and said energy-rich metabolites are essentially alcohols, and/or hydrogen. In some embodiments, said alcohol is ethanol, butanol and/or isobutanol.

In one embodiment, said useful products are naphthazarinoid pigments. In a further embodiment, said naphthazarinoid pigments are harvested and used to produce pesticides selected from the group consisting of antibiotics, fungicides, herbicides, yeasticides, and insecticides.

In one embodiment, said useful products are siderophores.

In one embodiment, said useful products are plasticizers, e.g., Diisooctyl phthalate (DIOP, CAS 117-81-7) and/or Hexanedioic acid, mono(2-ethylhexyl) ester (or 2-Ethylhexyl hydrogen adipate, CAS 4337-65-9).

Compared to the methods previously known in the art, the present invention is unique at least in that the production process as described herewith is very simple in execution, whereby feedstocks are converted directly into lipids at high yield under acidic condition. In one embodiment, lignocellulosic feedstocks are selected from the group consisting of agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), lignocellulosic containing waste (e.g., newsprint, waste paper, brewing grains, used rubber tire (UTR), municipal organic waste, yard waste, clinical organic waste, and waste generated during the production of biofuels (e.g. processed algal biomass, glycerol), or any and all combinations thereof. In one embodiment, said carbohydrates are selected from the group consisting of monosaccharides, disaccharides, oligosaccharides, polysaccharides, and a combination thereof.

In one embodiment, said sugar monomers are selected from the group consisting of trioses, tetroses, pentoses, hexoses, heptoses, et al., and any and all combinations thereof. In one embodiment, said pentoses are selected from the group consisting of ribulose, xylulose, ribose, arabinose, xylose, lyxose, deoxyribose, and any and all combinations thereof. In one embodiment, said hexoses are selected from the group consisting of allose, altrose, glucose, mannose, glucose, idose, galactose, talose, psicose, fructose, sorbose, tagatose, and any and all combinations thereof.

In one embodiment, said mixture further comprises at least one component selected from the group consisting of acidification materials, manganese donors, nutrient additions, pH buffering materials, and any and all combinations thereof.

In some embodiments, said mixture has an initial pH from about 0.5 to about 3.0. In other embodiments, said mixture has an initial pH from about 3.0 to about 7.0. The pH is determined based on the products. For example, high lipid production takes place over a the pH range 2.0-7.0, ethanol production takes place between pH 3-4.5 and $H_2$ production takes place over a range of 2.0-7.0.

The present invention also provides methods of producing biofuel or precursor of biofuel using one or more said isolated fungus stains and/or the progeny thereof, said methods comprising:

a) making a mixture of one or more said isolated fungal strains and/or its progeny with a feedstock material selected from the group consisting of ligno-cellulosic feedstocks, carbon containing waste products, carbohydrates, sugar monomers, and any and all combinations thereof in a container, wherein the material can support the growth of said isolated fungal strains;

b) growing said isolated fungal strain in said mixture to produce one or more types of energy-rich metabolites as biofuel and/or precursors of biofuel;

c) harvesting said energy-rich metabolites; and d) optionally, producing biofuel from said biofuel precursors.

In one embodiment, said biofuel is biodiesel. In another embodiment, said biofuel is bioalcohols. In still another embodiment, said biofuel is biogas.

The present invention also provides methods of pretreating cellulosic waste and simultaneous conversion to energy-rich metabolites using one or more isolated fungus stains and/or its progeny thereof, said methods comprising:

a) making a mixture of one or more said isolated fungal strains and/or its progeny with cellulosic waste in a container; and b) growing said isolated fungal strain and/or its progeny in said mixture, wherein the cellulosic waste is degenerated and energy-rich metabolites are simultaneously produced.

In one embodiment, the cellulosic waste can support the growth of said isolated fungal strains and/or its progeny. In another embodiment, additional compounds that are necessary for the growth of said isolated fungal strains and/or its progeny are also added into the mixture, wherein the additional compounds are not provided by the cellulosic waste. Such compounds include, but are not limited to, macronutrients, micronutrients, and combination thereof. In still another embodiment, compounds that can facilitate the pretreatment can be also added into the mixture. Such compounds include, but are not limited to acidification materials, manganese donors, nutrients, pH buffering materials.

The present invention also provides methods of detoxifying fluid waste containing metals and/or recovering metals from said fluid waste through biosorption using one or more said isolated fungus stains and/or its progeny thereof, comprising making a mixture of one or more said isolated fungal strains and/or its progeny with the waste material containing one or more types of precious metals, wherein the fluid waste is detoxified and/or the metals are recovered through biosorption.

In one embodiment, the fluid waste can support the growth of said isolated fungal strains and/or its progeny. In another embodiment, additional compounds that are necessary for the growth of said isolated fungal strains and/or its progeny are also added into the mixture, wherein the additional compounds are not provided by the fluid waste. Such compounds include, but are not limited to, macronutrients, micronutrients, and combination thereof. In one embodiment, the biosorption is through siderophores produced in the isolated fungal strain. In one embodiment, the waste material is mining or industrial effluents. In one embodiment, the metal is selected from the group consisting of Mn, Ag, Zn, Fe, Al, Be, Pb, Cu, Cr, Ni, Cd, Co, Ni, Pd, Pt, U, Th, Mo, Sn, Ti, As, Au, Hg and any and all combinations thereof. The total concentration of the metal ion(s), or the concentration of a certain metal ion in the fluid is at least 0.1 ppm, 1 ppm, or 10 ppm, or 100 ppm, or 1000 ppm, or 10000 ppm, or 10000 ppm, or 100000 ppm, by weight. For example, the concentration of a certain metal ion in the fluid is higher than the requirement in the Federal Hazard Waste Codes EPA D004-EPA D013.

The present invention also provides methods of neutralizing pH of acidic fluids using one or more said isolated fungus stains and/or its progeny thereof, comprising making a mixture of one or more said isolated fungal strains with the acidic fluid, wherein the pH of the acidic fluids is neutralized. In one embodiment, the acidic fluid is acid mine drainage. In one embodiment, the acidic fluids can support the growth of said isolated fungal strains and/or its progeny. In another embodiment, additional compounds that are necessary for the growth of said isolated fungal strains and/or its progeny are also added into the mixture, wherein the additional compounds are not provided by the acidic fluids. Such compounds include, but are not limited to, carbon containing feedstocks, macronutrients, micronutrients, and any and all combinations thereof.

The present invention also provides acid-tolerant enzymes or portions of the acid-tolerant enzymes, and nucleic acids encoding said enzymes, portions of the acid-tolerant enzymes, or variants thereof, wherein such enzymes are produced by the isolated strain and/or its progeny.

The present invention also provides mutated or recombinant fungal strains derived from the fungal strain and/or its progeny as provided by the present invention.

The present invention also provides methods of using isolated fungal strains of acidophilic *Fusarium oxysporum*, such as the isolated strain designated as MK7, to directly convert a wide range of feedstocks such as wheat straw, corn stover, and industrial by-products (e.g. molasses, glycerol) to valuable lipid products such as Omega-7 fatty acids and/or high-melting temperature waxes.

The present invention also provides simple, novel and cost-effective processes for converting lignocellulosic and other waste feedstocks to high value lipids using isolated fungal strains of acidophilic *Fusarium oxysporum*, such as the isolated strain designated as MK7, which is capable of withstanding extreme acidic conditions and producing powerful enzymes for degrading cellulose, lignin and hemicellulose. The organism accumulates high concentrations of valuable lipids in a cost-effective "one-step" process.

In some embodiments, the present invention teaches a method for producing an energy-rich substrate, said method comprising contacting a carbon source with an isolated *Fusarium oxysporum* strain to form a mixture, incubating said mixture for a period of time, and obtaining the energy-rich substrate following such contact.

In some embodiments, the present invention teaches an MK7 *Fusarium oxysporum* strain, for which a representative sample has been deposited as ATCC Accession Deposit No. PTA-10698.

In some embodiments, the present invention methods of producing energy-rich substrates using a *Fusarium oxysporum* strain with an rRNA sequence as disclosed in SEQ ID No.: 1.

In some embodiments, the application teaches that the carbon source used in the methods of the present invention is a biomass product.

In some embodiments, the application teaches that the carbon source used in the methods of the present invention is a cellulosic biomass product.

In some embodiments, the application teaches that the carbon source used in the methods of the present invention is a ligno-cellulosic feedstock or lingo-cellulosic waste.

In some embodiments, the application teaches that the carbon source used in the methods of the present invention is a carbohydrate.

In some embodiments, the present invention teaches methods wherein the *Fusarium oxysporum* strain and the carbon source are incubated in anaerobic or microaerobic conditions.

In some embodiments, the methods of the present invention produce an energy-rich substrate, wherein said energy-rich substrate is selected from the group consisting of ethanol and hydrogen gas.

In some embodiments, the present invention teaches a pretreatment step, wherein said pretreatment step is selected from the group consisting of: reducing the pH of the carbon source and *Fusarium oxysporum* mixture, adding manganese to the carbon source and *Fusarium oxysporum* mixture, and adding a nutrient to the carbon source and *Fusarium oxysporum* mixture before the incubation step.

In some embodiments, the energy-rich substrate produced by the methods of the present invention is a lipid, ethanol, and/or hydrogen.

In some embodiments, the energy-rich substrate produced by the methods of the present invention is a lipid.

In some embodiments, the present invention teaches a method for producing one or more energy-rich metabolites using a *Fusarium oxysporum* strain, said method comprising the steps of: a) making a mixture of a *Fusarium oxysporum* MK7 strain, and/or its progeny, with a feedstock material selected from the group consisting of ligno-cellulosic feedstocks, carbon containing waste products, carbohydrates, and a combination thereof in a container, wherein the material can support the growth of said MK7 strain and/or its progeny; b) growing said MK7 strain in said mixture to produce one or more energy-rich metabolites; and c) optionally, isolating said one or more energy-rich metabolites from the mixture; wherein a representative sample of said MK7 strain has been deposited as ATCC Accession Deposit No. PTA-10698.

In some embodiments, the present invention teaches methods of producing energy-rich substrates from wheat straw feedstock.

In some embodiments, the energy-rich substrate produced by the methods of the present invention is ethanol.

In some embodiments, the energy-rich substrate produced by the methods of the present invention is hydrogen gas.

In some embodiments, the energy-rich substrate produced by the methods of the present invention is a fatty acid methyl ester (FAME).

In some embodiments, the present invention teaches FAME selected from the group consisting of methyl tetradecanoate, methyl hexadec-9-enoate, hexadecanoic acid, methyl ester, oleic acid, linoleic acid, conjuated linolenic acid, methyl 11-octadecenoate, Octadecanoic acid, methyl ester, eicosanoic acid, methyl ester, docosanoic acid, methyl ester, and tetracosanoic acid, methyl ester.

In some embodiments, the application teaches that the FAME produced by the methods of the present invention is an Omega-7 vaccenic acid.

In some embodiments, the present invention teaches that the mixture of *Fusarium* and energy source (e.g., carbon source or feedstock) is incubated in anaerobic or microaerobic conditions.

In some embodiments, the methods of the present invention comprise a pretreatment step, wherein said pretreatment step is selected from the group consisting of: reducing the pH of the mixture, adding manganese to the mixture, and adding a nutrient to the mixture.

DETAILED DESCRIPTION

Definition

Figure 1:
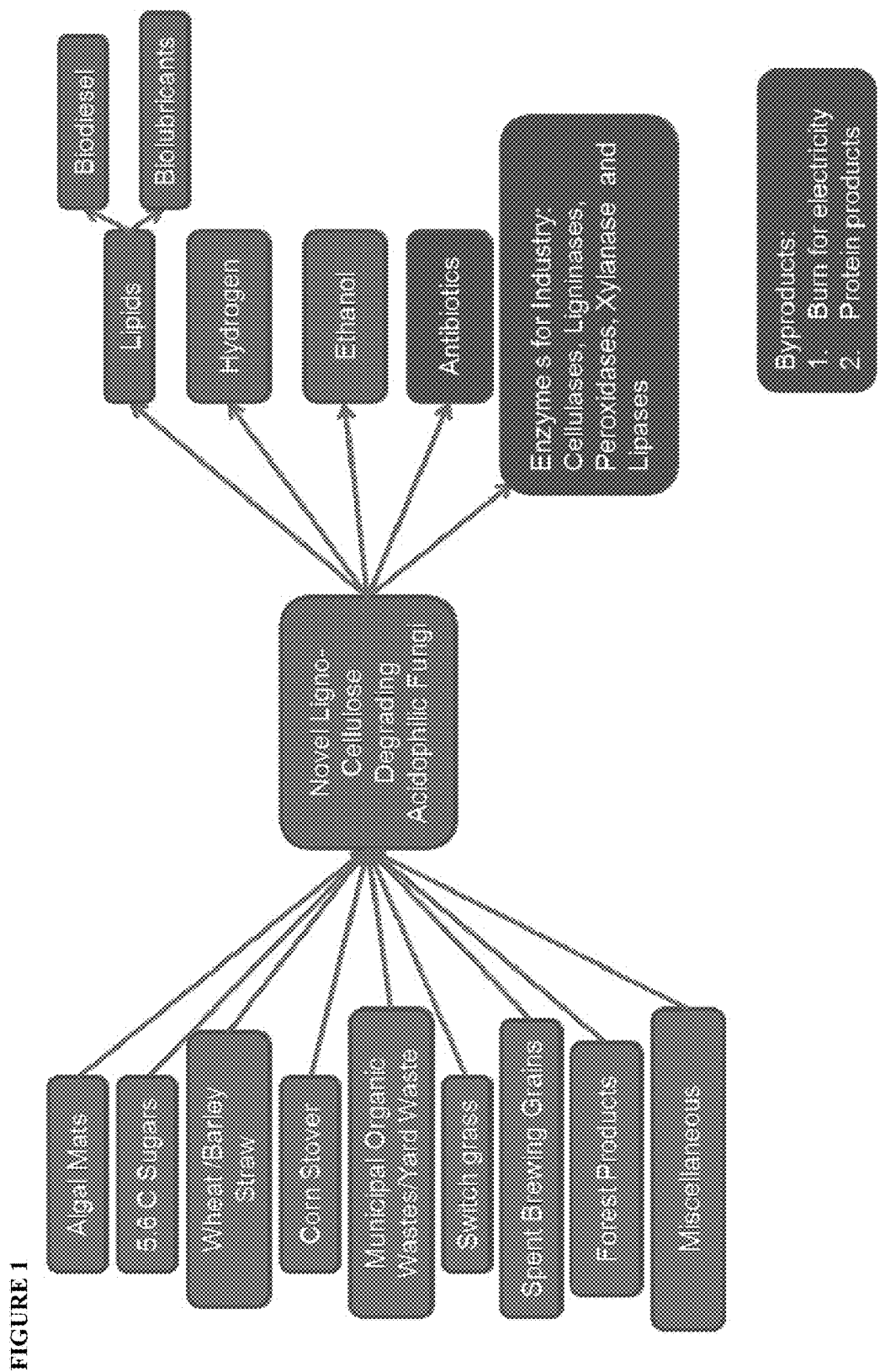
FIG. 1 depicts an inventive process that utilizes *Fusarium oxysporum* strain MK7, a novel acidophilic fungus, and/or its progeny to directly convert ligno-cellulosic feedstocks, 5 and 6 carbon sugars, and algal biomass to energy-rich substrates including lipids, ethanol and hydrogen. Additionally, the fungus can be used to produce enzymes and antibiotics for commercial applications. Additionally, the fungus is capable of neutralizing acid and binding heavy metals for the remediation of acid mine drainage.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "derived from" refers to the origin or source, and may include naturally occurring, recombinant, unpurified, or purified molecules. The proteins and molecules of the present invention may be derived from influenza or non-influenza molecules.

As used herein, the term "microaerobic" refers to an environment where the concentration of oxygen is less than the concentration of oxygen in air.

As used herein, the term "chimeric protein" refers a constructs that links at least two heterologous proteins into a single macromolecule (fusion protein).

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to a nucleic acid or portion of a nucleic acid comprising a sequence that encodes a protein. It is understood in the art that a gene also comprises non-coding sequences, such as 5' and 3' flanking sequences (such as promoters, enhancers, repressors, and other regulatory sequences) as well as introns.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homologue" or "ortholog" is known in the art and refers to related sequences that share a common ancestor or family member and are determined based on the degree of sequence identity. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations can be those containing alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined above. A fungi derived from a specific, isolated fungal strain and/or its progeny may comprise certain mutations but still retain one, two, or more, or all of the distinguishing morphological and physiological characteristics of the isolated fungi or its progeny from which they were derived.

As used herein, the term "acidophilic" refers to that an organism whose optimal growth conditions are under acidic conditions.

As used herein, the term "agent", as used herein, means a biological or chemical compound such as a simple or complex organic or inorganic molecule, a peptide, a protein or an oligonucleotide that modulates the function of a nucleic acid or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "substantially complementary" means that two nucleic acid sequences have at least about 65%, preferably about 70%, more preferably about 80%, even more preferably 90%, and even more preferably about 98%, about 98.5%, about 99%, about 99.1%, about 99.2%, about 99.3%, about 99.4%, about 99.5%, about 99.6%, about 99.7%, about 99.8%, or about 99.9%, sequence complementarity to each other. This means that primers and probes must exhibit sufficient complementarity to their template and target nucleic acid, respectively, to hybridize under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

The terms "substantially pure" and "isolated," are used interchangeably and describe anything which is substantially separated from other things. For example, it can be used to refer to a fungus, a part or form of a fungus (e.g., a conidia, pycnidia, chlamydospores, and hyphae), a protein, a peptide or a nucleic acid which is substantially separated from other cellular and/or (sub)cellular components or contaminants which naturally accompany it. The term embraces fungi, a fungal form or part, a nucleic acid or a protein which has been removed from its naturally occurring environment. Generally, the term refers to purified things having a purity of at least about 75%, at least about 80%, at least about 85%, at least about 90%, at least about 85%, at least about 90%, at least about 95%, at least about 98%, or at least about 99% by weight. Minor variants or chemical modifications typically share the same polypeptide or nucleotide sequence. A substantially pure protein or nucleic acid will typically comprise about 85 to 100% (w/w) of a protein or nucleic acid sample, more usually about 95%, and preferably will be over about 99% pure. Protein or nucleic acid purity or homogeneity can be indicated by a number of means well known in the art, such as polyacrylamide gel electrophoresis of a protein sample, followed by visualizing a single polypeptide band on a polyacrylamide gel upon staining, or by agarose gel electrophoresis of a nucleic acid sample, followed by visualizing a single polynucleotide band on an agarose gel upon staining. "Staining" may either refer to the use of $\alpha$-specific peptide or nucleic acid stains such as silver and Coomassie stains, or ethidium bromide and SYBR® stains, or may refer to the use of specific peptide or nucleic acid stains such as contacting the peptide with an antibody and visualizing the antibody using a labeled secondary antibody (e.g. conjugated to alkaline phosphatase) in the case of proteins or peptides, or contacting the nucleic acid with a complementary probe labeled for visualizing the presence of hybridization between the nucleic acid and the probe. For certain purposes higher resolution can be provided by using high performance liquid chromatography (HPLC) or a similar means for purification. Such methods are in the area of common general knowledge (see e.g. Katz, et al., 1998).

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The T m is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37°

C., and a wash in 0.1×SSC at 60° C. Hybridization procedures are well known in the art and are described by e.g. Ausubel et al., 1998 and Sambrook et al., 2001.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "recombinant" refers to an artificial combination of two otherwise separated segments of sequence, e.g., by chemical synthesis or by the manipulation of isolated segments of nucleic acids by genetic engineering techniques.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. The term "expression", as used herein, refers to the production of a functional end-product e.g., a mRNA or a protein (precursor or mature).

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, "antisense inhibition" or "antisense silencing" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al.

(1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the phrase "ligno-cellulosic feedstocks" refers to feedstocks containing ligno cellulose. Non-limiting examples of ligno-cellulosic feedstocks include, agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), ligno-cellulosic containing waste (e.g., newsprint, waste paper, brewing grains, used rubber tire (UTR), municipal organic waste, yard waste, clinical organic waste, waste generated during the production of biofuels (e.g. processed algal biomass, glycerol), and a combination thereof.

As used herein, unless otherwise specified, the term "carbohydrate" refers to a compound of carbon, hydrogen, and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment they are monosaccharides. In another embodiment they can be pyranose and furanose sugars. They can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate. These saccharide units can be arranged in any order and the linkage between two saccharide units can occur in any of approximately ten different ways. As a result, the number of different possible stereoisomeric oligosaccharide chains is enormous. In one embodiment, said carbohydrates are selected from the group consisting of monosaccharides, disaccharides, oligosaccharides, polysaccharides, and a combination thereof.

As used herein, the term "monosaccharide" refers to sugar monomers selected from the group consisting of three-carbon sugars (trioses), four-carbon sugars (tetroses), five-carbon sugars (pentoses), six-carbon sugars (hexoses), et al., and a combination thereof. In one embodiment, the five-carbon sugars are selected from the group consisting of ketopentose (e.g., ribulose, xylulose), aldopentose (ribose, arabinose, xylose, lyxose), deoxy sugar (deoxyribose), and a combination thereof. In one embodiment, the six-carbon sugars are selected from the group consisting of aldohexoses (e.g., allose, altrose, glucose, mannose, glucose, idose, galactose, talose), cyclic hemiacetals, ketohexoses (e.g., psicose, fructose, sorbose, tagatose). In one embodiment, said monosaccharides are selected from the group consisting of trioses, tetroses, pentoses, hexoses, heptoses, et al., and a combination thereof. In one embodiment, the monosaccharides are in linear form; in another embodiment, the monosaccharides are in cyclic form.

As used herein, the phrase "fermentable sugars" refers to sugar compounds that can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. Specific value-added products that may be produced by the methods of the invention include, but not limited to, biofuel (including ethanol, butanol and isobutanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, transferases and xylanases; and chemical feedstocks.

As used herein, the term "fungus" or "fungi" refers to a distinct group of eukaryotic, spore-forming organisms with absorptive nutrition and lacking chlorophyll.

As used herein, the term "acidification material" refers to any materials, chemical compounds, agents, compositions which when added into a solvent (e.g., water), gives a solution with a hydrogen ion activity greater than in pure solvent (e.g., water). The material can be in gas, liquid, or solid form. The material can be organic and/or inorganic. Non-limiting examples of acidification material include any material comprises hydrogen halides and their solutions (e.g., hydrochloric acid (HCl), hydrobromic acid (HBr), hydroiodic acid (HI)), halogen oxoacids (e.g., hypochloric acid, chloric acid, perchloric acid, periodic acid and corresponding compounds for bromine and iodine), sulfuric acid ($H_2SO_4$), fluorosulfuric acid, nitric acid ($HNO_3$), phosphoric acid ($H_3PO_4$), fluoroantimonic acid, fluoroboric acid, hexafluorophosphoric acid, chromic acid ($H_2CrO_4$), sulfonic acids, methanesulfonic acid (aka mesylic acid, $MeSO_3H$), ethanesulfonic acid (aka esylic acid, $EtSO_3H$), benzenesulfonic acid (aka besylic acid, $PhSO_3H$), p-toluenesulfonic acid (aka tosylic acid) ($CH_3C_6H_4SO_3H$), trifluoromethanesulfonic acid (aka triflic acid, $CF_3SO_3H$), carboxylic acids (e.g., acetic acid, citric acid, formic acid, gluconic acid, lactic acid, oxalic acid, tartaric acid), Vinylogous carboxylic acids (e.g., ascorbic acid, meldrum's acid), acid salts (e.g., sodium bicarbonate ($NaHCO_3$), sodium hydrosulfide (NaHS), sodium bisulfate ($NaHSO_4$), monosodium phosphate ($NaH_2PO_4$), and disodium phosphate ($Na_2HPO_4$)).

As used herein, the term "energy-rich metabolites" refers to metabolites produced by an organism (e.g., a fungus), wherein the metabolite can be directly used as biofuel (e.g., alcohol), or as precursor for biofuel production (e.g., lipids for biodiesel).

As used herein, the term "neutralize", "neutralizing", and "neutralization" refers to a chemical reaction in aqueous solutions, wherein an acid and a base react to form water and a salt, and wherein the pH of the solution is brought closer to 7.

As used herein, the term "manganese donor" refers to a composition or compound which can provide manganese ion (e.g., manganese(I), manganese(II), and manganese(III)) in an aqueous solution. Non-limiting example of manganese donors include, $Mn_2(CO)_{10}$, $K_5[Mn(CN)_6NO$, $MnCl_2$, $MnF_2$, $MnBr_2$, MnO, $MnO_2$, $MnCl_3$, $MnF_3$, $MnBr_3$, $MnCO_3$, $Mn(CH_3COO)_2$, $C_6H_9MnO_6$, $MnTiO_3$, $[CH_3COCH=C(O)CH_3]_2Mn$, $[C_6H_{11}(CH_2)_3CO_2]_2Mn$, $(HCO_2)_2Mn$, $Mn(C_5HF_6O_2)_2$, $MnI_2$, $(C_3H_5O_3)_2Mn$, $MnMoO_4$, $Mn(NO_3)_2$, $Mn(ClO_4)_2$, $C_{32}H_{16}MnN_8$, $MnSO_4$, $(CH_3COO)_3Mn$, $C_{32}H_{16}ClMnN_8$, $C_{48}H_{28}ClMnN_4O_8$, $C_5H_4CH_3Mn(CO)_3$, $Mn(C_5H_4C_2H_5)_2$, and $C_{16}H_{22}Mn$.

As used herein, the phrase "pH buffering materials" refers to refers to compositions that when added in a liquid mixture, can maintain the pH of said liquid mixture wherein the pH is kept around about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5 about 6.6, about 6.7, about 6.8, about 6.9, or about 7.0. For example, the pH of the liquid mixture is in a range between about 0.5 to about 3.0. Such composition can comprise compounds such as acid, acid salts, basic and basic salts, for example, $HCl$, $H_2NO_3$, $H_2SO_4$, $NaHCO_3$, $NaHS$, $NaHSO_4$, $NaH_2PO_4$, $Na_2HPO_4$, $NaHSO_3$, $KHCO_3$, $KHS$, $KHSO_4$, $KH_2PO_4$, $K_2HPO_4$, $KHSO_3$, $NaOH$, $KOH$, $Mg(OH)_2$, $Na_2CO_3$, $K_2CO_3$, $KHCO_3$, $CaCO_3$, $MgCO_3$, $Na_2S$, $K_2S$ et al.

As used herein, the term "aerobic conditions" refers to conditions where sufficient oxygen, is provided, and anaerobic respiration in a microorganism growing under such conditions is prohibited.

As used herein, the term "substantially aerobic conditions" refers to conditions wherein the supply of oxygen is limited, but the cellular respiration in an organism is dominantly aerobic respiration.

As used herein, the term "biofuel" (also called bioenergy) is defined as solid, liquid or gaseous fuel derived from relatively recently dead or dying biological material and is distinguished from fossil fuels, which are derived from long dead biological material. It can be produced from any biological carbon source theoretically. Biofuels can be classified into first generation biofuels (which are made from sugar, starch, vegetable oil, and animal fats, including but not limited to vegetable oil, biodiesel, bioalcohols, bioethers, biogas, syngas and solid biofuels), second generation biofuels (which are produced from biomass of non food crops, also called cellulosic biofuels, including but not limited to, biohydrogen, biomethanol, DMF, Bio-DME, Fischer-Tropsch diesel, biohydrogen diesel, mixed alcohols and wood diesel), and third generation biofuels (also called algae fuels, which are made from algae).

The term "biofuel precursor" refers to an organic molecule in which all carbon contained within is derived from biomass and is biochemically converted. It can be further converted either chemically or biochemically, into a biofuel. For example, a biofuel precursor includes, but is not limited to, e.g. isobutanol, isopropanol, propanol, 2-butanol, butanol, pentanol, 2-pentanol, 3-pentanol, 3-methyl-1-butanol, 2-methyl-1-butanol, 3-methyl-2-butanol, and lipid.

As used herein, the term "biodiesel" refers to a vegetable oil or animal fat-based diesel fuel consisting of long chain alkyl (e.g., methyl, propyl or ethyl) esters. It can be made by chemically reacting lipids with one or more types of alcohol in a transesterification reaction. Chemically it comprises a mix of mono-alkyl esters of long chain fatty acids. Alcohols that can be used to produce biodiesel include, but are not limited to, methanol, ethanol, propanol, isopropanol, butanol, isobutanol, and 2-ethoxyethanol. Acidic or alkaline catalyst can be applied to facilitate esterification of fatty acids. Glycerol is produced as a by-product in such reactions.

As used herein, the phrase "fatty acids" refers to long-chained molecules having a methyl group at one end and a carboxylic acid group at the other end.

As used herein, the phrase "isolated fungus" refers to any composition comprising a fungus population which is obtained from a natural source.

As used herein, the term "bioalcohols" refers to alcohols synthesized biologically, including, but not are not limited to, bioethanol, biomethanol, biobutanol, and other bioalcohols.

As used herein, the term "alcohol" refers to any organic compound in which a hydroxyl group (—OH) is bound to a carbon atom of an alkyl or substituted alkyl group. An important group of alcohols is formed by the simple acyclic alcohols, the general formula for which is $C_nH_{2n+1}OH$.

As used herein, the term "biogas" refers to a gas produced by the biological breakdown of organic matter in the absence of oxygen. Biogas originates from biogenic material and is a type of biofuel.

As used herein, the term "siderophores" refers to small, high-affinity metal ion chelating compounds secreted by microorganisms such as bacteria, fungi and grasses.

As used herein, the term "feedstock" refers to a raw material or mixture of raw materials supplied to a biocatalyst or fermentation process from which other products can be made. For example, a carbon source, such as biomass or the carbon compounds derived from biomass, is a feedstock for a biocatalyst that produces a biofuel and/or biofuel precursor in a fermentation process. In addition, a feedstock may contain nutrients other than a carbon source. Feedstock can also be municipal, industrial, and farm sewage waste.

As used herein, the term "biocatalyst" refers to a living system or cell of any type that speeds up chemical reactions by lowering the activation energy of the reaction and is neither consumed nor altered in the process. Biocatalysts may include, but are not limited to, microorganisms such as yeasts, fungi, bacteria, and archaea. For example, the isolated fungal strain of the present invention can be used as a biocatalyst in the production of biofuels.

As used herein, the term "fermentation" or "fermentation process" refers a process in which a biocatalyst is cultivated in a culture medium containing raw materials, such as feedstock and nutrients, wherein the biocatalyst converts raw materials, such as a feedstock, into products.

As used herein, the term "carbon source" generally refers to a substance suitable to be used as a source of carbon for prokaryotic or eukaryotic cell growth. Carbon sources include, but are not limited to, biomass hydrolysates, carbohydrates (e.g., starch, sucrose, polysaccharides, and monosaccharides), cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis.

As used herein, the term "biomass" refers to biological material derived from living, or recently living organisms, e.g., stems, leaves, and starch-containing portions of green plants, or wood, waste, forest residues (dead trees, branches and tree stumps), yard clippings, wood chips, or materials derived from algae or animals, and is mainly comprised of starch, lignin, pectin, cellulose, hemicellulose, and/or pectin. Biomass may also include biodegradable wastes that can be burnt as fuel. It excludes organic material such as fossil fuel which has been transformed by geological processes into substances such as coal or petroleum. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feedstock for fermentations using a biocatalyst.

As used herein, the term "cellulosic biomass" refers to biomass composed primarily of plant fibers that are inedible or nearly inedible by humans and have cellulose as a prominent component. There fibers may be hydrolyzed to yield a variety of sugars that can be fermented by microorganisms. Examples of cellulosic biomass include grass, wood, and cellulose-rich residues resulting from agriculture or the forest products industry.

As used herein, the term "starch" refers to a polymer of glucose readily hydrolyzed by digestive enzymes. Starch is usually concentrated in specialized portions of plants, such as potatoes, corn kernels, rice grains, wheat grains, and sugar cane stems.

As used herein, the term "lignin" refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

As used herein, the term "cellulose" refers to a long-chain polymer polysaccharide carbohydrate of beta-glucose of formula $(C_6H_{10}O_5)_n$, usually found in plant cell walls in combination with lignin and any hemicellulose.

As used herein, the term "hemicellulose" refers to a class of plant cell-wall polysaccharides that can be any of several heteropolymers. These include xylan, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction. Proportions of each of the monosaccharides in relation to D-galacturonic acid vary depending on the individual plant and its micro-environment, the species, and time during the growth cycle. For the same reasons, the homogalacturonan and RG-I fractions can differ widely in their content of methyl esters on GalA residues, and the content of acetyl residue esters on the C-2 and C-3 positions of GalA and neutral sugars.

As used herein, the phrase "facultative anaerobic organism" or a "facultative anaerobic microorganism" or a "facultative anaerobic biocatalyst" is defined as an organism that can grow in either the presence or in the absence of oxygen, such as the fungal strains isolated in the present invention.

As used herein, the term "byproduct" means an undesired product related to the production of biofuel and/or biofuel precursor. Byproducts are generally disposed as waste, adding cost to a process.

As used herein, the term "co-product" means a secondary or incidental product related to the production of biofuel and/or biofuel precursor. Co-products have potential commercial value that increases the overall value of biofuel precursor production, and may be the deciding factor as to the viability of a particular biofuel precursor production process.

As used herein, the term "distillers dried grains", abbreviated as DDG, refers to the solids remaining after a fermentation, usually consisting of unconsumed feedstock solids, remaining nutrients, protein, fiber, and oil, as well as biocatalyst cell debris. The term may also include soluble residual material from the fermentation and is then referred to as "distillers dried grains and solubles" (DDGS). DDG or DDGS are an example of a co-product from a biofuel precursor production process.

As used herein, the term "nutrient" is defined as a chemical compound that is used by a biocatalyst to grow and survive. Nutrients can be organic compounds such as carbohydrates and amino acids or inorganic compound such as metal salts.

As used herein, the term "complex nutrient" is defined as a nutrient source containing mostly monomeric organic compounds used by a biocatalyst for the production of proteins, DNA, lipids, and carbohydrates. The term "rich nutrient" is used interchangeably throughout with the term complex nutrient. Typically, complex nutrients or rich nutrients are derived from biological materials, such as slaughterhouse waste, dairy wastes, or agricultural residues. Complex nutrients or rich nutrients include, but are not limited to: yeast extract, tryptone, peptone, soy extract, corn steep liquor, soy protein, and casein.

As used herein, the phrase "aerobic metabolism" refers to a biochemical process in which oxygen is used to make energy, typically in the form of ATP, from carbohydrates. Typical aerobic metabolism occurs via glycolysis and the TCA cycle, wherein a single glucose molecule is metabolized completely into carbon dioxide in the presence of oxygen.

As used herein, the phrase "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and fermentation, in which the electrons from NADH are utilized to generate a reduced product via a "fermentative pathway."

As used herein, the term "recombinant microorganism" and "recombinant host cell" are used interchangeably and refer to microorganisms that have been genetically modified to express or over-express endogenous polynucleotides, or to express heterologous polynucleotides, such as those included in a vector, or which have a reduction in expression of an endogenous gene. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

As used herein, the term "fermentation" refers to a method to produce biofuel and other products where biomass (pretreated or unpretreated) was fermented by microorganisms (e.g., bacteria, cyanobacteria, yeast, fungi or algae).

As used herein, the terms "microbiological fermentation" refers to a process where organic substances are broken down and re-assembled into products by microorganisms. The substances may include, but not limited to, glucose, sucrose, glycerol, starch, maltodextrine, lactose, fats, hydrocarbons, protein, ammonia, nitrate, phosphorus sources. The products may include, but not limited to, traditional products (including but not limited to, bread, beer, wine, spirits, cheese, dairy products, fermented meats and vegetables, mushrooms, soy sauce and vinegar), agricultural products (including but not limited to, gibberellins, fungicides, insecticides, silage, amino acids such as L-Glutamine, L-Lysine, L-Tryptophan, L-Throenine, L-aspartic (+), L-arylglycines), enzymes (including but not limited to, carbohydrates, celluloses, lipases, pectinases, proteases), fuels and chemical feedstocks (including but not limited to, acetone, butanol, butanediol, isopropanol, ethyl alcohol, glycerol, methane, glycerol, butyric acid, methane, citric acid, fumaric acid, lactic acid, propionic acid, succinic acid, itaconic acid, acetic acid, 3-hydroxypropionic acid, glyconic acid, tartaric acid and L-glutaric acid or salts of any of these acids), nucleotides, organic acids, pharmaceuticals and related compounds (including but not limited to, alkaloids, antibiotics, hormones, immunosuppressant, interferon, steroids, vaccines, vitamins) and polymers (including but not limited to, alginates, dextran, gellan, polyhydroxybutyrate, scleroglucan and xanthan). The microorganisms used for fermentation may include both prokaryotic microorganisms (including bacteria, cyanobacteria) and eukaryotic microorganisms (including yeast, fungi and algae).

As used herein, the phrase "energy crops" refers to plants grown as a low cost and low maintenance harvest used to make biofuels, or directly exploited for its energy content. Commercial energy crops are typically densely planted, high yielding crop species where the energy crops will be burnt to generate power. Woody crops such as Willow or Poplar are widely utilized as well as tropical grasses such as *Miscanthus* and *Pennisetum purpureum* (both known as elephant grass). If carbohydrate content is desired for the production of biogas, whole-crops such as maize, Sudan grass, millet, white sweet clover and many others, can be made into silage and then converted into biogas.

As used herein, the term micro-aerobic refers to an environment in which the concentration of oxygen is less than that in air, but cellular respiration in an organism is dominantly aerobic respiration.

*Fusarium*

*Fusarium* species may produce three types of spores called macroconidia, microconidia, and chlamydospores. The macrocodinia are produced in a specialized structure called a sporodochium in which the spore mass is supported by a superficial cushionlike mass of short monophialides bearing the macroconidia, or produced on monophialides and polyphialides in the aerial mycelium. A monophialide is a condiophore with only one opening or pore through which endoconidia are extruded, while a polyphialide has two or more such openings or pores. Some conidia are intermediate in size and shape, and these have been referred to as both macroconidia and mesoconidia. Microconidia are produced in the aerial mycelium but not in sporodochia. They may be produced in false heads only or in false heads and chains on either monophialides or polyphialides. False heads occur when a drop of moisture forms on the tip of the conidiophore and contains the endoconidia as they are produced. Microconidia are of various shapes and sizes, and those produced in chains have a truncate base. The third type of spore formed by *Fusarium* species is a chlamydospore, which is a thick-walled spore filled with lipid-like material that serves to carry the fungus over winter in soil when a suitable host is not available. The chlamydospores may be borne singly, in pairs, in clumps, or in chains, and the outer wall may be smooth or rough. Morphology of these spores can be used to separate species in *Fusarium*.

Methods of transferring and culturing *Fusarium* species are well known in the art. For example, the single-spore method and the hyphal-tip method are the primary means used to initiate and transfer cultures of *Fusarium* species. The hyphal-tip method is used to transfer cultures of *Fusarium* species that mutate rapidly after being transferred by single conidia. The transfer is done under the dissecting microscope, in much the same manner as the transfer of a single germinating conidium. The four media used for growing *Fusarium* species for identification are carnation leaf agar (Fisher et al., 1982, Carnation leaves as a substrate and for preserving *Fusarium* species. *Phytopathology* 72:151-153), potato dextrose agar (Nelson et al., 1983. *Fusarium* species: an illustrated manual for identification. Pennsylvania State University Press, University Park), KCl medium (Fisher et al., 1983. Taxonomic importance of microconidial chains in *Fusarium* section Liseola and effects of water potential on their formation. *Mycologia* 75:693-698), and soil agar (Klotz et al., 1988. A medium for enhancement of chlamydospore formation in *Fusarium* species. *Mycologia* 80:108-109), each of which is incorporated by reference in its entirety.

The majority of *Fusarium* species isolated from nature produce their macroconidia on sporodochia. The sporodochial type often mutates in culture, especially on media rich in carbohydrates. Mutations may also occur in nature, but are rare. These mutants may give rise to others so that a mutational sequence occurs. In pathogenic isolates, these mutants frequently exhibit a loss of virulence and the ability to produce toxins may be reduced or lost. The two major types of mutants produced from the sporodochial type are the pionnotal type (e.g., the production of little or no aerial mycelium; production of abundant macroconidia on the surface of the colony causing the surface to appear shiny and wet; more intense pigmentation of colonies than of the sporodochial colonies; the production of longer and thinner macroconidia than those produced by the sporodochial type; less virulent than the sporodochial type and may also lose the ability to produce toxins) and the mycelial type (e.g., the production of abundant aerial mycelium; the production of very few to no macroconidia; the frequent lack of sporodochia, sclerotia and pigmentation in culture; mutants that may be less virulent than the sporodochial type and may also lose the ability to produce toxins).

Procedures that reduce mutant populations include, but are not limited to, initiating cultures from single conidia; initiating cultures from single hyphal tips; avoiding media rich in carbohydrates; and keeping subculturing to a minimum, as discussed in Nelson et al. (1983, *Fusarium* species: an illustrated manual for identification. Pennsylvania State University Press, University Park).

Non-limiting example of *Fusarium* species include, *Fusarium angustum* (synonym of *F. oxysporum*), *Fusarium aquaeductuum* (e.g., *Fusarium aquaeductuum* var. *dimerum*, synonym of *F. dimerum*), *Fusarium aquaeductuum* var. *media* (e.g., *Fusarium bostrycoides*, synonym of *F. oxysporum*, *Fusarium chlamydosporum* (synonym of *Dactylium fusarioides*, *F. fusarioides*, *F. sporotrichioides* var. *chlamydosporum*, *F. tricinctum*), *Fusarium coeruleum* (synonym *F. solani* var. *coeruleum*), *Fusarium conglutinans* (synonym of *F. oxysporum*), *Fusarium dianthi* (synonym of *F. oxysporum*), *Fusarium dimerum* (synonyms *F. aquaeductuum* var. *dimerum*, *F. episphaeria*), *Fusarium episphaeria* (synonym of *F. dimerum*), *Fusarium eumartii* (synonym of *F. solani*), *Fusarium fujikuroi* (synonym of *F. moniliforme*), *Fusarium fusarioides* (synonym of *F. chlamydosporum*), *Fusarium illudens* (synonym of *F. solani*), *Fusarium incarnatum* (synonym of *F. semitectum*), *Fusarium javanicum* (synonym of *F. solani*), *Fusarium lini* (synonym of *F. oxysporum*), *Fusarium moniliforme* (synonym of *F. proliferatum*, *F. verticillioides*, *F. fujikuroi*, *F. verticillioides*), *Fusarium moniliforme* var. *intermedium* (synonym of *F. proliferatum*), *Fusarium napiforme*, *Fusarium orthoceras* (synonym of *F. oxysporum*), *Fusarium oxysporum* (synonym of *F. angustum*, *F. bostrycoide,s F. bulbigenum*, *F. conglutinans*, *F. dianthi*, *F. lini*, *F. orthoceras*, *F. tracheiphilum*, *F. vasinfectum*), *Fusarium pallidoroseum* (synonym of *F. semitectum*), *Fusarium proliferatum* (synonym of *F. moniliforme*, *F. moniliforme* var. *intermedium*), *Fusarium roseum* (synonym of *F. semitectum*), *Fusarium roseum* var. *arthrosporioide* (synonym of *F. semitectum*), *Fusarium sacchari*, *Fusarium semitectum* (synonym of *F. incarnatum*, *F. pallidoroseum*, *F. roseum*, *F. roseum* var. *arthrosporioide*, *Pseudofusarium semitectum*), *Fusarium solani* (synonym of *F. eumartii*, *F. illudens*, *F. javanicum*, *F. tumidum*, *F. ventricosum*, *Fusisporium solani*, *Nectria haematococca*), *Fusarium solani* var. *coeruleum* (synonym of *F. coeruleum*), *Fusarium sporotrichiella* var. *sporotrichioides* (synonym of *F. sporotrichoides*), *Fusarium sporotrichioides* var. *chlamydosporum* (synonym of *F. chlamydosporum*), *Fusarium sporotrichoides* (synonym of *F. sporotrichiella* var. *sporotrichioides*, *F. tricinctum*, *Sporotrichella rosea*), *Fusarium sub glutinous*, *Fusarium tabacinum* (teleomorph of *Plectosphaerella cucumerina*), *Fusarium tracheiphilum* (synonym of *F. oxysporum*), *Fusarium tricinctum* (synonym of *F. chlamydosporum*, *F. sporotrichoides*), *Fusarium tumidum* (synonym of *F. solani*), *Fusarium vasinfectum* (synonym of *F. oxysporum*), *Fusarium ventricosum* (synonym of *F. solani*), and *Fusarium verticillioides* (synonym of *F. moniliforme*).

More information regarding *Fusarium* species, methods of identifying, isolating and culturing is described in Nelson et al., (Taxonomy, Biology, and Clinical Aspects of *Fusarium* Species, 1994, *Clinical Microbiology Reviews*, 7(4): 479-504), Toussoun and Nelson (1976, *Fusarium*), Booth (*Fusarium*: laboratory guide to the identification of the major species, 1977, Commonwealth Mycological Institute, ISBN 0851983839, 9780851983837) and Leslie et al. (The *Fusarium* laboratory manual, 2006, Wiley-Blackwell, ISBN 0813819199, 9780813819198), each of which is herein incorporated by reference in its entirety.

*Fusarium oxysporum*

*Fusarium oxysporum*, also referred to as pathogen of Panama disease or Agent Green, is a fungus that causes *Fusarium* wilt disease in more than a hundred species of plants. It does so by colonizing the water-conducting vessels (xylem) of the plant. As a result of this blockage and breakdown of xylem, symptoms appear in plants such as leaf wilting, yellowing and eventually plant death. Interest in *Fusarium oxysporum* as a herbicide was first raised after the discovery in the 1960s that it was the causative agent in the destruction of the Hawaiian coca population.

Members of the *Fusarium oxysporum* species complex (FOSC) are the most common phytopathogenic *Fusaria*. They cause vascular wilts of over 100 cultivated plant species, including tomato, potato, sugarcane, bean, cowpea, date and oil palm, as well as cooking and dessert bananas (Beckman, 1987. The Nature of Wilt Diseases of Plants. *The American Phytopathological Society Press, St. Paul*). Because it is a long-lived, soil-borne pathogen, infested soil remains contaminated indefinitely, so only resistant varieties can be grown on that site.

*Fusarium oxysporum* f sp. *lycopersici* strain 4287 (race 2, VCG 0030) was fully sequenced. The genome size is estimated to be 59.9 Mb. This characteristic permits extensive investigation of host-pathogen interactions, pathogen infection, and plant defense mechanisms, using the model plant system *A. thaliana*. Based on intensive study over the past 10 years, this strain has displayed remarkable phenotypic stability, including mycelial growth on different culture media, sporulation and high virulence. This strain is also highly amenable to transformation, via both protoplasts and *Agrobacterium tumefaciens*, and transformation-mediated gene disruption. A mitotic linkage map was created from the protoplast fusion of two strains of *F. oxysporum* f sp. *lycopersici*, VCG 0030 (Teunissen et al. 2003, A Near-Isogenic *Fusarium oxysporum* f sp. *lycopersici* Strain with a Novel Combination of Avirulence Characteristics, *Phytopathology*, 93(11): 1360-1367). A novel and highly efficient gene knock-out technique and molecular cytological tools also have been developed (Khang et al., 2005, A dual selection based, targeted gene replacement tool for *Magnaporthe grisea* and *Fusarium oxysporum. Fungal Genet. Biol.* 42:483-492). Microarray analysis for *Fusarium oxysporum* is also available (Mcfadden et al., 2006, *Fusarium* wilt (*Fusarium oxysporum* f sp. *vasinfectum*) genes expressed during infection of cotton (*Gossypium hirsutum*), Molecular Plant Pathology 7(2): 87-101).

Macroscopic morphology of *Fusarium oxysporum*, may vary significantly on different media. The description below is based upon growth on potato flakes agar at 25° C. with on/off fluorescent light cycles of approximately 12 hours each. Hyphae are septate and hyaline. Conidiophores are short (when contrasted with those of *F. solani*) and simple (usually not branched). Macroconidia usually produced abundantly, slightly sickle-shaped, thin-walled, with an attenuated apical cell and a foot-shaped basal cell. They are three to 5-septate measuring 23-54×3-4.5 µm. Microconidia are abundant, mostly non-septate, ellipsoidal to cylindrical, slightly curved or straight, 5-12×2.3-3.5 µm occurring in false heads (a collection of conidia at the tip of the phialide) from short monophialides. Chlamydoconidia are present and often abundant, occurring singly and in pairs. While *F. solani* is the most common clinical isolate, *Fusarium oxysporum* appears to be the second most common species recovered. It has been reported in skin and nail infections, in subcutaneous disease, in a neutropenic child managed with granulocyte colony-stimulating factor, in a disseminated infection in hemophagocytic lymphohistiocytosis, and in a fatal case involving a cross reaction with a pan-*Candida* genus probe. The species is usually easily identified by its lavender color on potato dextrose agar, its short monophialides, and microconidia formed only in false heads.

Non-limiting examples of previously isolated *Fusarium oxysporum* forms include, *Fusarium oxysporum* 247, *Fusarium oxysporum* CL57, *Fusarium oxysporum* f *cubense*, *Fusarium oxysporum* f *perniciosum*, *Fusarium oxysporum* f sp. *aechmeae*, *Fusarium oxysporum* f sp. *albedinis*, *Fusarium oxysporum* f sp. *allii*, *Fusarium oxysporum* f sp. *apii*, *Fusarium oxysporum* f sp. *arctii*, *Fusarium oxysporum* f sp. *asparagi*, *Fusarium oxysporum* f sp. *basilici*, *Fusarium oxysporum* f sp. *batatas*, *Fusarium oxysporum* f sp. *betae*, *Fusarium oxysporum* f sp. *bouvardiae*, *Fusarium oxysporum* f sp. *bulbigenum*, *Fusarium oxysporum* f sp. *callistephi*, *Fusarium oxysporum* f sp. *canariensis*, *Fusarium oxysporum* f sp. *cannabis*, *Fusarium oxysporum* f sp. *carthami*, *Fusarium oxysporum* f sp. *cassiae*, *Fusarium oxysporum* f sp. *cattleyae*, *Fusarium oxysporum* f sp. *cepae*, *Fusarium oxysporum* f sp. *chrysanthemi*, *Fusarium oxysporum* f sp. *ciceris*, *Fusarium oxysporum* f sp. *colocasiae*, *Fusarium oxysporum* f sp. *conglutinans*, *Fusarium oxysporum* f sp. *cucumerinum*, *Fusarium oxysporum* f sp. *cucurbitacearum*, *Fusarium oxysporum* f sp. *cyclaminis*, *Fusarium oxysporum* f sp. *dianthi*, *Fusarium oxysporum* f sp. *elaeidis*, *Fusarium oxysporum* f sp. *erythroxyli*, *Fusarium oxysporum* f sp. *fabae*, *Fusarium oxysporum* f sp. *foetens*, *Fusarium oxysporum* f sp. *fragariae*, *Fusarium oxysporum* f sp. *gladioli*, *Fusarium oxysporum* f sp. *glycines*, *Fusarium oxysporum* f sp. *hebes*, *Fusarium oxysporum* f sp. *heliotropii*, *Fusarium oxysporum* f sp. *koae*, *Fusarium oxysporum* f sp. *lactucae*, *Fusarium oxysporum* f sp. *lagenariae*, *Fusarium oxysporum* f sp. *lentis*, *Fusarium oxysporum* f sp. *lilii*, *Fusarium oxysporum* f sp. *lini*, *Fusarium oxysporum* f sp. *loti*, *Fusarium oxysporum* f sp. *luffae*, *Fusarium oxysporum* f sp. *lupini*, *Fusarium oxysporum* f sp. *lycopersici*, *Fusarium oxysporum* f sp. *matthiolae*, *Fusarium oxysporum* f sp. *medicaginis*, *Fusarium oxysporum* f sp. *melongenae*, *Fusarium oxysporum* f sp. *melonis*, *Fusarium oxysporum* f sp. *momordicae*, *Fusarium oxysporum* f sp. *narcissi*, *Fusarium oxysporum* f sp. *nelumbicola*, *Fusarium oxysporum* f sp. *niveum*, *Fusarium oxysporum* f sp. *opuntiarum*, *Fusarium oxysporum* f sp. *passiflorae*, *Fusarium oxysporum* f sp. *phaseoli*, *Fusarium oxysporum* f sp. *pini*, *Fusarium oxysporum* f sp. *pisi*, *Fusarium oxysporum* f sp. *radicis-cucumerinum*, *Fusarium oxysporum* f sp. *radicis-lycopersici*, *Fusarium oxysporum* f sp. *rapae*, *Fusarium oxysporum* f sp. *raphani*, *Fusarium oxysporum* f sp. *rauvolfiae*, *Fusarium oxysporum* f sp. *rhois*, *Fusarium oxysporum* f sp. *ricini*, *Fusarium oxysporum* f sp. *sesami*, *Fusarium oxysporum* f sp. *spinaciae*, *Fusarium oxysporum* f sp. *strigae*, *Fusarium oxysporum* f sp. *tracheiphilum*, *Fusarium oxysporum* f sp. *tulipae*, *Fusarium oxysporum* f sp. *vanillae*, *Fusarium oxysporum* f sp. *vasinfectum*, *Fusarium oxysporum* f sp. *voandzeiae*, *Fusarium oxysporum* f sp. *zingiberi*, *Fusarium oxysporum* f *tuberosi*, *Fusarium oxysporum* Fo47, *Fusarium oxysporum* Fo5176, *Fusarium oxysporum* FOL 4287, *Fusarium oxysporum* Fov24500, *Fusarium oxysporum* 115, *Fusarium oxysporum* MN25, *Fusarium oxysporum* NRRL 25433, *Fusarium oxysporum* NRRL 26406, *Fusarium oxysporum* NRRL 32931, *Fusarium oxysporum* PHW808, *Fusarium oxysporum* PHW815, and *Fusarium oxysporum* var. *meniscoideum*.

Isolated Fungal Strain

The present invention provides an isolated ligno-cellulose degrading, acidophilic fungal strain of *Fusarium oxysporum* and its progeny, wherein the isolated fungal strain and its progeny have at least the following identifying characteristics:

a) the isolated strain is acidophilic and can grow at pH ranging from about 0.7 to about 7.5; and
b) producing lipids from ligno-cellulosic feedstocks, carbon containing waste products, carbohydrates, or a combination thereof under aerobic or substantially aerobic conditions.

In one embodiment, the isolated strain of the present invention further comprises one or more the following additional identifying characteristics:

c) producing ethanol and/or hydrogen from ligno-cellulosic feedstocks, carbon containing waste products, carbohydrates, or a combination thereof under anaerobic or substantially anaerobic conditions;
d) resisting to Mn concentrations of up to 25 mM, As concentrations of up to 250 mM or 300 mM, and Hg concentrations of up to 100 mM;
e) being able to dewax wheat straw and other plant material;
f) ability to produce lipids from algal feedstocks and from waste generated during biofuel production (e.g. processed algal biomass, glycerol) under aerobic or substantially aerobic conditions;
g) ability to produce ethanol and/or hydrogen from algal feedstocks and from waste generated during biofuel production (e.g. processed algal biomass, glycerol) under anaerobic or substantially anaerobic conditions;
h) ability to produce Diisooctyl phthalate (DIOP);
i) ability to produce Hexanedioic acid, mono(2-ethylhexyl) ester; and
j) comprising an 18S rRNA and ITS region DNA sequence that shares at least 98% identity to SEQ ID NO. 1.

In one embodiment, said isolated fungal strain of *Fusarium oxysporum* is the strain designated as MK7, which has been deposited as ATCC Accession Deposit No. PTA-10698, or progeny thereof.

In some embodiments, said ligno-cellulosic feedstocks are selected from the group consisting of agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), ligno-cellulosic containing waste (e.g., newsprint, waste paper, brewing grains, used rubber tire (UTR), municipal organic waste, yard waste, clinical organic waste, waste generated during the production of biofuels (e.g. processed algal biomass, glycerol), and a combination thereof. In some embodiments, the carbohydrates are selected from the group consisting of monosaccharides, disaccharides, oligosaccharides, polysaccharides, and mixture thereof.

In some embodiments, said isolated fungal strain and/or its progeny can grow at a low pH of at most about 7.0, about 6.5, about 6.0, about 5.5, about 5.0, about 4.5, about 4.0, about 3.5, about 2.0, about 1.8, about 1.6, about 1.4, about 1.2, about 1.0, about 0.9, about 0.8, or about 0.7 or about 0.6, or about 0.5, For example, said fungal strain can grow at a low pH ranging from about 0.7 to about 2.0.

The isolated strain of the present invention can produce lipids at high quantity within the low pH ranges as described above. In one embodiment, the isolated strain can convert feedstock at a higher rate within a low pH as described above than any other *Fusarium oxysporum* strains isolated previously in the art. Previously isolated *Fusarium oxysporum* strains have been described (see Naim et al., 1985, Bhatia et al., 2006, and Naqvi et al, 1997). In one embodiment, the isolated strain can convert feedstock to lipids at a rate of at least 0.04 g lipid/g feedstock, 0.05 g lipid/g feedstock, 0.06 g lipid/g feedstock, 0.07 g lipid/g feedstock, 0.08 g lipid/g feedstock, 0.1 g lipid/g feedstock, 0.12 g lipid/g feedstock, 0.14 g lipid/g feedstock, 0.16 g lipid/g feedstock, 0.18 g lipid/g feedstock, 0.2 g lipid/g feedstock, 0.25 g lipid/g feedstock, 0.3 g g lipid/g feedstock, 0.35 g lipid/g feedstock, or 0.4 g lipid/g feedstock, after 10 days incubation at pH 2.5 under aerobic conditions.

In one embodiment, the isolated fungal strain of the present invention produces a more favorable lipid profile compared to previously isolated fungi or microalgae. For example, the isolated strain produces more saturated fatty acids (e.g., palmitic (16:0) and stearic acids (18:0)) and mono-unsaturated fatty acids (e.g. oleic acid (18:1)), but less polyunsaturated fatty acids which are more vulnerable to oxidation.

In some embodiments, said isolated fungal strain and/or its progeny can grow at a high metal concentration, wherein the metal is selected from the group consisting Mn, Ag, Zn, Fe, Al, Be, Pb, Cu, Cr, Ni, Cd, Co, Ni, Pd, Pt, U, Th, Mo, Sn, Ti, As, Au, Se, Sb and Hg. In one embodiment, the isolate fungal strain can grow well with a high Mn concentration up to 25 mM. In one embodiment, two or more such heavy metal(s) (or heavy metals taken collectively) may be present at more than 0.1 ppm, or 1 ppm, or 10 ppm, or 50 ppm, or 100 ppm, or 200 ppm, or 400 ppm, or 500 ppm, or 1000 ppm, or 5000 ppm, or 10,000 ppm, or 50,000 ppm, or 100,000 ppm, by weight.

The isolated *Fusarium oxysporum* strain and/or its progeny of the present invention can be cultured in the absence of antibiotics with little or no contaminations, wherein said contaminations by other organisms are selected from the group consisting of contaminations by bacteria, other fungi (e.g., yeasts, molds), algae, plants, insects, and mixture thereon.

The isolated *Fusarium oxysporum* strain and/or its progeny can be further modified, for example, by mutagenesis, and/or recombinant technologies (e.g., transformation). Methods of fungal mutagenesis and recombinant technologies are well known in the art. Classical mutagenesis methods can be applied, which include, but are not limited to, chemical mutagenesis, insertional mutagenesis, and radiation mutagenesis (e.g., UV or gamma irradiation). In some cases, genetic crosses can be done to combine improvements from different mutants.

In one embodiment of the present invention, the isolated fungal strain and/or its progeny is capable of high density cell growth. In some embodiments of the present invention, the microorganisms are capable of achieving a cell density of at least about 10 g/L, at least about 15 g/L, at least about 20 g/L, at least about 25 g/L, at least about 30 g/L, at least about 50 g/L, at least about 75 g/L, at least about 100 g/L, at least about 125 g/L, at least about 135 g/L, at least about 140 g/L, at least about 145 g/L, or at least about 150 g/L. For example, the isolated fungal strain is capable of achieving a cell density of from about 10 g/L to about 300 g/L, from about 15 g/L to about 300 g/L, from about 20 g/L to about 300 g/L, from about 25 g/L to about 300 g/L, from about 30 g/L to about 300 g/L, from about 50 g/L to about 300 g/L, from about 75 g/L to about 300 g/L, from about 100 g/L to about 300 g/L, from about 125 g/L to about 300 g/L, from about 130 g/L to about 290 g/L, from about 135 g/L to about 280 g/L, from about 140 g/L to about 270 g/L, from about 145 g/L to about 260 g/L, from about 150 g/L to about 250 g/L, or from about 100 g/L to about 280 g/L. The high density growth of the isolated fungal strain of the present invention can be increased by adjusting the fermentation conditions (such as temperature, pH, concentration of ions, and gas concentrations).

Genes and Proteins of the Isolated Fungal Strain

Proteins (e.g., certain enzymes) of the wild-type isolated *Fusarium oxysporum* strain MK7 and/or its progeny can be purified. Methods of protein purification are known to one skilled in the art. Detailed protein purification methods have been described in Janson and Ryden (*Protein purification: principles, high-resolution methods, and applications*; Wiley-VCH, 1998, ISBN 0471186260, 9780471186267), Deutscher (*Guide to protein purification, Volume* 182 *of Methods in enzymology*, Gulf Professional Publishing, 1990, ISBN 0121820831, 9780121820831), and Cutler (*Protein purification protocols, Volume* 244 *of Methods in molecular biology*, Humana Press, 2004 ISBN 1588290670, 9781588290670), which are incorporated by reference in their entireties for all purposes.

Nucleotide sequences of the isolated fungal strain and/or its progeny of the present invention can be cloned, sequenced, characterized and modified through biotechnology. Cloned sequences can be transferred to another organism.

Non-limiting example of methods of DNA extraction from *Fusarium oxysporum* and methods of DNA sequence analyses (e.g., PCR, AFLP, SSR and DNA sequence analyses, southern blot, RT-PCT, et al.) have been demonstrated by Lee et al. (1990, Isolation of DNA from fungal mycelia and single spores, Academic Press, New York, pp. 282-287), Gale et al. (2003, *Phytopathology* 93:1014-1022), Bogale et al. (2006, Characterization of *Fusarium oxysporum* isolates from Ethiopia using AFLP, SSR and DNA sequence analyses, Fungal Diversity, 23:51-65). In addition, biological materials, experimental procedures that can be used for growing *Fusarium oxysporum*, RNA isolation, cDNA library construction, microarray preparation and microarray data analysis techniques have been described by Dowd et al (2004, Gene expression profile changes in cotton root and hypocotyl tissues in response to infection with *Fusarium oxysporum* f sp. *vasinfectum. Mol. Plant-Microbe Interact.* 17:654-667).

General texts which describe molecular biological techniques, which are applicable to the present invention, such as cloning, mutation, and the like, include Berger and Kimmel, Guide to Molecular Cloning Techniques, Methods in Enzymology, Vol. 152 Academic Press, Inc., San Diego, Calif. ("Berger"); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating the present genes etc. Thus, the invention also encompasses using known methods of protein engineering and recombinant DNA technology to improve or alter the characteristics of the proteins expressed in by *Fusarium* strains (e.g. strain MK7). Various types of mutagenesis can be used to produce and/or isolate variant nucleic acids that encode for protein molecules and/or to further modify/mutate the proteins of the present invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Methods of cloning genes are known in the art. The gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

In one embodiment, the genes encoding certain enzymes are cloned by expression cloning (a.k.a. activity cloning). For example, the isolated *Fusarium oxysporum* strain MK7 is propagated, and cDNA libraries are made using polyadenine mRNA extracted from strain MK7. Expression vectors in the cDNA libraries are then transformed into suitable host cells (e.g., fungal cells, bacteria cells, yeast cells, plant cells, insect cells, and animal cells) and said host cells are screened for preferred enzymatic activity. In one embodiment, said enzymatic activity is selected from the group consisting of enzymatic activities of cellulase, xylanase, ligninase, glucuronidase, arabinofuranosidase, arabinogalactanase, ferulic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase, xylosidase, α-L-arabinofuranosidase, feruloyl esterase, endoglucanase, β-glucosidase, Mn-peroxidase, and laccase.

In another embodiment, since the genome sequence of *Fusarium oxysporum* is available, a genomics/bioinformatics method can be taken to clone genes encoding enzymes of interest. For example, data mining the genome sequence of *Fusarium oxysporum* for homologs of genes of interest can reveal candidate genes encoding protein with certain preferred enzymatic activities. Then such genes can be cloned and tested for the activities.

Still in another embodiment, genes encoding protein with certain preferred enzymatic activities can be isolated by traditional molecular cloning methods. For example, activities of certain proteins can be identified from a culture bank, and said proteins can be purified. The purified enzymes are then subjected to analysis, and the peptide sequences can be determined. Degenerate primers are then designed, and used in a PCR or a RT-PCR to clone the genes of interest. To design the degenerate primers, known homologous amino acid sequences can be aligned with the protein of interest to identify conserved regions.

The isolated gene encoding an acid pH tolerant enzyme be cloned into an expression vector, and transformed into a host cell selected from the group consisting of fungal cell (e.g., *Fusarium* species, *Aspergillus* species), bacteria cell (e.g., *bacillus* species), yeast cell, plant cell, insect cell, and animal cell. To select a suitable host cell, several factors need to be considered: the speed of cell growth, cost of growth medium, expression levels, secretion capability, and post-translational modifications (e.g., protein folding, N-linked glycosylation, O-linked glycosylation, phosphorylation, acetylation and acylation).

In one embodiment, said gene encoding an acid pH tolerant enzyme is transformed into a fungal cell. Normally, a fungal strain which has (1) low secreted protease levels, (2) low total spectrum of secreted proteins, (3) capacity for high level heterologous expression, (4) favorable fermentation morphology, (5) "Generally Regarded As Safe" status, and (6) transformability, is preferred for expression. Methods of transformation of filamentous fungi are well known in the art. In one embodiment, the transformation is through bombardment (see, Aboul-Soud et al., Transformation of *Fusarium oxysporum* by particle bombardment and characterization of the resulting transformants expressing a GFP transgene, January 2005, Mycopathologia, 158(4):475-482). In another embodiment, the transformation is Agrobacteria-mediated (see, Mullins et al., *Agrobacterium*-mediated transformation of *Fusarium oxysporum*: an efficient tool for insertional mutagenesis and gene transfer, 2001, Phytopathology, 91(2):173-180). In still another embodiment, said transformation is chemical-mediated (e.g., polyethylene glycol (PEG) mediated protoplast transformation, see, Powell et al., *Journal of Bacteriology, June* 1990, 172(6):3163-3171). For example, conidia (spores) of fungal host are germinated to make young germling mycelia first. Subsequently, cell wall of mycelia is removed by lytic enzyme mixture to form fungal protoplasts, which is osmotically fragile. Said fungal protoplasts are mixed with DNA (encoding a selectable marker), $CaCl_2$ and PEG, and optionally, nuclease inhibitor (e.g., aurintricarboxylic acid). Dilutions of the protoplasts were then spread on osmotically-stabilized medium (e.g., minimal medium containing sucrose) to allow regeneration and selection of transformants A typical expression vector used in fungal host cell comprises a fungal promoter (which allows initiation of transcription in a fungal host), the gene of interest, a fungal terminator (which ensures termination of transcription in a fungal host), and a selectable marker. Translation initiation signals and DNA encoding signal peptide for secretion can also be included. The selection marker can be selected from the group consisting of nutritional markers (e.g., argB (arginine prototrophy) and trpC (trptophan prototrophy)), nutritional markers with forward and reverse selection (e.g., amdS (acetamidase), pyrG (uridine prototrophy), niaD (nitrate utilization), and sC (sulphate utilization)), and dominant selectable markers (e.g., benA (benomyl-resistant β-tubulin), oliC (oligomycin-resistant ATP synthase), hygB (hygromycin B resistance), G418

(geneticin resistance), phleomycin/bleomycin resistance, bar (confers resistance to BASTA (herbicide)). Non-limiting examples of fungal expression vectors are pBARKS, pBAR-GEM, pBARMTE, pBARGP, pAn52-7Not uidA, pPFE2, p777, pAN, pTL, pUC19, and those described in Cullen et al. (Molecular Cloning Vectors for *Aspergillus* and *Neurospora*, in A Survey of Molecular Cloning Vectors and Their Uses, Butterworth Publishers, Stoneham, M A 1986). Transformation of fungal hosts is integrative, and is usually mitotically stable.

Fungal expression systems can be optimized. For example, major secreted host proteins can be deleted so that the heterologous enzyme constitutes a high percentage of total protein. Genes encoding proteases and mucotoxins can also be deleted to stabilize expressed protein and unwanted side activity. In addition, constitutive/induced promoter, hotspots included in expression vectors, ectors, Kozak sequence optimization, manipulation of different binding sites in promoter can all be used.

The isolated fungal strain and/or its progeny of the present invention can be further mutagenized and screened for improved expression or for the removal of one or more unwanted side-activities. Classical mutagenesis methods can be applied, which include, but are not limited to, chemical mutagenesis, insertional mutagenesis, and radiation mutagenesis (e.g., UV or gamma irradiation). In some cases, genetic crosses can be done to combine improvements from different mutants.

Production of Biofuel and/or Precursors of Biofuel

Biofuels produced from sugar, starch, vegetable oil, or animal fats using conventional technology are called first-generation biofuels. The basic feedstocks for these biofuels are often seeds/grains containing starch (e.g. wheat, corn) or vegetable oil (e.g. sunflower), which only represent small portions of whole plants. Due to the rising global population, feedstocks for producing biofuels have been criticized for diverting food away from human and animal food chain, leading to food shortages and price rises.

The second generation biofuel (e.g. cellulosic biofuels, biohydrogen, biomethanol, DMF, Bio-DME, Fischer-Tropsch diesel, biohydrogen diesel, mixed alcohols and wood diesel), which can be produced from non food crops, or non-edible parts of crops, including but not limited to, waste biomass, stalks of wheat, corn, wood, and special biomass crops (e.g. *Miscanthus*), is more publicly and politically popular. Among these, cellulosic ethanol is a type of biofuel produced from lignocellulose, a structural material that comprises much of the biomass of plants. It is composed mainly of cellulose (31-49%), hemicellulose (16-26%) and lignin (19-26%). Lignin makes the plant rigid and resistant to compression and must be removed before fermentation. Crop stover (e.g., leaves and stalks of corn, sorghum, soybean, et al.), Switchgrass, *Miscanthus*, woodchips and the byproducts of lawn and tree maintenance are some of the more popular cellulosic materials for ethanol production. Production of cellulosic ethanol requires extra steps of processing raw materials to release the sugar monomers for microorganisms fermentation from lignin. Compared to first generation biofuel, lignocellulose-based biofuels have several advantages. Firstly, sources for lignocellulose-based biofuels are geographically more evenly distributed than sugars/starch-based biofuels. Secondly, lignocellulosic raw materials minimize the potential conflict between land use for food (and feed) production and energy feedstock production. The raw material is less expensive than conventional agricultural feedstock and can be produced with lower input of fertilizers, pesticides, and energy. Thirdly, biofuels from lignocellulose generate low net greenhouse gas emissions, reducing environmental impacts, particularly climate change.

Generally, the feedstock will contain organic and inorganic nutrients for supporting the growth and metabolism of the isolated fungal strain. However, where necessary inorganic or organic nutrients are absent, or are present in insufficient amounts, the feedstock may be supplemented with an aqueous phase containing said necessary inorganic or organic nutrients to support fungal growth and metabolism.

Bioalcohols

In one embodiment, the present invention provides methods of producing bioalcohols and/or precursors of bioalcohols from feedstocks using the isolated fungal strain of the present invention. Non-limiting exemplary bioalcohols produced are bioethanol, biomethanol, biobutanol, isobutanol, et al. In one embodiment, the bioalcohol is bioethanol.

In one embodiment, said bioalcohols are produced in fermentation under anaerobic conditions. In another embodiment, said bioalcohols are produced in fermentation under substantially anaerobic conditions.

Non-limiting examples of feedstocks include, ligno-cellulosic feedstocks, carbon containing waste products, carbohydrates, or a combination thereof. For example, lignocellulosic feedstocks are selected from the group consisting of agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), lignocellulosic containing waste (e.g., newsprint, waste paper, brewing grains, used rubber tire (UTR), municipal organic waste, yard waste, clinical organic waste, waste generated during the production of biofuels (e.g. processed algal biomass, glycerol), and a combination thereof. The carbohydrates are selected from the group consisting of monosaccharides, disaccharides, oligosaccharides, polysaccharides, and mixture thereof. For example, the carbohydrates are five and six carbon sugars.

Methods and strategies for the production of commodity biofuel and/or precursors of biofuel and chemicals from feedstocks are known in the art. Major steps of producing cellulosic alcohols include pretreatment (making the lignocellulosic material such as wood or straw amenable to hydrolysis), cellulolysis (breaking down the molecules into sugars), separation (mainly isolating sugar solution from lignin), fermentation and distillation. Pretreatment techniques include acid hydrolysis, steam explosion, ammonia fiber expansion, alkaline wet oxidation and ozone pretreatment (Klinke et al., 2004, Inhibition of ethanol-producing yeast and bacteria by degradation products produced during pre-treatment of biomass. *Appl Microbiol Biotechnol* 66:10-26.).

A fermenter (also called a bioreactor) is can be used as a container for the production of biofuel. The first step of fermentation is to sterilize the fermenter. Sterilization can be done with steam, chemicals, washing, or combination of these. Numerous reactor designs have been reported, such as batch reactors, sequencing batch reactors, continuously stirred tank reactors, anaerobic contact reactors, anaerobic baffled reactors, fluidized-bed reactors, gas lift reactors, upflow anaerobic sludge blanket reactors and anaerobic hybrid reactors. Illustrative fermenters are those described in U.S. Pat. Nos. 3,615,253; 5,205,936; 5,728,577; 4,530,762; 4,649,117; 7,446,156 and 5,228,995. According to different fermenters, there are three general ways in which fermentations are done: batch fermentation, fed batch fermentation (or continuous fermentation) and cascade fermentation. For batch fermentation, the reactor is filled with sterile substrate and inoculated with fermentation organism. The culture is allowed to grow until saturation. For fed batch fermentation (or continuous fermentation), substrate is fed continuously and the culture medium is removed continuously. For cascade fermentation, the fermenting 'liquor' is passed through a series of ferments to built up more and more products (e.g. in brewing, the beer would be fermented in several stages to increase the alcohol content.).

The fermentation is started with the inoculation of a small, actively growing sample of the microorganism to the fermenters (bioreactors) containing sterile substrate. Both prokaryotic microorganisms (including bacteria, cyanobacteria) and eukaryotic microorganisms (including yeast, fungi and algae) have been used in industrial fermentation. In some other bioreactors, alternative organisms (including plant cells, mammalian cells) are used to produce products such as proteins, especially for pharmaceutical purposes. For instance, cell cultures of several different plant species, including *Arabidopsis thaliana, Taxus cuspidata, Catharathus roseus* and important domestic crops such as tobacco, alfalfa, rice, tomato and soybean, are used for recombinant protein manufacture.

Microorganisms are used extensively to produce a great range of products and service: such as traditional products (including but not limited to, bread, beer, wine, spirits, cheese, dairy products, fermented meats and vegetables, mushrooms, soy sauce and vinegar), agricultural products (including but not limited to, gibberellins, fungicides, insecticides, silage, amino acids such as L-Glutamine, L-Lysine, L-Tryptophan, L-Throenine, L-aspartic (+), L-arylglycines), enzymes (including but not limited to, carbohydrates, celluloses, lipases, pectinases, proteases), fuels and chemical feedstocks (including but not limited to, acetone, butanol, butanediol, isopropanol, ethyl alcohol, glycerol, methane, glycerol, butyric acid, methane, citric acid, fumaric acid, lactic acid, propionic acid, succinic acid, itaconic acid, acetic acid, 3-hydroxypropionic acid, glyconic acid, tartaric acid and L-glutaric acid or salts of any of these acids), nucleotides, organic acids, pharmaceuticals and related compounds (including but not limited to, alkaloids, antibiotics, hormones, immunosuppressant, interferon, steroids, vaccines, vitamins) and polymers (including but not limited to, alginates, dextran, gellan, polyhydroxybutyrate, scleroglucan and xanthan).

Cellulolysis are currently performed by choosing from chemical hydrolysis (e.g. U.S. Pat. Nos. 4,427,453; 4,556,430; 6,022,419), enzymatic hydrolysis (e.g. U.S. Pat. No. 5,637,502) and thermal hydrolysis (e.g. U.S. Pat. No. 6,692,578). Diluted acid is used under high heat and high pressure in the chemical hydrolysis (or concentrated acid at lower temperatures and pressure) to breakdown polysaccharide chains. Cellulase, xylanase and hemicellulase, which can be produced from fungi (*Trichoderma reesei*) at large amount (e.g. U.S. Pat. No. 6,555,335), are used to convert biomass such as corn stover, distiller grains, wheat straw and sugar cane bagasse, or energy crops (e.g. Switchgrass) into fermentable sugars. In the fermentation step, baker's yeast (*Saccharomyces cerevisiae*) has been used in industrial production of ethanol from hexoses (6-carbon sugar). Processes for the continuous fermentation of sugars to provide alcohol and ethanol fermentation processes featuring yeast recycle are known (viz., U.S. Pat. Nos. 1,201,062; 2,054,736; 2,063,223; 2,122,939; 2,146,326; 2,169,244; 2,230,318; 2,272,982; 2,285,130; 2,155,134; 2,371,208; 2,657,174; 2,676,137; 2,967,107; 3,015,612; 3,078,166; 3,093,548; 3,177,005; 3,201,328; 3,207,605; 3,207,606; 3,219,319; 3,234,026; 3,413,124; 3,528,889; 3,575,813; 3,591,454; 3,658,647; 3,676,640; 3,705,841; 3,737,323; 3,940,492; and, 3,984,286).

Ligno-cellosic materials comprise cellulose, hemicellulose and lignin. Cellulose is a polysaccharide comprising glucopyranose subunits joined by β-1→4 glucosidic bonds. The monomer subunits are glucose. Hemicellulose are groups of polysaccharides including four basic types: D-xyloglucans, D-xylans, D-mannans, and D-galactans. In each type, two to six monomers are linked by β-1→4 and β-1→3 bonds in main chained and α-1→2, 3, and 6 binds in branches. The monomer subunits can be D-xylose, L-arabinose, D-mannose, D-glucose, D-galactose, and D-glucouronic acid. Core lignins are highly condensed polymers formed by dehydrogenative polymerization of the hydroxycinnamyl alcohols, p-coumaryl alcohols, coniferyl alcohols, and sinapyl alcohols. Non-core lignin includes esterified or etherified phenolic acids bound to core lignin or noncellulosic polysaccharides. In preferred embodiments, the biomass material comprising cellulose, hemicellulose and lignin (i.e., lignocellulosic biomass) is treated to produce glucose, fructose, sucrose, mannose, maltose, sorbitol, galactose, xylose, and combinations thereof.

In some embodiments, ligno-cellulosic biomass materials are hydrolyzed before fermentation. The present invention is not limited to the use of any particular hydrolysis method. Indeed, the use of a variety of hydrolysis methods are contemplated, including, but not limited to, enzymatic hydrolysis and chemical hydrolysis (such as dilute acid hydrolysis or concentrated acid hydrolysis) and combinations thereof.

Some examples of methods of pretreating feedstock are disclosed in patent application publication nos. U.S. 2007/0161095, WO 05/053812, WO 06/086757, U.S. 2006/0182857, U.S. 2006/177551, U.S. 2007/0110862, WO 06/096834, WO 07/055735, U.S. 2007/0099278, WO 06/119318, U.S. 2006/0172405, and U.S. 2005/0026262.

Examples of enzymes suitable for digestion of cellulose are disclosed in patent or patent application publication nos. U.S. 2003/0096342, WO 03/012109, U.S. Pat. No. 7,059,993, WO 03/012095, WO 03/012090, U.S. 2003/0108988, U.S. 2004/0038334, U.S. 2003/0104522, EP 1 612 267, and WO 06/003175.

The isolated fungal strain and/or its progeny of the present invention directly can convert ligno-cellulosic feedstocks to energy-rich metabolites with few pretreatment steps and no enzyme additions. Consequently, use of this novel process is relatively simple and inexpensive in comparison to current methods. However, it is understood that the pretreatment steps and enzymes additions can still be employed as optional steps to increase hydrolysis rates and reduce production time of energy-rich metabolites.

Biodiesel and Biolubricant

Biodiesel refers to lipid-based diesel fuel consisting of long-chain alkyl (methyl, propyl or ethyl) esters, wherein the lipid comes from living or recently living organisms (e.g., vegetables oil, animal fat, microorganisms oil). Lipids may be employed as precursors in the production of biodiesels, for example, by transesterification. As used herein, the term transesterification refers to the process of exchanging the organic group R" of an ester with the organic group R' of an alcohol:

These reactions are often catalyzed by the addition of an acid or base. Biodiesel is typically made by chemically reacting lipids (e.g., vegetable oil, animal fat) with an alcohol. Non-limiting examples of alcohols include, methanol, ethanol, butanol, isopropanol. Using alcohols of higher molecular weights improves the cold flow properties of the resulting ester, at the cost of a less efficient transesterification reaction. Any free fatty acids (FFAs) in the base oil are either converted to soap and removed from the process, or they are esterified (yielding more biodiesel) using an acidic catalyst. A by-product of the transesterification process is the production of glycerol.

Lipids as precursors of biodiesel can come from a lot of feedstock sources. Non-limiting examples of feedstocks include, rapeseed oil, soybean oil, field pennycress, jatropha, mustard, flax, sunflower, palm oil, coconut, hemp, castor oil, coconut oil, corn oil, cottonseed oil, peanut oil, radish oil, ramtil oil, rice bran oil, safflower oil, salicornia oil, sunflower oil, tung oil, algae oil, copaiba, honge oil, jatropha oil, jojoba oil, milk bush, petroleum nut oil, and animal fat.

Biodiesel is meant to be used in standard diesel engines and is thus distinct from the vegetable and waste oils used to fuel converted diesel engines. Biodiesel can be used alone, or blended with petro-diesel. Blends of biodiesel and conventional hydrocarbon-based diesel are products most commonly distributed for use in the retail diesel fuel marketplace. Blends of 20 percent biodiesel with 80 percent petroleum diesel (B20) can generally be used in unmodified diesel engines. Biodiesel can also be used in its pure form (B100), but may require certain engine modifications to avoid maintenance and performance problems.

Biodiesel can also be used as a heating fuel in domestic and commercial boilers, a mix of heating oil and biofuel which is standardized and taxed slightly differently than diesel fuel used for transportation. It is sometimes known as "bioheat". Heating biodiesel is available in various blends; up to 20% biofuel is considered acceptable for use in existing furnaces without modification.

Non-limiting examples of biodiesel production methods include, batch process, enzyme-free supercritical process, ultra- and high-shear in-line and batch reactor method, ultrasonic-reactor method and microwave method. More systems and apparatus for biodiesel production are described in U.S. Pat. Nos. 7,452,515, 7,524,982, 7,420,072, 6,824, 682, 7,169,821, 6,979,426, 7,514,247, 7,449,313, 7,605,281, and U.S. Patent Application Nos. 20080282606, 20070260079, 20070010681, 20090054701, 20030111410, 20080202021, 20050113467, 20050255013, 20030175182, 20080299633, 20080102503, 20090178330, 20080313955, 20080282687, 20070167642, and 20070122667, each of which is hereby incorporated by reference in its entirety.

Thus, the present invention provides methods of producing energy-rich metabolites using the isolated fungal strain of the present invention, wherein the energy-rich metabolites are essentially lipids as precursors of biodiesel. The lipids can be extracted from the isolated fungal strains for production of biodiesel. The isolated fungal strain of the present invention has a more favorable lipid profile in comparison to algae and other lipid producing organisms. In one embodiment, said lipids are essentially fatty acids. In one embodiment, said fatty acids are essentially unsaturated fatty acids and/or saturated fatty acids. In one embodiment, said unsaturated fatty acids are selected from the group consisting of oleic acid (18:1), α-linolenic acid (18:3), eicosenoic acid (20:1), and a combination thereof. In one embodiment, said saturated fatty acids are selected from the group consisting of palmitic acids (16:0), stearic acids (18:0), arachidic acid (20:0), behenic acid (22:0), and any and all combinations thereof. Other types of lipids that may be produced include, but are not limited to, saturated fats (e.g. butyric acid, hexanoic acid, octanoic acid, decanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, docosanoic acid, tetracosanoic acid), Monounsaturated fats (e.g., tetradecenoic acid, pentadecenoic acid, hexadecenoic acid, heptadecenoic acid, octadecenoic acid, eicosenoic acid, docosenoic acid, cis-tetracosenoic acid), and polyunsaturated fats (e.g. hexadecadienoic aid, linoleic acid, linolenic acid, alpha-linolenic acid, gamma-linolenic acid, parinaric acid, eicosadiencoic acid, arachidonic acid, timnodonic acid, brassic acid, clupanodonic acid and docosahexaenoic acid), omega-7 vaccenic acid (Methyl 11-octadecenoate), omega-7 palmitoleic acid (methyl hexadec-9-enoate; trade name Provinal™) and tetracosanoic acid, methyl ester, and other fatty acids listed in Table 1.

In one embodiment, said lipids as precursors of biodiesel are produced in fermentation under aerobic conditions. In another embodiment, said bioalcohols are produced in fermentation under substantially aerobic conditions.

In one embodiment, the isolated fungal strain and/or its progeny is capable of efficient production of the lipids. In some embodiments of the present invention, the amount of lipids produced is at least about 1 g/L/day, 5 g/L/day, at least about 10 g/L/day, at least about 20 g/L/day, at least about 30 g/L/day, at least about 40 g/L/day, at least about 50 g/L/day, at least about 60 g/L/day, at least about 70 g/L/day, or more. For example, the amount of biological oil produced is from about 1 g/L/day to about 5 g/L/day, from about 5 g/L/day to about 70 g/L/day, from about 10 g/L/day to about 70 g/L/day, from about 20 g/L/day to about 70 g/L/day, or from about 30 g/L/day to about 70 g/L/day.

Lipids in a sample can be extracted using different procedures. Non-limiting examples of lipids extraction are described in King et al. (Supercritical Fluid Extraction: Present Status and Prospects, 2002, *Grasa Asceites*, 53, 8-21), Folch et al. (A simple method for the isolation and purification of total lipids from animal tissues, 1957, *J. Biol. Chem.*, 226, 497-509), Bligh and Dyer (A rapid method of total lipid extraction and purification. 1959, *Can. J. Biochem. Physiol.*, 37, 911-917), Cabrini et al. (Extraction of lipids and lipophilic antioxidants from fish tissues—a comparison among different methods. 1992, *Comp. Biochem. Physiol.*, 101B, 383-386), Hara et al. (Lipid extraction of tissues with a low toxicity solvent. 1978, *Anal. Biochem.*, 90, 420-426), Lin et al. (Ethyl acetate/ethyl alcohol mixtures as an alternative to Folch reagent for extracting animal lipids. 2004, *J. Agric. Food Chem.*, 52, 4984-4986), Whiteley et al. (Lipid peroxidation in liver tissue specimens stored at sub-zero temperatures. 1992, Cryo-Letters, 13, 83-86), Kramer et al. (A comparison of procedures to determine free fatty acids in rat heart. 1978, *J. Lipid Res.*, 19, 103-106) and Somashekar et al. (Efficacy of extraction methods for lipid and fatty acid composition from fungal cultures, 2001, *World Journal of Microbiology and Biotechnology*, 17(3): 317-320). In another example, lipid can be extracted by methods similar to the FRIOLEX® (Westfalia Separator Industry GmbH, Germany) process is used to extract the biological oils produced by the microorganisms. FRIOLEX® is a water-based physical oil extraction process, whereby raw material containing oil can be used directly for extracting oil without using any conventional solvent extraction methods. In this process, a water-soluble organic solvent can be used as a process aid and the oil is separated from the raw material broth by density separation using gravity or centrifugal forces.

After the lipids have been extracted, the lipids can be recovered or separated from non-lipid components by any suitable means known in the art. For example, low-cost physical and/or mechanical techniques are used to separate the lipid-containing compositions from non-lipid compositions. If multiple phases or fractions are created by the extraction method used to extract the lipids, where one or more phases or fractions contain lipids, a method for recovering the lipid-containing phases or fractions can involve physically removing the lipid-containing phases or fractions from the non-lipid phases or fractions, or vice versa. In some embodiments of the present invention, a FRIOLEX® type method is used to extract the lipids produced by the microorganisms and the lipid-rich light phase is then physically separated from the protein-rich heavy phase (such as by skimming off the lipid-rich phase that is on top of the protein-rich heavy phase after density separation).

In some embodiments of the present invention, the lignocellulosic feedstock that is used to grow the isolated fungal strain comprises cellulose in an amount of from about 5% to about 100%, from about 10% to about 95%, from about 20% to about 90%, from about 30% to about 85%, from about 40% to about 80%, from about 50% to about 75%, or from about 60% to about 70% by dry weight of the carbon feedstock. In some embodiments of the present invention, the cellulosic feedstock comprises cellulose in an amount of at least about 5%, at least about 10%, at least about 20%, at least about 30%, at least about 40%, at least about 50%, at least about 60%, or at least about 70% of the dry weight of the carbon feedstock. In some embodiments of the present invention, the cellulosic feedstock used to grow the isolated fungal strain comprises from about 1% to about 50%, from about 5% to about 40%, or from about 10% to about 30% by weight of a component selected from lignin, hemicellulose, or a combination thereof. In some embodiments of the present invention, the cellulosic feedstock used to grow a microorganism comprises at least about 1%, at least about 5%, at least about 10%, at least about 20%, or at least about 30% by weight of a component selected from lignin, hemicellulose, or a combination thereof.

There are at least two stages in the production of lipids using the isolated fungal strain: biomass accumulation stage and lipid production stage. In some embodiments of the present invention, the biomass accumulation stage produces biomass of the fungal strain such that about 10% to about 95%, about 20% to about 95%, about 30% to about 95%, about 40% to about 95%, or about 50% to about 95% of the total biomass production of the fungal strain is achieved during the biomass accumulation stage. In further embodiments of the present invention, about 60% to about 95%, about 70% to about 95%, or about 80% to about 95% of the total biomass production of the microorganism is achieved during the biomass accumulation stage. In some embodiments of the present invention, the biomass accumulation stage produces biomass of the microorganism such that at least about 10%, at least about 20%, at least about 30%, at least about 40%, at least about 50%, at least about 60%, at least about 70%, at least about 80%, at least about 90%, or at least about 95% of the total biomass production of the microorganism is achieved during the biomass accumulation stage. For example, about 50% to about 95% of the total biomass production of the microorganism is achieved during the biomass accumulation stage. In some embodiments of the present invention, the lipid accumulation stage produces lipids such that about 10% to about 95%, about 20% to about 95%, about 30% to about 95%, about 40% to about 95%, or about-50% to about 95% of the total lipid production of the microorganism is achieved during the lipid accumulation stage. In further embodiments of the present invention, about 60% to about 95%, about 70% to about 95%, or about 80% to about 95% of the total lipid production of the microorganism is achieved during the lipid accumulation stage. In some embodiments of the present invention, the lipid accumulation stage produces lipids such that at least about 10%, at least about 20%, at least about 30%, at least about 40%, at least about 50%, at least about 60%, at least about 70%, at least about 80%, at least about 90%, or at least about 95% of the total lipid production of the microorganism is achieved during the lipid accumulation stage. Preferably, about 50% to about 95% of the total lipid production of the microorganism is achieved during the lipid accumulation stage.

Once the lipids are produced in accordance with the present invention, various methods known in the art can be used to transform the biological oils into esters of fatty acids for use as biodiesel, jet biofuel, or as ingredients for food or pharmaceutical products. In some embodiments of the present invention, the production of esters of fatty acids comprises transesterifying the biological oils produced by the microorganism. In some embodiments of the present invention, the extraction of the lipids from the microorganisms and the transesterification of the lipids can be performed simultaneously, in a one step method. For example, the culture containing the isolated fungal strain can be exposed to conditions or treatments (or a combination of conditions or treatments) that promote both extraction of the lipids and the transesterification of the lipids. Such conditions or treatments could include, but are not limited to, pH, temperature, pressure, the presence of solvents, the presence of water, the presence of catalysts or enzymes, the presence of detergents, and physical/mechanical forces. Two sets of conditions or treatments could be combined to produce a one step method of extracting and transesterifying the lipids, where one set of conditions or treatments favorably promotes extraction of the lipids and the other set of conditions or treatments favorably promotes transesterification of the lipids, so long as the two sets of conditions or treatments can be combined without causing significant reduction in the efficiency of either the extraction or the transesterification of the lipids. In some embodiments of the present invention, hydrolysis and transesterification can be performed directly of whole-cell biomass. In other embodiments of the present invention, the extraction of the lipids is performed as a step that is separate from the step of transesterification of the lipids. In one embodiment, such transesterification reactions are performed using acid or base catalysts. In some embodiments of the present invention, methods for transesterifying the biological lipids into esters of fatty acids for use as biodiesel or as ingredients for food or pharmaceutical products involve reacting the biological oils containing triglycerides in the presence of an alcohol and a base to produce esters of the fatty acid residues from the triglycerides.

Alcohols suitable for use in transesterification include any lower alkyl alcohol containing from 1 to 6 carbon atoms (i.e., a C 1-6 alkyl alcohol, such as methyl, ethyl, isopropyl, butyl, pentyl, hexyl alcohols and isomers thereof). Without being bound by theory, it is believed that in some embodiments of the present invention, the use of lower alkyl alcohols in the methods of the present invention produces lower alkyl esters of the fatty acid residues. For example, the use of ethanol produces ethyl esters. In certain embodiments, the alcohol is methanol or ethanol. In these embodiments, the fatty acid esters produced are a methyl ester and an ethyl ester of the fatty acid residue, respectively. In processes of the present invention, the alcohol typically comprises from about 5 wt. % to about 70 wt. %, from about 5 wt. % to about 60 wt. %, from about 5% to about 50 wt. %, from about 7 wt. % to about 40 wt. %, from about 9 wt. % to about 30 wt. %, or from about 10 wt. % to about 25 wt. % of the mixture of the lipids composition, the alcohol and the base. In certain embodiments, the composition and the base can be added to either pure ethanol or pure methanol. In general, the amount of alcohol used may vary with the solubility of the lipids or composition containing triglycerides in the alcohol.

The composition comprising triglycerides, the alcohol and the base are reacted together at a temperature and for an amount of time that allows the production of an ester from the fatty acid residues and the alcohol. Suitable reaction times and temperatures may be determined by one of skill in the art to produce an ester. Without intending to be bound by theory, the fatty acid residues are believed to be cleaved from the glycerol backbone of the triglyceride and esters of each fatty acid residue are formed during the step of reacting. In certain embodiments, the step of reacting the composition in the presence of an alcohol and a base is performed at a temperature from about 20° C. to about 140° C., from about 20° C. to about 120° C., from about 20° C. to about 110° C., from about 20° C. to about 100° C., or from about 20° C. to about 90° C. In further embodiments, the step of reacting the composition in the presence of an alcohol and a base is performed at a temperature of at least about 20° C., 75° C., 80° C., 85° C., 90° C. 95° C., 105° C., or 120° C. In some embodiments of the present invention, the step of reacting the composition in the presence of an alcohol and a base is performed at a temperature of about 20° C., 75° C., 80° C., 85° C., 90° C., 95° C., 105° C., or 120° C. In some embodiments, the step of reacting the composition in the presence of an alcohol and a base is performed for a time from about 2 hours to about 36 hours, from about 3 hours to about 36 hours, from about 4 hours to about 36 hours, from about 5 hours to about 36 hours, or from about 6 hours to about 36 hours. In certain embodiments, the step of reacting the composition in the presence of an alcohol and a base is performed for about 0.25, 0.5, 1.0, 2.0, 4.0, 5.0, 5.5, 6, 6.5, 7, 7.5, 8, 8.5, 10, 12, 16, 20, 24, 28, 32, or 36 hours.

In one embodiment, the step of reacting the lipids composition, alcohol and base may be conducted by refluxing the components to produce the fatty acid esters, such as PUFA esters. In additional embodiments, the step of reacting the lipids composition may be carried out at a temperature that does not result in the refluxing of the reaction components. For example, carrying out the step of reacting the lipids composition under pressures greater than atmospheric pressure can increase the boiling point of the solvents present in the reaction mixture. Under such conditions, the reaction can occur at a temperature at which the solvents would boil at atmospheric pressure, but would not result in the refluxing of the reaction components. In some embodiments, the reaction is conducted at a pressure from about 5 to about 20 pounds per square inch (psi); from about 7 to about 15 psi; or from about 9 to about 12 psi. In certain embodiments, the reaction is conducted at a pressure of 7, 8, 9, 10, 11, or 12 psi. Reactions conducted under pressure may be carried out at the reaction temperatures listed above. In some embodiments, reactions conducted under pressure may be carried out at a temperature of at least about 70° C., 75° C., 80° C., 85° C., or 90° C. In some embodiments, reactions conducted under pressure may be carried out at 70° C., 75° C., 80° C., 85° C., or 90° C.

In one embodiment of the present invention, fatty acid esters are separated from the reaction mixture by distilling the composition to recover a fraction comprising the ester of the fatty acid. A targeted fraction of the reaction mixture including the fatty acid esters of interest can be separated from the reaction mixture and recovered. In certain embodiments, the distillation is performed under vacuum. Without being bound by theory, distillation under vacuum allows the distillation to be accomplished at a lower temperature than in the absence of a vacuum and thus may prevent the degradation of the esters. Typical distillation temperatures range from about 120° C. to about 170° C. In some embodiments, the step of distilling is performed at a temperature of less than about 180° C., less than about 175° C., less than about 170° C., less than about 165° C., less than about 160° C., less than about 155° C., less than about 150° C., less than about 145° C., less than about 140° C., less than about 135° C., or less than about 130° C. Typical pressures for vacuum distillation range from about 0.1 mm Hg to about 10 mm Hg. In some embodiments, the pressure for vacuum distillation is at least about 0.1, 0.5, 1, 1.5, 2, 2.5, 3, 3.5, or 4 mm Hg. In some embodiments of the present invention, the pressure for vacuum distillation is about 0.1, 0.5, 1, 1.5, 2, 2.5, 3, 3.5, or 4 mmHg.

Renewable oils, waxes and fatty acids have significant demand in a wide range of industries (e.g. neutraceuticals, biolubricants, cosmetics, candles and soaps) and command a premium price compared to petroleum based products. High profit margins are usually expected for the lipid products, which can sell for greater than $2.00/pound, equating to $600 revenue per ton of feedstock (wheat straw costs $60/ton). Consumers will clearly benefit from this technology through the reduction of their dependence on petroleum-based products while generating a market for agricultural wastes and by-products. Since few companies and research groups are investigating fungal lipid production directly from lignocellulosic biomass for higher value products, both industry and the scientific community will benefit from the knowledge gained by this invention.

The renewable lipids are ideal for the increasing number of consumers demanding carbon-neutral, natural biobased products, which are currently produced primarily from limited plant and animal resources. The process of the invention offers an alternative to these renewable lipid sources and creates a market for waste agricultural feedstocks. The process of the invention is further developed for commercial production of lipid products from waste organic feedstocks. The process of the invention is optimized with a bench pilot-scale system, performing process flow design and techno-economic analysis of commercial production systems, analyzing lipid products in detail, and targeting appropriate markets/customers for the products. A pilot level demonstration system is designed to produce economically viable yields of high-value lipids from a variety of substrates for defined target markets and customers.

In another embodiment, the lipids extracted from the isolated fungal strain and/or its progeny of the present invention are used to produce biolubricants. As used herein, the term "biolubricants" refers to lubricants produced by using material originated from living or recently living organisms. As used herein, the term "lubricants" refers to substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509. One of the single largest applications for lubricants, in the form of motor oil, is to protect the internal combustion engines in motor vehicles and powered equipment. Typically lubricants contain 90% base oil (most often petroleum fractions, called mineral oils) and less than 10% additives. Vegetable oils or synthetic liquids such as hydrogenated polyolefins, esters, silicones, fluorocarbons and many others are sometimes used as base oils. These are primarily triglyceride esters derived from plants and animals. For lubricant base oil use the vegetable derived materials are preferred. Common ones include high oleic canola oil, castor oil, palm oil, sunflower seed oil and rapeseed oil from vegetable, and Tall oil from animal sources. Many vegetable oils are often hydrolyzed to yield the acids which are subsequently combined selectively to form specialist synthetic esters.

Additives deliver reduced friction and wear, increased viscosity, improved viscosity index, resistance to corrosion and oxidation, aging or contamination, etc. Lubricants such as 2-cycle oil are also added to some fuels. Sulfur impurities in fuels also provide some lubrication properties, which have to be taken in account when switching to a low-sulfur diesel; biodiesel is a popular diesel fuel additive providing additional lubricity. Non-liquid lubricants include grease, powders (dry graphite, PTFE, Molybdenum disulfide, tungsten disulfide, etc.), teflon tape used in plumbing, air cushion and others. Dry lubricants such as graphite, molybdenum disulfide and tungsten disulfide also offer lubrication at temperatures (up to 350° C.) higher than liquid and oil-based lubricants are able to operate. Limited interest has been shown in low friction properties of compacted oxide glaze layers formed at several hundred degrees Celsius in metallic sliding systems, however, practical use is still many years away due to their physically unstable nature. Another approach to reducing friction and wear is to use bearings such as ball bearings, roller bearings or air bearings, which in turn require internal lubrication themselves, or to use sound, in the case of acoustic lubrication. In addition to industrial applications, lubricants are used for many other purposes. Other uses include bio-medical applications (e.g. lubricants for artificial joints) and the use of personal lubricant for sexual purposes.

Thus, the lipids extracted from the culture of the isolated fungal strain and/or its progeny of the present invention can be used to produce ester-based biolubricant compositions, by adding suitable additives. Methods of making ester-based lubricant compositions are known to one skilled in the art. For a non-limiting example, a quantity of biologically-derived oil comprising triglycerides is provided and processed so as to hydrolyze at least some of the triglycerides and form free fatty acids, wherein the fatty acids are of a type selected from the group consisting of saturated fatty acids, monounsaturated fatty acids, and polyunsaturated fatty acids, and combinations thereof. The fatty acids are separated by type, such that at least the monounsaturated fatty acids are substantially isolated from the saturated fatty acids and the polyunsaturated fatty acids. Next, at least some of the monounsaturated fatty acids are modified to form an ester product (e.g., comprising triesters), and at least some of the saturated fatty acids and/or polyunsaturated fatty acids are hydrotreated to yield alkanes (paraffins). Note also that in some embodiments, such ester products can include one or more of the following: mono-, di-, and triester species, and hydroxylated analogues thereof.

Biohydrogen

The term biohydrogen here refers to hydrogen produced via biological processes, for example, via fermentation using the isolated fungal strain and/or its progeny of the present invention. The present invention provides methods of producing energy-rich metabolites using the isolated fungal strain and/or its progeny of the present invention, wherein the energy-rich metabolites are biogas, for example, hydrogen or methane. In one embodiment, hydrogen is produced under anaerobic conditions. In another embodiment, hydrogen is produced under substantially anaerobic conditions.

In one embodiment, feedstocks are mixed with the isolate fungal strain and/or its progeny of the present invention in a bioreactor to produce hydrogen. To accelerate degradation of feedstocks, vacuum can be used, for example, at about 0.1 atm, about 0.2 atm, about 0.3 atm, about 0.4 atm, about 0.5 atm, to remove gases including hydrogen out of the bioreactor. In one embodiment, production of other biogas, such as methane is inhibited to increase the production of hydrogen. Non-limiting examples systems and bioreactors of producing hydrogen are described in U.S. Pat. Nos. 7,473,552 and 7,083,956, which are hereby incorporated by reference in their entireties.

Biofuels from Sludge Materials

The isolated strain and/or its progeny of the present invention is tolerant to high concentration of metals and extreme pH conditions. Thus, the present invention provides methods for producing biofuel and/or precursors of biofuels using starting raw material, municipal, industrial, and/or farm sewage sludge or waste as carbon-containing feedstocks. The sludge may be treated municipal or industrial raw sludge or primary solids, or treated farm sludge. That is, the sludge in some embodiments has undergone one or more treatment processes such as anaerobic and/or aerobic digestion, composting, and/or at least one chemical or physical processing such as drying, dewatering, thickening, pressing, filtering, centrifugation, ultraviolet or chemical disinfection (e.g., chlorine disinfection), lime stabilization, and/or thermal processing.

In some embodiments, the sludge is a recalcitrant sludge having a high content of heavy metals such as one or more of Mn, Zn, Pb, Cu, Cr, Ni, Cd, and Hg. At least one, two, or three such heavy metal(s) (or heavy metals taken collectively) may be present at more than 10 ppm, or 50 ppm, or 100 ppm, or 200 ppm, or 400 ppm, or 500 ppm in the recalcitrant sludge, by weight. At least one such heavy metal (or heavy metals taken collectively) may be present at from about 400 to about 1000 ppm. For example, the recalcitrant sludge may be contaminated at such levels with lead (Pb) and/or cadmium (Cd). In one embodiment, said sludge or waste is acidic. In one embodiment, the pH of the sludge or waste ranges from about 0 to about 8, for example, from about 0.7 to about 7.5.

In another embodiment, said heavy metals in the sludge or waste are recovered through biosorption by the isolated fungal strain of the present invention, and said acidic sludge or waste is neutralized.

The isolated fungal strain and/or its progeny are also resistant to contaminations due to antibiotics produced inside (e.g., naphthazarin pigments). Thus, in these or other embodiments, the sludge has a high content of at least one bacterial, viral, and/or parasitic pathogen, including a variety of enteric pathogens, for example, enteropathogenic *E. coli, Salmonella, Shigella, Yersinia, Vibrio Cholerae, Cryptosporidium, Giardia, Entamoeba*, Norovirus, and Rotavirus, among others.

In certain embodiments, the sludge is generated by industrial activities. That is, the sludge is an end product of a waste water treatment plant of an industrial facility, such as a chemical, pharmaceutical, or paper production facility, or food processing facility.

The sludge may originate from a pharmaceutical production facility. In accordance with the invention, so long as the compounds produced by the pharmaceutical production facility are suitable feedstock for the isolated fungi strain, they can may be degraded by microbial metabolism and converted to biofuels.

The sludge may originate from a paper production facility. The pulp and paper industry is responsible for large discharges of highly polluted effluents. These pollutants, whose main characteristics are their high toxicity and low biodegradability, include a variety of tannins, lignins, resins, terpenes, and chlorophenolic compounds. The composition of these effluents, which has a great influence on its treatability, may vary considerably, depending on the raw material and manufacturing process. The present invention, however, provides methods and systems that are versatile with regard to synthesizing biofuel components from these toxic effluents.

In some embodiments, the sludge is generated by a food processing facility.

In some embodiments, the sludge is farm sludge comprising animal manure. Most animal manure is feces. Common forms of animal manure include FYM (farmyard manure) or farm slurry (liquid manure). Farmyard manure may also comprise plant material (often straw) which has been used as bedding for animals and has absorbed the feces and urine. Agricultural manure in liquid form is known as slurry, and is produced by more intensive livestock rearing systems where concrete or slats are used, instead of straw bedding.

Thus, the present invention provides methods of producing one or more energy-rich metabolites as biofuel or precursors of biofuel using one or more said isolated fungus stains as described above, comprising:
a) making a mixture of one or more said isolated fungal strains and/or its progeny with a feedstock material selected from the group consisting of ligno-cellulosic feedstocks, carbon containing waste products, carbohydrates, and a combination thereof in a container, wherein the material can support the growth of said isolated fungal strain and/or its progeny;
b) growing said isolated fungal strain in said mixture to produce one or more biofuels and/or precursors of biofuel; and
c) optionally, isolating said biofuels and/or precursors of biofuel from the mixture.

In one embodiment, additional compounds necessary for the growth of the isolated fungal strain and/or its progeny of the present invention are added into the mixture wherein the feedstocks do not contain, or contain insufficient mounts of said compounds necessary for the growth of the fungal strain. The isolated fungal strain and/or its progeny of the present invention can be used for biofuel and/or precursors of biofuel production from varies sources, such as ligno-cellulosic feedstocks, carbon containing waste products, carbohydrates, sugar monomers, or a combination thereof. In one embodiment, said biofuel is bioalcohol, biohydrogen, and/or biodiesel. In one embodiment, said precursors of biofuel are lipids or sugars. In one embodiment, said feedstocks are selected from the group consisting of ligno-cellulosic (e.g., algal mats, wheat straw, barley straw, corn stover, switch grass, spent brewing grains, forest products, energy crop material), carbohydrates (e.g., monosaccharides, disaccharides, oligosaccharides, polysaccharides), waste (e.g., municipal, industrial, and farm sewage sludge), and combination thereof.

The ligno-cellulosic feedstocks can be selected from the group consisting of agricultural crop residues (e.g., wheat straw, barley straw, rice straw, small grain straw, corn stover, corn fibers (e.g., corn fiber gum (CFG), distillers dried grains (DDG), corn gluten meal (CGM)), switch grass, hay-alfalfa, sugarcane bagasse), non-agricultural biomass (e.g., algal mats, urban tree residue), forest products and industry residues (e.g., softwood first/secondary mill residue, hard softwood first/secondary mill residue, recycled paper pulp sludge), ligno-cellulosic containing waste (e.g., newsprint, waste paper, brewing grains, used rubber tire (UTR), municipal organic waste, yard waste, clinical organic waste, waste generated during the production of biofuels (e.g. processed algal biomass, glycerol), and a combination thereof.

The carbon containing waste products can be selected from the group consisting of municipal organic waste, yard waste, industrial facility waste, such as waste from a chemical, pharmaceutical, or paper production facility, or food processing facility, and a combination thereof.

Carbohydrates feedstocks can be selected from the group consisting of monosaccharides, disaccharides, oligosaccharides, polysaccharides, and a combination thereof. In one embodiment, said sugar monomers are selected from the group consisting of trioses, tetroses, pentoses, hexoses, heptoses, et al., and a combination thereof. In one embodiment, said pentoses are selected from the group consisting of ribulose, xylulose, ribose, arabinose, xylose, lyxose, deoxyribose, and a combination thereof. In one embodiment, said hexoses are selected from the group consisting of allose, altrose, glucose, mannose, glucose, idose, galactose, talose, psicose, fructose, sorbose, tagatose, and a combination thereof.

In one embodiment, said mixture further comprises at least one component selected from the group consisting of acidification materials, manganese donors, and nutrient additions, pH buffering materials.

In one embodiment, said mixture has an initial pH 0.5 to 7.5 and will increase during fermentation unless in a buffered media or culture vessel with pH control from about 0 to about 8.0, for example, from about 0.5 to about 7.5, from about 0.5 to about 3.0 or from about 3.0 to about 7.0.

The methods of producing energy-rich metabolites using the isolated fungal strain and/or its progeny of the present invention have other advantages. For example, the present invention provides novel methods of producing energy-rich metabolites as biofuel or precursors of biofuel from feedstocks such as ligno-cellulosic materials (e.g., wood or straw). Currently existing methods of biofuel production from ligno-cellulosic materials require various expensive pretreatments and enzyme additions. One advantage of the present invention is that it does not require pretreatment steps of feedstocks, such as making the lignocellulosic material (e.g., wood or straw) amenable to hydrolysis, or cellulolysis, and enzymes additions, because the isolated fungal strain of the present invention itself can perform these steps. Thus, the process described here directly converts ligno-cellulosic feedstocks to energy-rich metabolites with few pretreatment steps and no enzyme additions. Consequently, use of this novel process is relatively simple and inexpensive in comparison to current methods. For another example, the isolated fungus of the present invention can be used to produce energy-rich metabolites as biofuel or precursors of biofuel over a wide pH range, thus, negating the need for costly pH neutralization steps. For another example, in the production of lipids as precursors of biodiesel, the isolated fungal strain of the present invention has a more favorable lipid profile in comparison to algae and other lipid producing organisms. For still another example, the isolated fungal strain and/or its progeny of the present invention is highly resistant to contamination by other organisms, since members of the *Fusarium* genus are known to generate naphthazarinoid pigments, which have potent antibiotic, insecticidal and phytotoxic properties (Brimble et al., 1999). Thus, the methods of producing energy-rich metabolites of the present invention do not require the use of costly and time consuming methods to prevent contamination as other currently microbial based production of biofuels. For still another example, the isolated fungal strain and/or its progeny of the present invention is tolerant to high concentration of metals, such as Mn, which can be used to increase lignin degradation rates.

Cultures and Compositions Comprising the Isolated Fungal Strain

*Fusarium oxysporum* strain MK7 is a new strain of acidophilic fungus, which can directly convert ligno-cellulosic feedstocks, carbohydrates (e.g., 5 and 6 carbon sugars), and biomass (e.g., algal biomass) to energy-rich substrates including lipids, ethanol and hydrogen.

The present invention provides a biologically pure culture having one, two, more or all of the identifying characteristics of the isolated fungal strain of *Fusarium oxysporum* and/or its progeny as described herein. In one embodiment, the biologically pure culture comprises the isolated fungal strain of *Fusarium oxysporum*, designated as MK7 which has been deposited as ATCC Accession Deposit No. PTA-10698, or active mutants thereof. In one embodiment, said isolated fungal strain and/or its progeny are in the form of conidia, pycnidia, chlamydospores, fragments of hyphae, or a combination thereof.

Applicant has made a deposit on behalf of National Park Service, Yellowstone National Park, USA on Mar. 2, 2010, of 25 vials of *Fusarium oxysporum* strain MK7 (as described herein) under the Budapest Treaty with the American Type Culture Collection (ATCC), P.O. Box 1549, Manassas, Va. 20108 USA, ATCC Accession No. PTA-10698. The strain was deposited prior to the filing date of this application. To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited *Fusarium oxysporum* strain MK7 (deposited as ATCC Accession Deposit No. PTA-10698):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and,
5. The deposit will be replaced if it should ever become unavailable.

The present invention further provides a composition comprising an isolated fungal strain of *Fusarium oxysporum* having at least one, two, more or all of the identifying characteristics as described herein. In one embodiment, said isolated fungal strain and/or its progeny are in the form of conidia, pycnidia, chlamydospores, fragments of hyphae, or a combination thereof. In some embodiments, the composition further comprises one or more components selected from the group consisting of a medium that supports growth of the fungal strain, an acidification material, a manganese donor, a nutrient addition, and a mixture thereof. In one embodiment, the medium is a solid. In another embodiment, the medium is a liquid.

In one embodiment, the composition comprises a medium supporting the growth of the isolated fungal strain and/or its progeny of the present invention. Suitable medium for isolating, growing, and maintaining *Fusarium oxysporum* are well known by those skilled in the art. Non-limiting examples of such media for *Fusarium oxysporum* are described in Gunner et al (1964, Anaerobic Growth of *Fusarium oxysporum*, *J. Bacteriol.* 87:1309-1316), Joshi et al (1987, The influence of various carbon and nitrogen sources on oil production by *Fusarium oxysporum*, 32(2): 124-129), De La Broise et al (1989, Osmotic, biomass, and oxygen effects on the growth rate of *Fusarium oxysporum* using a dissolved-oxygen-controlled turbidostat, *Biotechol. Bioeng.* 33(6):699-705), and Norio et al (2007, Selected media for *Fusarium oxysporum, Journal of General Plant Pathology,* 73(5):342-348; 2002, Selective medium for *Fusarium oxysporum* and nitrate metabolic capacity defective strain, *Kyushu Okinawa Nogyo Kenkyu Seika Joho,* 17:491-492), each of which is hereby incorporated by reference in its entirety.

The nutrition additions can be selected from the group consisting of carbohydrates (e.g., monosaccharides, polysaccharides), amino acids donor (e.g., amino acid, polypeptides), micronutrients (e.g., calcium, ammonium, copper, potassium, sodium, borax, ferrous, zinc, et al.), and combination thereof.

Acid pH Tolerant Enzymes from *F. oxysporum* Strain MK7

The current technology for ethanol production from lignocellulosic materials requires several steps prior to fermentation by yeast. These steps may include thermal degradation, dilute or concentrated acid hydrolysis, alkaline hydrolysis, or oxidation by chemicals such as hydrogen peroxide (Hendricks and Zeeman, 2009, Pretreatments to enhance the digestibility of lignocellulosic biomass. *Bioresource Technology,* 100:10-18.). The goal of pretreatment is to solubilize hemicellulose and lignin and decrystallize cellulose. However, before fermentation by yeast, the mixture must be pH neutralized and treated with enzymes to depolymerize cellulose into glucose.

The genome of *Fusarium oxysporum* f sp. *lycopersici* strain 4287 has recently been sequenced and has been shown to carry a variety of genes involved in the degradation of lignin, hemicellulose and cellulose. Furthermore, the enzymes involved in the degradation of these materials (e.g., cellulase, xylanase, ligninase, glucuronidase, arabinofuranosidase, arabinogalactanase, ferulic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase, xylosidase, α-L-arabinofuranosidase, feruloyl esterase, endoglucanase, β-glucosidase, Mn-peroxidase, and laccase) have been studied extensively in *F. oxysporum* strain F3 (Xiros et al. 2009, Enhanced ethanol production from brewer's spent grain by a *Fusarium oxyspo-*

*rum* consolidated system. *Biotechnol Biofuels.* 10:4). Consequently, *F. oxysporum* strains, including Strain MK7, are expected to be fully equipped to hydrolyze complex lignocellulosic materials such as wheat straw. It is also expected that since strain MK7 is capable of growth at much lower pH (0.7-7.5) in comparison to other *Fusarium* strains (pH>2; Starkey, 1973), the enzymes for lignin, hemicellulose and cellulose degradation in strain MK7 will have higher activities at low pH. Enzymes with high activity under acidic conditions would be especially useful for biofuel production when acid hydrolysis is used as a pretreatment for lignocellulosic materials.

Methods of cloning said enzymes are known in the art. For example, the gene encoding a specific enzyme can be isolated by RT-PCR from polyadenylated mRNA extracted from fungus, or by PCR from DNA extracted from fungus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode acid pH tolerant enzymes, including chimeric molecules, coned into an expression vector that can be expressed in a host cell other than *Fusarium oxysporum* (e.g., other fungus strain cell, a yeast cell, a bacteria cell, a plant cell, et al.). An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. The promoter can be a constitutive expression promoter, an inducible expression promoter, a tissue-specific expression promoter, or a sub-cellular organelle-specific expression promoter. In one embodiment, nucleotides encoding one or more acid pH tolerant enzymes are expressed in one expression vector transformed into a host cell, or more than one expression vectors co-transformed into the host cell.

In one embodiment, the acid pH tolerant enzymes purified from the isolated fungal strain and/or its progeny of the present invention, or produced in a recombinant host cell, when tested in vitro compared with a homologous enzyme from a non-acid tolerant *Fusarium oxysporum* strains (e.g., *Fusarium* strains that can only growth with a pH of at least 3.0, see Starkley et al., Effect of pH on toxcicity of copper to *Scytalidium* sp., a copper-tolerant fungus, and some other fungi. *J. gen. Microbiol.* 78: 217-225), has about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 400%, about 500%, about 550%, about 600%, about 650%, about 700%, about 800%, about 850%, about 900%, or about 1000% more activity under a pH of less than 3.0, less than 2.9, less than 2.8, less than 2.7, less than 2.6, less than 2.5, less than 2.4, less than 2.3, less than 2.2, less than 2.1, less than 2.0, less than 19, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, or less than 0.5.

Thus, the acid pH tolerant enzymes from *F. oxysporum* strain and/or its progeny of the present invention, and nucleotides encoding such enzymes can be isolated and utilized for many purposes. In one embodiment, such enzymes can be used in the pretreatment of ligno-cellulosic feedstocks for ethanol production prior to fermentation by other organisms (bacteria, fungi, yeasts, et al.) to degrade lignin, cellulose and hemicelluloses. For example, these enzymes are used right after hydrolysis of ligno-cellulosic feedstocks (esp. acid hydrolysis), wherein the lignin, cellulose and hemicelluloses are degraded by the enzymes. No neutralization step is required compared to conventional methods due to the acid tolerant property of the enzymes derived from the isolated fungal strain of the present invention. In one embodiment, the acid-tolerant enzymes produced by the isolated fungal strain of the present invention can be used for current biofuel production technologies that involve acid pretreatment and enzymatic degradation.

Toxins Produced by *F. oxysporum*

Currently, microbial based production of biofuels requires the use of costly and time consuming methods to prevent contamination. Strain MK7 is highly resistant to contamination by other organisms, because members of the *Fusarium* genus are known to generate toxins (e.g., naphthazarin pigments), which have potent antibiotic, insecticidal and phytotoxic properties. Thus, strain MK7 requires little or non external antibiotics to be added when used in the production of biofuel and/or biofuel precursors. *Fusarium oxysporum* in general produces nine different toxins, with production depending on their relationship with different host plants (Marasas et al., 1984, Toxigenic *Fusarium* species, identity and mycotoxicology, ISBN 0271003480). The production of toxins also varies with media used in vitro fermentation. The toxins produced and secreted by *Fusarium* species include, but are not limited to, bikaverin, enniatins, fusaric acid, lycomarasmin, moniliformin, oxysporone, trichothecenes, zearelones, various naphthoquinones and anthraquinones (e.g., nonaketide naphthazarin quinones, bikaverin and norbikaverin, heptaketides, nectriafurone, 5-O-methyljavanicin, and anhydrofusarubin lactol). For example, the toxins from *Fusarium* species may include, 4-Acetoxyscirpenediol (4-3-acetoxy-3,15-dihydroxy-12,13-epoxytrichothec-9-ene. A similar compound, monodeacetylanguidin=4- or 15-acetylscirpentriol), 3-Acetyldeoxynivalenol (Deoxynivalenol monoacetate, 3"-acetoxy-7",15-dihydroxy-12,13-epoxytrichothec-9-en-8-one), 8-Acetylneosolaniol (Neosolaniol monoacetate, 4",8",15-triacetoxy-3"-hydroxy-12,13-epoxytrichothec-9-ene), 4- or 15-Acetylscirpentriol (4-Acetoxyscirpenediol), Acetyl T-2 toxin (3",4",15-triacetoxy-8"-(3-methylbutyry(oxy)-12,13-epoxytricho-thec-9-ene), Anguidin (Diacetoxyscirpenol), Avenacein, Beauvericin, Butenolide (4-acetamido-4-hydroxy-2-butenoic-acid-lactone), Calonectrin (3",15-diacetoxy-12,13-epoxytrichothec-9-ene), 15-Deacetylcalonectrin (15-De-0-acetylcalonectrin, 3'-acetoxy-15-hydroxy-12,13-epoxytrichothec-9-ene), Deoxynivalenol (Rd toxin, Vomitoxin, 3",7",15-trihydroxy-12,13-epoxytricho-thec-9-en-8-one), Deoxynivalenol diacetate (Diacetyldeoxynivalenol), Deoxynivalenol monoacetate (3-Acetyldeoxynjvalenol), Diacetoxyscirpendiol (7"-Hydroxydiacetoxyscirpenol), Diacetoxyscirpenol (Anguidin, 4,15-diacetoxy-3'-hydroxy12,13-epoxytrjchothec-9-ene), Diacetoxyscerpentriol (7",8"-Dihydroxy-diacetoxyscirpenol), Diacetyldeoxynivalenol (Deoxynivalenol diacetate, 3",15-diacetoxy-7-hydroxy 12,13-epoxytrichothec-9-en-8-one), Diacetylnivalenol (Nivalenol diacetate, 4,15-diacetoxy-3',7'-dihydroxy-12,13-epoxytrichothec-9-en-8-one), 7",8"-Dihydroxydiacetoxyscirpenol (Diacetoxyscirpentriol, 4,15-diacetoxy-3",7",8"-trihydroxy-12,13-epoxytrichothec-9-ene), Enniatins, Fructigenin, Fumonisin $B_1$ (1,2,3-propanetricarboxylic acid 1,-1-[1-(12-amino-4,9,11-trihydroxy-2-methyltridecyl)-2-(1-methyl-pentyl)-1,2-ethanediyl]ester; macrofusine), Fusarenon (Fusarenon-X, Fusarenon, Monoacetylnivalenol, Nivalenol monoacetate, 4-acetoxy-3",7",15-trihydroxy-12,13-epoxytrichothec-9-en-8-one) Fusaric acid (Fusarinic acid, 5-butylpicolinic acid), Fusarinic acid (Fusaric acid), F-2 (Zearalenone), HT-2 toxin=15-acetoxy-3",4-dihydroxy-8"-(3-methylbutyryloxy)-12-epoxytricho-thec-9-ene. 7"-Hydroxydiacetoxyscirpenol (Diacetoxyscirpendiol, 4,15-diacetoxy-3",7"-dihydroxy-12,13-epoxytrichothec-9ene), 8"-Hydroxydiacetoxyscirpenol (Neosolaniol), 1,4-Ipomeadiol (1-(3-furyl)-1,4-pentanediol), Ipomeanine (1-(3-furyl)-1,4-pentanetione), 1-Ipomeanol (1-(3-furyl)-1-hydroxy-4-pentanone), 4-1pomeanol (1-(3-furyl)-4-hydroxy4pentanone), Lateritin, Lycomarasmin, Moniliformin (potassium or sodium salt of 1-hydroxycyclobut-1-ene-3,4-dione), Monoacetoxyscirpenol (15-acetoxy-3",4"-dihydroxy-12,13-epoxytrichothec-9ene), Monoacetylnivalenol (Fusarenon-X), Monodeacetylanguidin (4-Acetoxyscirpenediol), Neosolaniol (8"-Hydroxy-diacetoxyscirpenol, 4,15-diacetoxy-3"8"-dihydroxy-12,13-epoxytrichothec-9-ene), Neosolaniolacetate (8-Acetylneosolaniol), Neosolaniol monoacetate (8-Acetylneosolaniol), Nivalenol (3",4",7",15"-tetrahydroxy-12,13-epoxy-trichothec-9-en-8-one), Nivalenol diacetate (Diacetylnivalenol), Nivalenol monoacetate (Fusarenon-X), NT-1 toxin (T-1 toxin, 4",8"-diacetoxy-337,15-dihydroxy-12,13-epoxy-trichothec-9-ene), NT-2 toxin (4"oxy-3",8",15-trihydroxy-12,13-epoxytrichothec-9-ene), Rd toxin (Deoxynivalenol), Sambucynin, Scirpentriol (3",4",15"-trihydroxy-12,13-epoxytrichothec-9-ene), Solaniol (Neosolaniol), T-1 toxin (NT-1 toxin), T-2 toxin (4",15"-diacetoxy-3"-hydroxy-8"-(3-methylbutyrlyloxy)-12,13-epoxytrichothec-9-ene), Triacetoxy-scirpendiol (4",8",15"-triacetoxy-3",7"-dihydroxy-12,13-epoxytrichothec-9-ene), Triacetoxy-scirpenol 3", 4",15"-triacetoxy-12,13-epoxytrichothec-9-ene), Vomitoxin (Deoxynivalenol), Yavanicin, Zearalenol (2,4-dihydroxy-6-(6,10-dihydroxy-trans-1-undecenyl)-benzoic acid-lactone), Zearalenone (6-(10-hydroxy-6-oxo-trans-1-undecenyl)—resorcylic acid lactone). More detailed toxins produced by *F. oxysporum* are described in Tatum et al. (Naphthoquinones produced by *Fusarium oxysporum* isolated from citrus. 1985, *Phytochemistry* 24:457-459), Tatum et al. (Naphthofurans produced by *Fusarium oxysporum* isolated from citrus. 1987, Phytochemistry, 26:2499-2500), Baker et al. (Novel anthraquinones from stationary cultures of *Fusarium oxysporum*. 1998, *J Ferment Bioeng* 85:359-361). Thrane (*Fusarium* species on their specific profiles of secondary metabolites, in *Fusarium*. Mycotoxins, taxonomy and pathogenicity, 1989, ed by Chelkowski J, Elsevier, N.Y., USA, pp 199-225); Baker et al., Antimicrobial activity of naphthoquinones from *Fusaria*, Mycopathologia 111: 9-15, 1990; Marasas et al. (Toxigenic *Fusarium* species, identity and mycotoxicology, 1984, Pennsylvania State University Press, University Park, Pa., USA), each of which is incorporated by referent in its entirety for all purposes.

In another embodiment, the toxins (e.g., naphthazarin pigments) produced by strain MK7 may also be used for other industrial applications. For example, the toxins (e.g., naphthazarin pigments) produced by strain MK7 can be used as antibiotics, insecticides, and/or herbicides. In one embodiment, naphthazarin pigments produced by strain MK7 are applied together with a second chemical which is selected from other antibiotics, insecticides, and/or herbicides.

Siderophores Produced by *F. oxysporum*

*Fusarium oxysporum* strains are known to produce siderophores that may be utilized to complex metals for industrial applications. Siderophores produced by the isolated fungal strain of the present invention are expected to be functional at low pH.

Siderophores (Greek: "iron carrier") are small, high-affinity iron chelating compounds secreted by microorganisms such as bacteria, fungi and grasses (Neilands et al., A Crystalline Organo-iron Pigment from a Rust Fungus (*Ustilago sphaerogena*), 1952. *J. Am. Chem. Soc* 74: 4846-4847, Neilands et al., Siderophores: Structure and Function of Microbial Iron Transport Compounds. 1995, *J. Biol. Chem.* 270: 26723-26726). Siderophores are amongst the strongest soluble $Fe^{3+}$ binding agents known. Iron is essential for almost all life, essential for processes such as respiration and DNA synthesis. Despite being one of the most abundant elements in the Earth's crust, the bioavailability of iron in many environments such as the soil or sea is limited by the very low solubility of the $Fe^{3+}$ ion. Microbes release siderophores to scavenge iron from these mineral phases by formation of soluble $Fe^{3+}$ complexes that can be taken up by active transport mechanisms. Many siderophores are nonribosomal peptides (Miethke et al., 2007, Siderophore-Based Iron Acquisition and Pathogen Control. *Microbiol. Mol. Bio. Reviews.* 71: 413-451), although several are biosynthesized independently (Challis et al., 2005, A widely distributed bacterial pathway for siderophore biosynthesis independent of nonribosomal peptide synthetases. *Chem Bio Chem,* 6:601-611). Siderophores are amongst the strongest binders to $Fe^{3+}$ known, with enterobactin being one of the strongest of these. Because of this property, they have attracted interest from medical science in metal chelation therapy, with the siderophore desferrioxamine B gaining widespread use in treatments for iron poisoning and thalassemia. Siderophores also can chelate other metals, which include, but are not limited to, Aluminum, Gallium, Chromium, Copper, Zinc, Lead, Manganese, Cadmium, Vanadium, Indium, Plutonium, and Uranium.

Siderophores usually form a stable, hexadentate, octahedral complex with $Fe^{3+}$ preferentially compared to other naturally occurring abundant metal ions, although if there are less than six donor atoms water can also coordinate. The most effective siderophores are those that have three bidentate ligands per molecule, forming a hexadentate complex and causing a smaller entropic change than that caused by chelating a single ferric ion with separate ligands. For a representative collection of siderophores see Miller et al. (Studies and Syntheses of Siderophores, Microbial Iron Chelators, and Analogs as Potential Drug Delivery Agents. 2000, *Current Medicinal Chemistry* 7: 159-197). Siderophores are usually classified by the ligands used to chelate the ferric iron. The major groups of siderophores include the catecholates (phenolates), hydroxamates and carboxylates (e.g. derivatives of citric acid). Citric acid can also act as a siderophore. The wide variety of siderophores may be due to evolutionary pressures placed on microbes to produce structurally different siderophores which cannot be transported by other microbes' active transport systems, or in the case of pathogens deactivated by the host organism. Non-limiting examples of siderophores include, hydroxamate siderophores (e.g., ferrichrome in *Ustilago sphaerogena*, Desferrioxamine B (Deferoxamine) in *Streptomyces pilosus* or *Streptomyces coelicolor*, Desferrioxamine E in *Streptomyces coelicolor*, fusarinine C in *Fusarium roseum*, ornibactin in *Burkholderia cepacia*), catecholate siderophores (e.g., enterobactin in *Escherichia coli* and enteric bacteria, bacillibactin in *Bacillus subtilis* and *Bacillus anthracis*, vibriobactin in *Vibrio cholerae*), and mixed ligands siderophores (e.g., azotobactin in *Azotobacter vinelandii*, pyoverdine in *Pseudomonas aeruginosa*, yersiniabactin in *Yersinia pestis*). More fungal siderophores are described in Renshaw et al. (Fungal siderophores: structures, functions and applications, 2002, *Mycol. Res.* 106 (10): 1123-1142).

Siderophores have applications in medicine for iron and aluminum overload therapy and antibiotics for better targeting. Understanding the mechanistic pathways of siderophores has led to opportunities for designing small-molecule inhibitors that block siderophore biosynthesis and therefore bacterial growth and virulence in iron-limiting environments (Ferreras et al., 2005, Small-molecule inhibition of siderophore biosynthesis in *Mycobacterium tuberculosis* and *Yersinia pestis*. *Nature Chemical Biology* 1: 29-32). Siderophores are useful as drugs in facilitating iron mobilization in humans, especially in the treatment of iron diseases, due to their high affinity for iron. One potentially powerful application is to use the iron transport abilities of siderophores to carry drugs into cells by preparation of conjugates between siderophores and antimicrobial agents. Because microbes recognize and utilize only certain siderophores, such conjugates are anticipated to have selective antimicrobial activity.

Microbial iron transport (siderophore)-mediated drug delivery makes use of the recognition of siderophores as iron delivery agents in order to have the microbe assimilate siderophore conjugates with attached drugs. These drugs are lethal to the microbe and cause the microbe to commit suicide when it assimilates the siderophore conjugate. Through the addition of the iron-binding functional groups of siderophores into antibiotics, their potency has been greatly increased. This is due to the siderophore-mediated iron uptake system of the bacteria.

Thus, in one embodiment, siderophores can be extracted from the isolated *F. oxysporum* strain MK7. For example, the strain MK7 can be cultured using suitable medium as described in the present invention, or ligno-cellulosic feedstocks, carbon containing waste products, carbohydrates, or a combination thereof under anaerobic or aerobic conditions. Methods of extracting siderophores are known to one skilled in the art. Siderophore extraction into an organic solvent, ethyl acetate in the case of catechol type or either benzyl alcohol or chloroform:phenol (1:1) for the hydroxamate type, have been used as an effective purification steps for many type of siderophores since both salts and macromolecules are removed effectively (Neilands et al., Microbial iron compounds. 1981*, Ann. Rev. Biochem.* 50, 715-731). The polystyrene resin Amberlite XAD, for the purification of neutral, ferrichrome type of siderophores (Horowitz et al., Isolation and identification of the conidial growth factor of *Neurospora crassa.* 1976*, J. Bacteria* 127, 135-140.) and polyamide resin for chromatographic separation of catechol type have been widely used.

In addition, the present invention provides methods of detoxifying fluids containing metal ions and/or recovering metal ions from fluids by biosorption. In one embodiment, a composition comprising the isolated *F. oxysporum* strain MK7, or a composition comprising siderophores extracted from the isolated *F. oxysporum* strain MK7, can be used to detoxify fluids containing metals as described above and/or recover such metals. In one embodiment, a composition comprising sufficient amount of isolated *F. oxysporum* strain MK7 or siderophores extracted from the isolated *F. oxysporum* strain MK7 is mixed with a sample containing metals for a certain time which allows majority of the metal ions in the fluids bind to siderophores. In one embodiment, such a sample can be a waste fluid containing one or more types of metal ions (e.g., mining waste fluids, industrial waste fluids, et al.). In one example, the fluids contain at least one metal ion selected from the group consisting of Ag, Zn, Fe, Al, Be, Pb, Cu, Cr, Ni, Cd, Co, Ni, Mn, Pd, Pt, U, Th, Mo, Sn, Ti, As, Au and Hg. In one embodiment, the total initial metal ions concentration ranges from about 1 ppm to about 100,000 ppm, by weight. For example, the total metal ions concentration ranges from about 0.5 ppm (e.g. Cd) to about 250 ppm (e.g. Zn) depending on the metal constituent. In one embodiment, the waste fluids are mixed with isolated *F. oxysporum* strain MK7 in a bioreactor, wherein additional medium and nutrients for fungal growth are added into the bioreactor to allow proliferation of strain MK7. One of the most relevant requirements for the technological application of biosorption is the biomass fixation to an attaching medium in order to allow the biosorbent to be kept in a reactor, so it can be reused. This has been performed frequently by immobilizing the microorganisms on a matrix. Thus, in one embodiment, the strain MK7 or siderophore is immobilized on a matrix. There are many examples of the application of these methodologies, the most representative can be found in the following scientific researches: Brierley, Production and application of a *Bacillus*-based product for use in metals biosorption. In: B. Volesky, Editor, Biosorption of Heavy Metals, CRC Press, Boca Raton, Fla. (1990), pp. 305-312; Brierley, Immobilization of biomass for industrial application of biosorption. In: A. E. Torma, M. L. Apel and C. L. Brierley, Editors, Biohydrometallurgical Technologies, Proceedings of the International Biohydrometallurgy Symposium, The Minerals, Metals and Materials Society, Warrendale, Pa. (1993), pp. 35-44; Tsezos y Deutschmann (1990). An Investigation of Engineering Parameters for the use of Immobilized Biomass Particles in Biosorption. J. Chem. Technol. Biotechnol., 48, 29-39; Gilson y Thomas (1995), Calcium alginate bead manufacture: with and without immobilized yeast. Drop formation at a two-fluid nozzle. J. Chem. Technol. Biotechnol. 62 pp. 227-232; Bedell y Damall, (1990), Immobilization of nonviable, biosorbent, algal biomass for the recovery of metal ions. In: B. Volesky, Editor, Biosorption of Heavy Metals, CRC Press, Boca Raton, Fla., pp. 313-326; Figueira et al. (2000), Biosorption of metals in brown seaweed biomass. Water Res. 34 pp. 196-204; Kratochvil et al. (1997) Optimizing Cu removal/recovery in a biosorption column. Water Res. 31 pp. 2327-2339; Kratochvil y Volesky, (2000), Multicomponent biosorption in fixed beds. Water Res. 34 pp. 3186-3196; Trujillo et al, (1991), Mathematically modeling the removal of heavy metals from wastewater using immobilized biomass. Environ. Sci. Technol. 25 pp. 1559-1565. The immobilizing agents or the most commonly used matrixes are alginate, polyacrylamine, polysulfone, silica, cellulose and glutaraldehyde.

Metal ions that bind to biosorbent (strain MK7 or siderophores extracted from strain MK7) through biosorption step as described above are subjected desorption step which allows to elute the metal ions from the siderophores and regenerate the metals binding capacity of the fungal strain or extracted siderophores. This is performed by treating the mixture of fungal strain and waste fluids or the mixture of extracted siderophores and waste fluids with an acid solution and, subsequently, with a base solution to neutralize the acid in the mixture. The acid (e.g., concentrated $H_2SO_4$ 95-97%) solution is added into to the mixture for desorption, wherein the metal ions are released from the immobilized biosorbent (strain MK7 or siderophores extracted from strain MK7). After the desorption step, the mixture is neutralized by using a base solution (e.g., a concentrated sodium hydroxide solution (e.g. NaOH 50%).

Plasticizer

The inventors also discovered that the present isolated *F. oxysporum* strain can produce plasticizers, e.g., Diisooctyl phthalate (DIOP) and Hexanedioic acid, mono(2-ethylhexyl)ester (a.k.a. 2-Ethylhexyl hydrogen adipate).

Plasticizers (dispersants) are additives that increase the plasticity or fluidity of the material to which they are added; these include plastics, cement, concrete, wallboard, and clay. Although the same compounds are often used for both plastics and concretes the desired effect is slightly different. The worldwide market for plasticizers in 2004 had a total volume of around 5.5 million tons, which led to a turnover of just over 6 billion pounds.

Plasticizers for concrete soften the mix before it hardens, increasing its workability or reducing water, and are usually not intended to affect the properties of the final product after it hardens. Plasticizers for wallboard increase fluidity of the mix, allowing lower use of water and thus reducing energy to dry the board. The plasticizers for plastics soften the final product increasing its flexibility.

Plasticizers for plastics are additives, most commonly phthalates, that give hard plastics like PVC the desired flexibility and durability. They are often based on esters of polycarboxylic acids with linear or branched aliphatic alcohols of moderate chain length. Plasticizers work by embedding themselves between the chains of polymers, spacing them apart (increasing the "free volume"), and thus significantly lowering the glass transition temperature for the plastic and making it softer. For plastics such as PVC, the more plasticizer added, the lower its cold flex temperature will be. This means that it will be more flexible, though its strength and hardness will decrease as a result of it.

Ester plasticizers serve as plasticizers, softeners, extenders, and lubricants, esters play a significant role in rubber manufacturing. The basic function of an ester plasticizer is to modify a polymer or resin enhancing its utility. Ester plasticizers make it possible to achieve improved compound processing characteristics, while also providing flexibility in the end-use product. Ester plasticizers are selected based upon cost-performance evaluation. The rubber compounder must evaluate ester plasticizers for compatibility, processibility, permanence and other performance properties. The wide varieties of ester chemistries that are in production include sebacates, adipates, gluterates, phthalates, azelates, and other specialty blends. This broad product line provides an array of performance benefits required for the many elastomer applications such as tubing and hose products, seals and gaskets, belts, wire and cable and print rolls. Low to high polarity esters provide utility in a wide range of elastomers including nitrile, polychloroprene, EPDM, chlorinated polyethylene, and epichlorohydrin. Plasticizer-elastomer interaction is governed by many factors such as solubility parameter, molecular weight and chemical structure. Compatibility and performance attributes are key factors in developing a rubber formulation for a particular application.

None-limiting examples of plasticizers include, phthalate-based plasticizers (e.g., Bis(2-ethylhexyl) phthalate (DEHP), Diisononyl phthalate (DINP), Bis(n-butyl)phthalate (DnBP, DBP), Butyl benzyl phthalate (BBzP), Diisodecyl phthalate (DIDP), Di-n-octyl phthalate (DOP or DnOP), Diisooctyl phthalate (DIOP), Diethyl phthalate (DEP), Diisobutyl phthalate (DIBP), and Di-n-hexyl phthalate), Trimellitates (e.g., Trimethyl trimellitate (TMTM), Tri-(2-ethylhexyl) trimellitate (TEHTM-MG), Tri-(n-octyl, n-decyl) trimellitate (ATM), Tri-(heptyl,nonyl) trimellitate (LTM), n-octyl trimellitate (OTM)), Adipate-based plasticizers (Bis(2-ethylhexyl)adipate (DEHA), Dimethyl adipate (DMAD), Monomethyl adipate (MMAD), Dioctyl adipate (DOA)), Dibutyl sebacate (DBS), Dibutyl maleate (DBM), Diisobutyl maleate (DIBM), benzoates, epoxidized vegetable oils, sulfonamides, N-ethyl toluene sulfonamide (o/p ETSA), ortho and para isomers, N-(2-hydroxypropyl) benzene sulfonamide (HP BSA), N-(n-butyl) benzene sulfonamide (BBSA-NBBS), Organophosphates (e.g., Tricresyl phosphate (TCP), Tributyl phosphate (TBP), Glycols/polyethers, Triethylene glycol dihexanoate (3G6, 3GH), Tetraethylene glycol diheptanoate (4G7)), polymeric plasticizers, and polybutene.

As a plasticizer, DIOP is an all-purpose plasticizer for polyvinyl chloride, polyvinyl acetate, rubbers, cellulose plastics, and polyurethane.

The present invention is further illustrated by the following examples that should not be construed as limiting. The contents of all references, patents, and published patent applications cited throughout this application, as well as the Figures, are incorporated herein by reference in their entirety for all purposes.

EXAMPLE

Example 1

Isolation and Growth of *Fusarium oxysporum* Strain MK7

The isolated fungal *Fusarium oxysporum* strain MK7 of the present invention was isolated from Yellowstone National Park under NPS-permitted project study number YELL-2007-SCI-1976.

Methods of isolating *Fusarium oxysporum* strain MK7 were previously described. For example, 0.5 grams of algae-fungal biomass was inoculated in 200 mL of native filtered spring water from Yellowstone National park at pH 2.5 and cultured in sunlight for 10 days, after which the algae were consumed. 50 uL of the remaining pinkish biomass was streaked onto 1.2% agar with synthetic media (Kozubal et al., 2008) at pH 3.0.

The isolated fungus was studied and confirmed to be a *Fusarium oxysporum* strain by morphological characteristics, which include hyphae that are septate and hyaline, short and unbranched conidiophores; abundant and typical *Fusarium oxysporum*-like sickle-shaped macroconidia with 5-septate measuring approximately 25-50×3-4.5 μm; and abundant slightly curved non-septate microconidia about 5-10×2.0-3.5 μm. In addition, BLAST results of 18S rRNA and ITS (internal transcribed spacer) region DNA sequences (SEQ ID NO. 1) indicate that the organism is a *Fusarium oxysporum* strain.

During growth of strain MK7, enzymes were produced that degrade lignin, cellulose and hemicelluloses. The fungus utilizes the resultant degradation products to generate lipids or produce ethanol and hydrogen, depending on the conditions.

```
SEQ ID NO. 1
18S rRNA and ITS region DNA sequence of
Fusarium oxysporum strain MK7
CCGCGGGGAATACTACCTGATCCGAGGTCACATTCAGAGTTGGGGGTTTA

CGGCTTGGCCGCGCCGCGTACCAGTTGCGAGGGTTTTACTACTACGCAAT

GGAAGCTGCAGCGAGACCGCCACTAGATTTCGGGGCCGGCTTGCCGCAAG

GGCTCGCCGATCCCCAACACCAAACCCGGGGGCTTGAGGGTTGAAATGAC

GCTCGAACAGGCATGCCCGCCAGAATACTGGCGGGCGCAATGTGCGTTCA

AAGATTCGATGATTCACTGAATTCTGCAATTCACATTACTTATCGCATTT

TGCTGCGTTCTTCATCGATGCCAGAACCAAGAGATCCGTTGTTGAAAGTT

TTGATTTATTTATGGTTTTACTCAGAAGTTACATATAGAAACAGAGTTTA

GGGGTCCTCTGGCGGGCCGTCCCGTTTTACCGGGAGCGGGCTGATCCGCC

GAGGCAACAATTGGTATGTTCACAGGGGTTTGGGAGTTGTAAACTCGGTA

ATGATCCCTCCGCAGTTCTCACCTACGGATAGGATCATTACCGAGTTTAC

AACTCCCAAACCCCTGTGAACATACCCATTGTTGCCTCGGCCGGATCAGC

CCGCTCCCGGTTAAAACGGGACGGCCCGCCAGAGTACCCCTAAACTCTGT

TTCTATATGTAACTTCTGAGTAAAACCATAAATAAATCAAAACTTTCAAC

ACGCATCTCTTGCTTCTGTCATCGATGAAGAACGCAGCAAAATGCGATAG

TCATGTGATTGCACATTCAGTGAATCATCGATCTTGACGCACATTGCGCC

TGCAGTATTCTGGCGGTCATGCCTGTTCGAGCGTCATTCAGCCCTCAGCC

CTCGGTTGTGTTCGGGATCGGCGAGTCCTGCGCCAGCGACCGGATCAGTG

GCGTCTGCCTGCGCCTCCATTGCGGTTAGAGTTAAGCCCTCGCCCACTTG

TTTTACGCTAAC
```

Example 2

Lipids Production by *Fusarium oxysporum* Strain MK7

Figure 2:
FIG. 2 depicts fungal biomass after 7 d of growth on wheat straw at pH 2.5 under aerobic conditions. This fungal mat is ready for lipid extraction.

*Fusarium oxysporum* strain MK7 inoculum and liquid media (containing Ammonium nitrate 3.5 g/liter, Calcium chloride-2-$H_2O$ 0.4 g/liter, Magnesium sulphate-7-$H_2O$ 0.30 g/liter, Potassium phosphate mono basic 2 g/liter, Manganese sulfate 0.5 g/liter, and trace minerals to final concentrations described by Kozubal et al., 2008, incorporated herein by reference in its entirety) can be mixed with ligno-cellosic feedstocks, ligno-cellulosic feedstocks, carbon containing waste products or sugar monomers in an aerobic system. After a given number of days, the organism can be harvested and used for lipid extraction. The proprietary process may also be conducted in an anaerobic system in which ethanol and hydrogen gas are produced. FIG. 2 shows fungal biomass of *Fusarium oxysporum* strain MK7 after 7 days of growth on wheat straw at pH 2.5 under aerobic conditions. The fungal mat was ready for lipid extraction.

In a test, different types of feedstocks were mixed with *Fusarium oxysporum* strain MK7 inoculum and liquid media, including glucose, xylose, alfalfa, avicel, white paper, and wheat straw. After 10 days, fungus biomass was harvested for lipid extraction. Lipids in the fungus biomass were extracted using the 2:1 chloroform/methanol total lipid extraction method described previously (Bligh and Dyer, A rapid method of total lipid extraction and purification. 1959, *Can. J. Biochem. Physiol.*, 37, 911-917).

Figure 3:
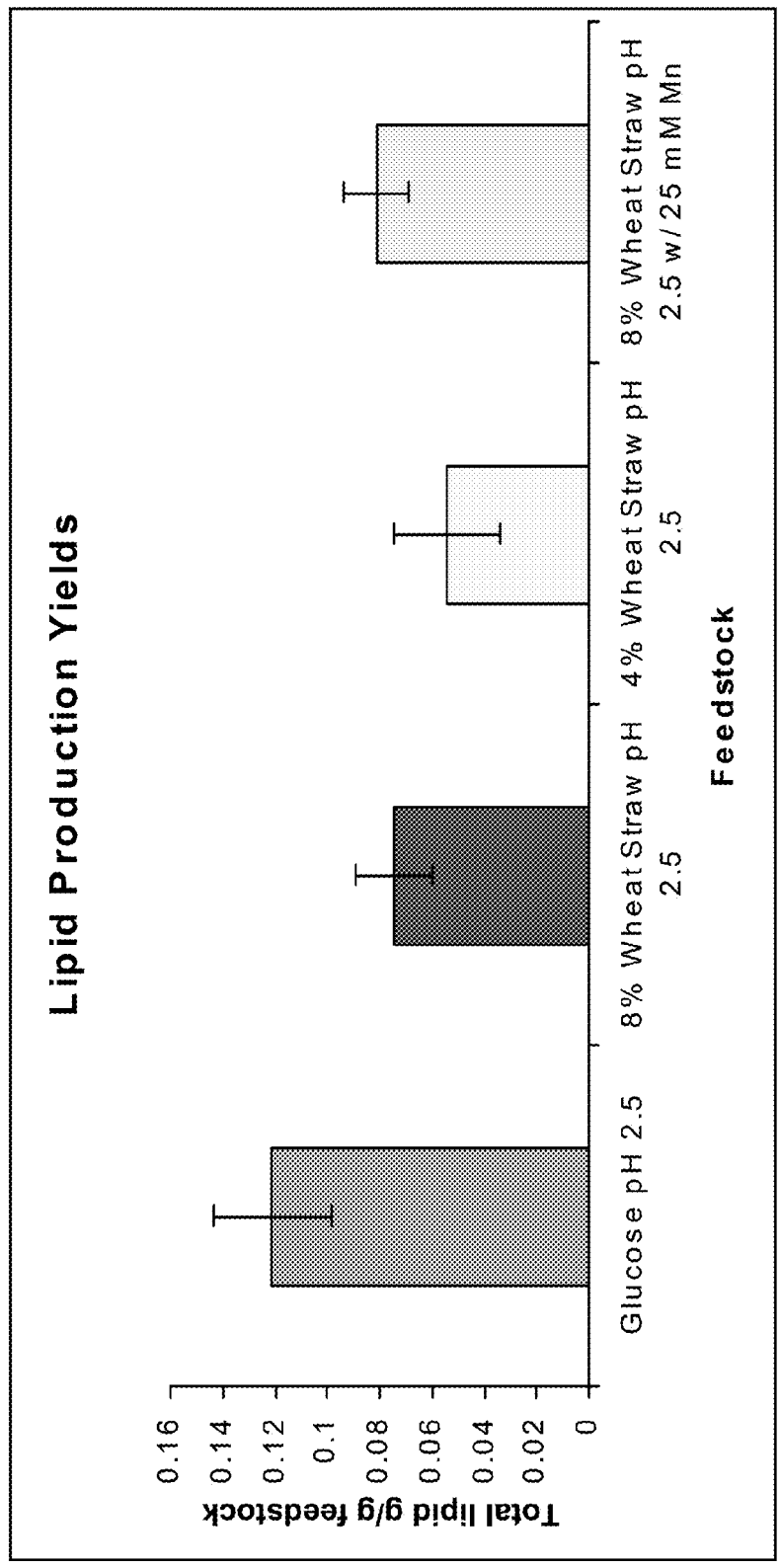
FIG. 3 depicts total lipid production by *Fusarium* strain MK7 and/or its progeny as a fraction of initial glucose or wheat straw. Wheat straw percentage (4% or 8%) indicates initial mass of wheat straw to volume of water. Error bars show standard deviations of three experiments.
Figure 4:
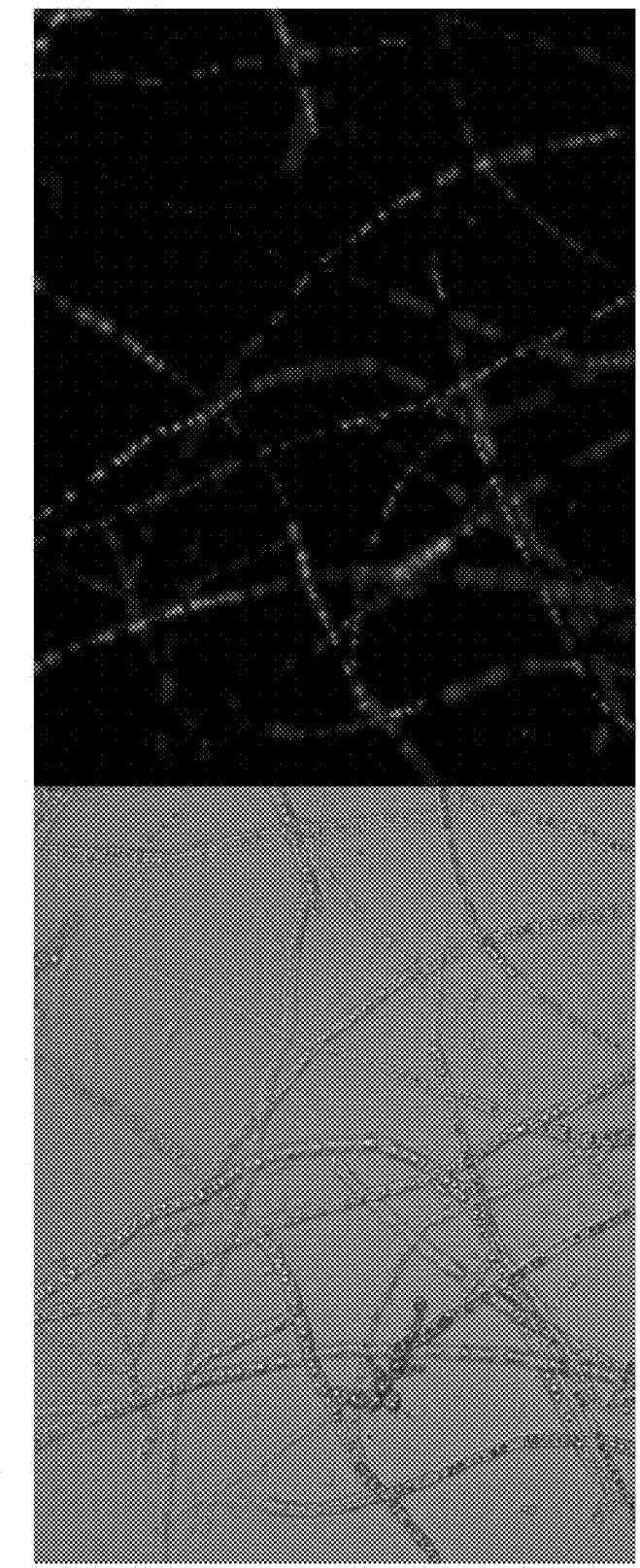
FIG. 4 depicts optical microscopy (left) of *Fusarium* strain MK7 and/or its progeny cultured on wheat straw at pH 2.5 after 10 days. Identical view obtained using fluorescent microscopy of Nile Red stained cells (right) clearly reveal significant lipid production (Nile Red specifically stains lipids, Cooksey et al., 1987).

Total yield of extracted lipids from strain MK7 growing in each different feedstock was determined using gravimetric analytical procedure. The yields of fungus growing glucose (pH 2.5), 8% wheat straw (pH 2.5), 4% wheat straw (pH 2.5), and 8% wheat straw (pH 2.5; 25 mM Mn) are displayed in FIG. 3. As it shows, strain MK7 can produce lipids from glucose or wheat straw, and almost 8% of the initial mass of wheat straw was converted to lipid after 10 days at pH 2.5. Optical and fluorescent microscopy revealed the accumulation of large lipid globules within the cells of strain MK7 (FIG. 4).

Figure 5:
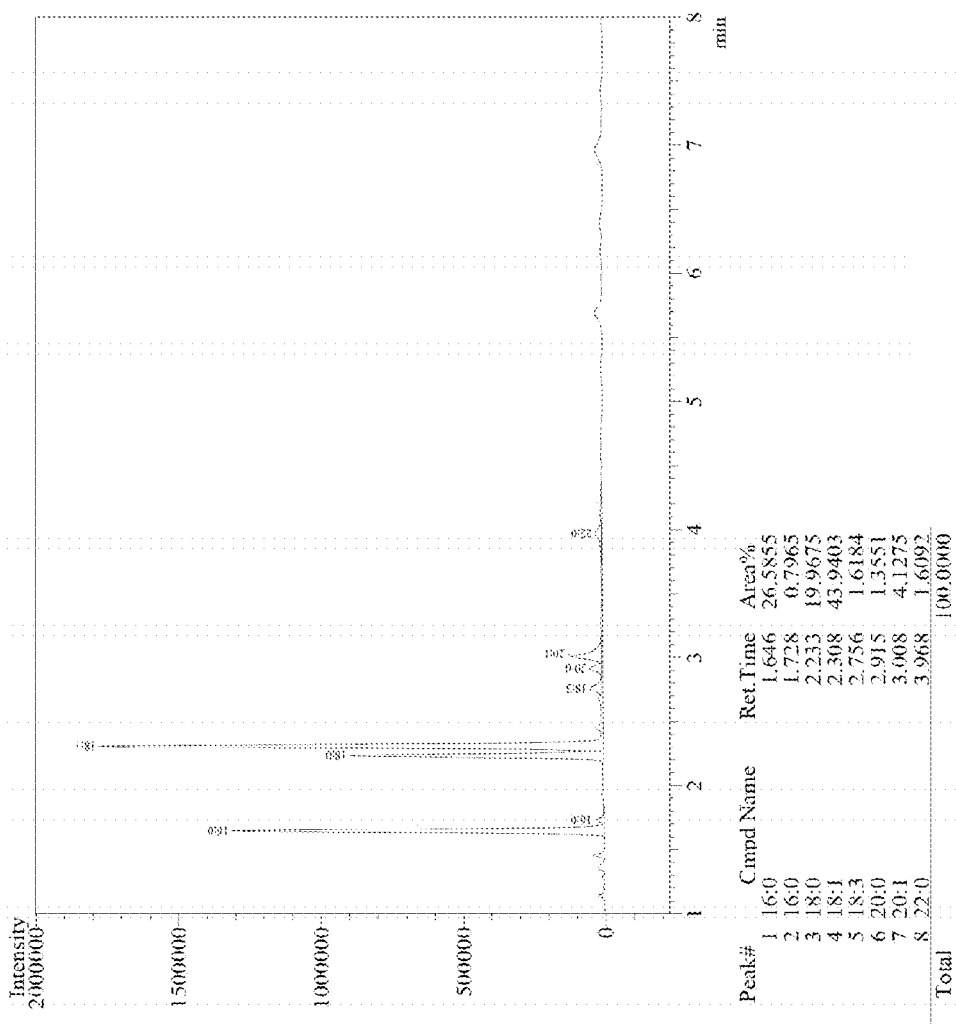
FIG. 5 depicts fatty acid profile for *Fusarium* strain MK7 and/or its progeny cultured on wheat straw at pH 2.5 after 10 days.

The fatty acid composition of lipids extracted from cultures grown on wheat straw at pH 2.5 was determined using gas chromatography. The results showed that approximately 44% of the total lipid content was comprised of acid oleic acid (18:1), a mono-unsaturated fatty acid, and about 46% palmitic (16:0) and stearic acids (18:0), which are saturated fatty acids (FIG. 5). A high concentration of mono-unsaturated fatty acids such as oleic acid is desirable for production of biodiesel due to their favorable viscosity and reduced problems with oxidation (Pinzi et al., 2009. The Ideal Vegetable Oil-based Biodiesel Composition: a Review of Social, Economical and Technical Implications. *Energy Fuels*, 23(5):2325-2341). In this regard, the lipid profile generated by *Fusarium* strain MK7 is more favorable in comparison to that of other described fungi (Ya et al. 2008, Lipids of Filamentous Fungi as a Material for Producing Biodiesel Fuel. *Applied Biochemistry and Microbiology*. 44:523-527; Meng et al., 2009, Biodiesel production from oleaginous microorganisms. *Renewable Energy*. 34: 1-5) and microalgae, which produce much higher proportions of polyunsaturated fatty acids that are prone to oxidation (Christi, Biodiesl from microalgae. 2007, *Biotechnology Advances*. 25:294-306).

Example 3

Ethanol Production by *Fusarium oxysporum* Strain MK7

*Fusarium* strain MK7 is capable of producing significant amounts of ethanol under anaerobic and microaerobic conditions using five and six carbon sugars. Additionally, it is capable of directly converting acid-pretreated wheat straw to ethanol.

Figure 6:
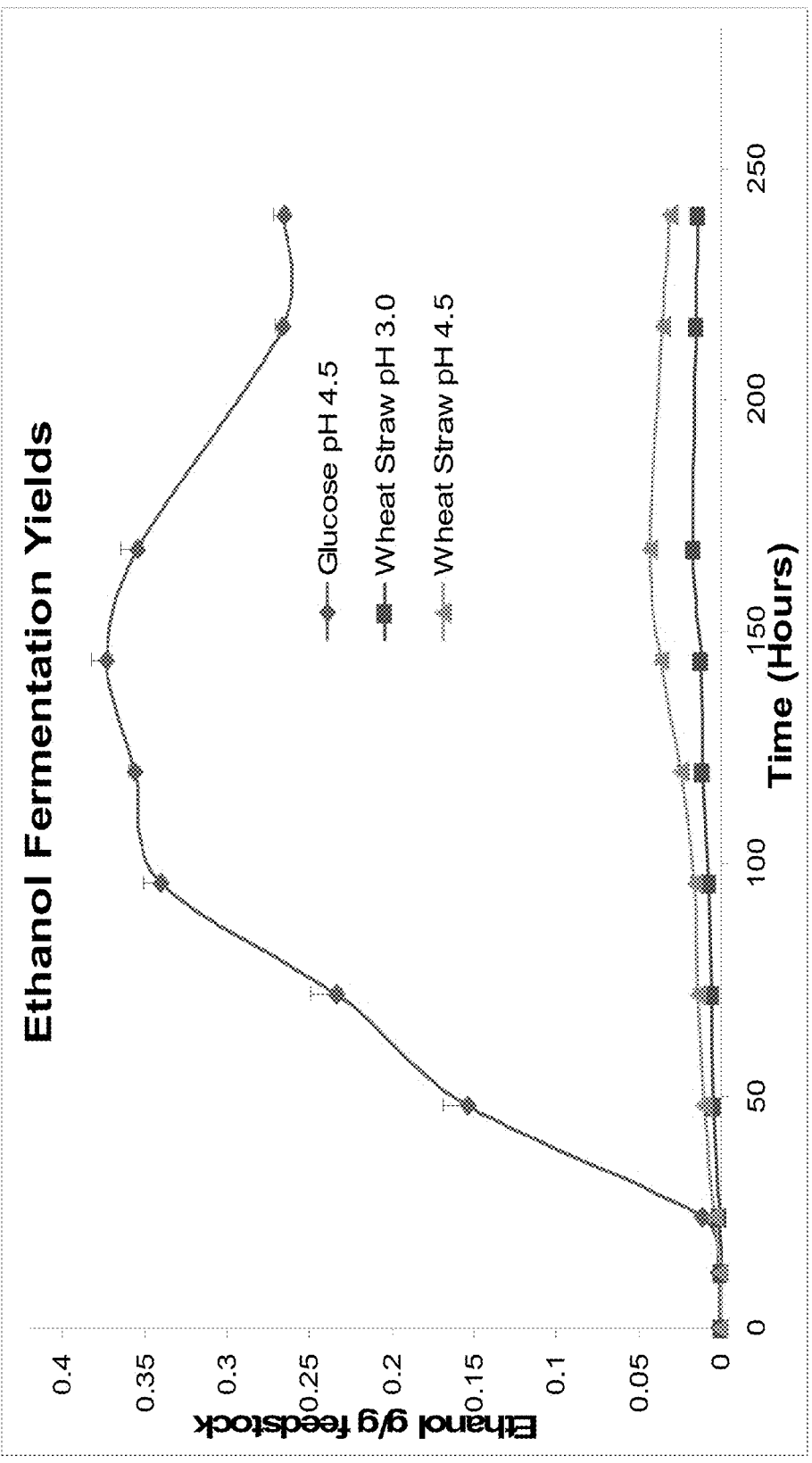
FIG. 6 depicts ethanol yields in grams of ethanol produced per gram of dry wheat straw feedstock or glucose.

FIG. 6 summarizes ethanol yields for 4% glucose (w/v) at pH 4.5 and 4% wheat straw (w/v) at pH 3 and 4.5 grown under anaerobic conditions in sealed serum bottles. The ethanol yields on glucose were similar to those found for other *Fusarium* species grown on glucose (Ruiz et al., 2007. Sugar fermentation by *Fusarium oxysporum* to produce ethanol. *World J Microbiol Biotechnol*. 23:259-267), and pH neutralized sugars derived from wheat straw, sweet sorghum stalk and spent brewers grain hydrolysates after alkali pretreatment (Christakopoulos et al., 1991, Direct Ethanol Conversion of Pretreated Straw by *Fusarium oxysporum*. *Bioresource Technology*. 35: 297-300; Christakopoulos et al., 1993, Direct conversion of sorghum carbohydrates to ethanol by a mixed microbial culture. *Bioresource Technology*, 45: 89-92; Lezinou et al., 1994, Simultaneous saccharification and fermentation of sweet sorghum carbohydrates to ethanol in a fed-batch process. *Biotechnology Letters*. 16:983-988; and Xiros et al., 2009, Enhanced ethanol production from brewer's spent grain by a *Fusarium oxysporum* consolidated system. *Biotechnol Biofuels*. 10:4). Ethanol yields at pH 2.5 using wheat straw as a feedstock were low for strain MK7, corresponding to results for other fungal and yeast species grown at pH 4.5-5.5 (Christakopoulos et al., 1989, Direct fermentation of cellulose to ethanol by *Fusarium oxysporum*. *Enzyme Microb Tech.* 11:236-239; Christakopoulos et al., 1991, Direct Ethanol Conversion of Pretreated Straw by *Fusarium oxysporum*. *Bioresource Technology.* 35: 297-300). This is likely due to the inhibition of ethanol fermentation by phenolics, furfurals and other compounds that are produced during acid hydrolysis (Palmqvist and Hahn-Hagerdal, 2000).

Example 4

Hydrogen Production by *Fusarium oxysporum* Strain MK7

In addition to the production of ethanol during fermentation, strain MK7 produces hydrogen gas when grown anaerobically in sealed serum bottles using ligno-cellulosic feedstocks. Although no hydrogen was produced during glucose fermentation, concentrations as high as 4% $H_2$ gas were measured in the gas headspace when wheat straw was used as a growth substrate. The presence of a hyd3-like hydrogenase gene sequence, likely important for $H_2$ production, was confirmed in Strain MK7 using polymerase chain reaction.

Example 5

Biofuel or Biofuel Precursors Production by *Fusarium oxysporum* Strain MK7 with Pretreatments Various pretreatments may be utilized to enhance conversion rates by strain MK7 in the production of biofuel or biofuel precursors. Pretreatments may include acidification to less than pH 3.0, Mn addition, and nutrient addition (e.g. ammonium and phosphate).

Previous work has shown that Mn(III) likely increases the degradation of lignin through the oxidization of lignin phenolic groups coupled with the reduction of Mn(III) to Mn(II) (Kerem and Hadar, 1995, Effect of manganese on preferential degradation of lignin by *Pleurotus ostreatus* during solid-state fermentation. *Appl Environ Microbiol.* 61(8): 3057-3062; Boominathan et al., 1992, cAMP-mediated differential regulation of lignin peroxidase and manganese-dependent peroxi-dase production in the white-rot basidiomycete *Phanerochaete chrysosporium*. Proc. Natl. Acad. Sci. 89:5586-5590; Tebo et al., 1997, Bacterially-mediated mineral formation: Insights into manganese(II) oxidation from molecular genetic and biochemical studies. In: J. F. Banfield and K. H. Nealson (Eds.) Geomicrobiology: Interactions Between Microbes and Minerals. Reviews in Mineralogy. 35:225-266). Oxidation of Mn(II) to Mn(III) by a variety of enzymes can regenerate Mn(III).

Experiments with strain MK7 indicated that the fungus can tolerate very high levels of Mn and that Mn concentrations of 5, 10 and 25 mM increased wheat straw degradation and fungal growth. Accurate biomass quantification has not yet been completed but visual estimates indicated an increase in fungal biomass of approximately 10-25%. Lipid production appears to be enhanced as well.

Strain MK7 also tolerates very acidic pH conditions. To increase the conversion rates by strain MK7 in the production of biofuel or biofuel precursors using ligno-cellulosic feedstocks, acidification materials are added into the mixture of strain MK7 inoculum and ligno-cellulosic feedstocks, wherein the pH of the mixture is less than 3.0, less than 2.9, less than 2.8, less than 2.7, less than 2.6, less than 2.5, less than 2.4, less than 2.3, less than 2.2, less than 2.1, less than 2.0, less than 19, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, or less than 0.5. A mixture of strain MK7 inoculum and ligno-cellulosic feedstocks with a pH of 7.0 is included as a control. After incubation for a proper time, the biofuel or the biofuel precursors are extracted from fungal biomass and/or the mixture of fugal biomass and feedstocks. Compared to the control mixture, the acidified mixture of strain MK7 inoculum and ligno-cellulosic feedstocks produce about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 400%, about 500%, about 550%, about 600%, about 650%, about 700%, about 800%, about 850%, about 900%, or about 1000% more biofuel or biofuel precursors.

Example 6

Enzymes and Antibiotics Production by *Fusarium oxysporum* Strain MK7

Enzymes (e.g., cellulase, xylanase, ligninase, glucuronidase, arabinofuranosidase, arabinogalactanase, ferulic acid esterase, lipase, pectinase, glucomannase, amylase, laminarinase, xyloglucanase, galactanase, glucoamylase, pectate lyase, chitinase, exo-β-D-glucosaminidase, cellobiose dehydrogenase, and acetylxylan esterase, xylosidase, α-L-arabinofuranosidase, feruloyl esterase, endoglucanase, β-glucosidase, Mn-peroxidase, and laccase) in *Fusarium oxysporum* strain MK7 are potentially acid pH tolerant. The enzymes, and the nucleotides encoding the enzymes, are very useful in biotechnology, and thus can be isolated.

To isolate acid tolerant enzymes from *F. oxysporum* strain MK7, traditional molecular cloning procedures can be applied. For example, the gene encoding a specific enzyme can be isolated by RT-PCR from polyadenylated mRNA extracted from fungus, or by PCR from DNA extracted from fungus. Primers specific for a gene encoding an enzyme of interest are designed based on the genome information of *Fusarium oxysporum*, or peptide sequence of a purified enzyme from *Fusarium oxysporum* MK7, or peptide sequence of homologous enzymes from *Fusarium* species. The resulting product gene can be cloned as a DNA insert into a vector. The vector can be an expression vector suitable for a host cell (e.g., a fungal cell, a bacteria cell, a yeast cell, a plant cell, an insect cell, or an animal cell).

The acid pH tolerant enzymes purified from *Fusarium oxysporum* MK7, or produced in a recombinant host cell, when tested in vitro compared with a homologous enzyme from a non-acid tolerant *Fusarium oxysporum* species, has about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 400%, about 500%, about 550%, about 600%, about 650%, about 700%, about 800%, about 850%, about 900%, or about 1000% more activity under a pH of less than 3.0, less than 2.9, less than 2.8, less than 2.7, less than 2.6, less than 2.5, less than 2.4, less than 2.3, less than 2.2, less than 2.1, less than 2.0, less than 19, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, or less than 0.5.

Example 7

Lipid Profiles Produced by Strain MK7

Figure 7:
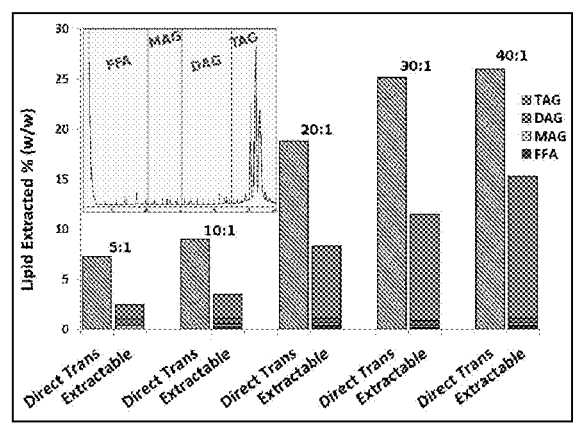
FIG. 7 depicts lipid profiles produced by strain MK7.
Figure 7:
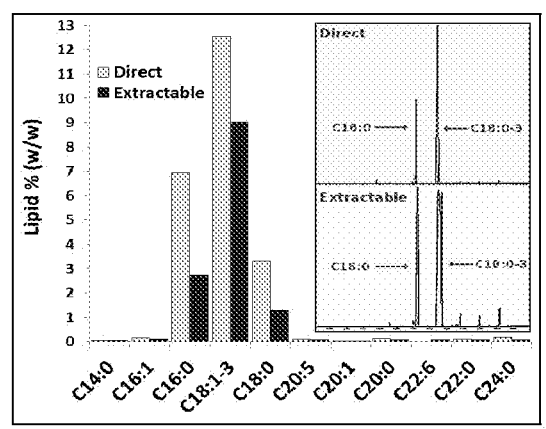

The production of total intracellular lipids was determined using direct transesterification coupled with GC-MS analysis as described in Lohman et al. (2013). Strain MK7 lipid profiles were remarkably consistent among treatments (i.e. pH, temperature, growth substrate, cultivation duration, moisture content) and were dominated by C16:0 and C18:0, C18:1 and C18:2 triacylglycerides (>95% of total lipids, FIG. 7B). Total fuel potential and extractable lipid fractions show profiles ideal for biodiesel (FIG. 7A). Fatty acid profiles also show a number of high value products including the omega-7 vaccenic acid (Methyl 11-octadecenoate), omega-7 palmitoleic acid (methyl hexadec-9-enoate; trade name Provinal™) and tetracosanoic acid, methyl ester (Table 1). These are rare fatty acids not typically found in vegetable oils and may produce significantly more revenue per ton of feedstock than biodiesel alone.

TABLE 1

Identities, concentrations and prices for lab grade purity compounds identified by GC-MS. The listed percentage of total lipid for each compound was produced by strain MK7.

| Name | Formula | % Total Lipid | Average Price - lab grade ($/g) |
|---|---|---|---|
| Methyl tetradecanoate | $C_{15}H_{30}O_2$ | 0.28 | 23 |
| Methyl hexadec-9-enoate (omega-7 palmitoleic acid 16:1) | $C_{17}H_{32}O_2$ | 0.71 | 394 |
| Hexadecanoic acid, methyl ester (palmitic acid 16:0) | $C_{17}H_{34}O_2$ | 29.3 | 30 |
| C18:1-3 (combination of oleic; linoleic acid; conjugated linoleics and linolenic acid) | $C_{19}H_{34}O_2$ | 50.14 | 25-900 |
| Methyl 11-octadecenoate (omega-7 vaccenic acid; 18:1) | $C_{19}H_{36}O_2$ | 2.92 | 945 |
| Octadecanoic acid, methyl ester (stearic 18:0) | $C_{19}H_{38}O_2$ | 14.03 | 24 |
| Eicosanoic acid, methyl ester | $C_{21}H_{42}O_2$ | 0.59 | 271 |
| Docosanoic acid, methyl ester | $C_{23}H_{46}O_2$ | 0.43 | 71 |
| Tetracosanoic acid, methyl ester | $C_{25}H_{50}O_2$ | 0.76 | 340 |

FIG. 7A shows the average of total fatty acid methyl esters (FAME) in direct transesterfication (total fuel potential) and extractable lipid fractions as a function of media C:N ratio (n=3). Bars within the extractable lipid fraction bar represent tri-, di- and mono-acyl glycerides (TAG, DAG, MAG) and free fatty acids (FFA) components. Inset shows a GC-FID chromatogram with TAG molecules dominating the lipid fraction. FIG. 7B shows FAME profile of lipids generated from direct transesterification of all fatty acids (Direct) to FAME, and FAME derived from only extractable lipid precursors (Extractable). Inset shows GC-MS chromatograms for the Direct and Extractable fractions.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Abe T., Hoshino T., Nakamura A., and N. Takaya. 2007. Anaerobic elemental sulfur reduction by fungus *Fusarium oxysporum*. Biosci Biotechnol Biochem. 71:2402-7.

Bligh, E. G. and Dyer, W. J. 1959. A rapid method for total lipid extraction and purification. Can. J. Biochem. Physiol. 37:911-917.

Bhatia, I. S., Arneja J. S. Lipid metabolism in *Fusarium oxysporum*, Journal of the Science of Food and Agriculture, 2006, 29(7):619-626.

Boominathan, K., Reddy, C. A. 1992. cAMP-mediated dierential regulation of lignin peroxidase and manganese-dependent peroxi-dase production in the white-rot basidiomycete *Phanerochaete chrysosporium*. Proc. Natl. Acad. Sci. 89:5586-5590.

Briggs, Michael. UNH Biodiesel Group. 2004. "Wide scale Biodiesel Production from Algae". http://www.unh.edu/p2/biodiesel/article_alge.html.

Brimble M. A., Letecia J. Duncalfband Michael R. Nairn. 1999. Pyranonaphthoquinone antibiotics-isolation, structure and biological activity. Nat. Prod. Rep. 16:267-281

Chisti, Y. 2007. Biodiesel from microalgae. Biotechnology Advances. 25: 294-306

Christakopoulos P, Macris B J, Kekos D. 1989. Direct fermentation of cellulose to ethanol by *Fusarium oxysporum*. Enzyme Microb Tech. 11:236-239.

Christakopoulos P., D. P. Koullas, D. Kekos, E. G. Koukios and B. J. Macris. 1991. Direct Ethanol Conversion of Pretreated Straw by *Fusarium oxysporum*. Bioresource Technology. 35: 297-300

Christakopoulos P., LIAN-WU L., KEKOS D., MACRIS B. J. 1993. Direct conversion of sorghum carbohydrates to ethanol by a mixed microbial culture. Bioresource Technology, 45: 89-92, Cooksey, K. E., J. B. Guckert, S. A. Williams, and P. R. Calli. 1987. Fluorometric determination of the neutral lipid content of microalgal cells using Nile Red". Journal of Microbiological Methods, 6: 333-345.

Davière J. M., Langin T., and M. J. Daboussi. 2001. Potential role of transposable elements in the rapid reorganization of the *Fusarium oxysporum* genome. Fungal Genet Biol. 34:177-92.

Gross S., and E. I. Robbins. 2000, Chemistry and Ecology of Highly Acidic Environments. Acidophilic and acid-tolerant fungi and yeasts Hydrobiologia 433: 91-109.

Hua-Van A., Davière J. M., Kaper F., Langin T., and M. J. Daboussi. 2000. Genome organization in *Fusarium oxysporum*: clusters of class II transposons. Curr Genet. 37:339-47.

Inskeep W. P., G. G. Ackerman, W. P. Taylor, M. Kozubal, S. Korf, and R. E. Macur. 2005. On the energetics of chemolithotrophy in nonequilibrium systems: case studies of geothermal springs in Yellowstone National Park. Geobiology. 3: 297-320.

Kerstetter J. D. and J. K. Lyons. 2001. Wheat straw for ethanol production in Washington: a resource, technical and economic assessment, Washington State University, Cooperative Extension Energy Program.

Kozubal M., Macur R. E., Korf S., Taylor W. P., Ackerman G. G., Nagy A., and W. P. Inskeep. 2008. Isolation and Distribution of a Novel Iron-Oxidizing Crenarchaeon from Acidic Geothermal Springs in Yellowstone National Park. Appl. Environ. Microbiol. 74: 942-949.

Lezinou V., Christakopoulos P., Kekos D., Macris B. J. 1994. Simultaneous saccharification and fermentation of sweet sorghum carbohydrates to ethanol in a fed-batch process. Biotechnology Letters. 16:983-988.

Li Q., Du W, Liu D. 2008. Perspectives of microbial oils for biodiesel production. Appl Microbiol Biotechnol. 80:749-56.

Kerem Z. and Y. Hadar. 1995. Effect of manganese on preferential degradation of lignin by *Pleurotus ostreatus* during solid-state fermentation. Appl Environ Microbiol. 61(8): 3057-3062.

Meng X., Yang J., Xu X., Zhang L., Nie Q., and M. Xian. 2009. Biodiesel production from oleaginous microorganisms. Renewable Energy. 34: 1-5.

Naim N. Saad R. R., Naim M., 1985, Production of lipids and sterols by *Fusarium oxysporum* (Schlecht). Utilization of some agro-industrial by-products as additives and basal medium, Agricultural Wastes 14(3):207-220

Naqvi B. S., Hashmi K, Farooq A. K., Dilnawaz S., and A. M. Zafar. 1997. Production of Lipids by fermentation Preliminary Report. Journal of Islamic Academy of Sciences. 10:13-18.

Palmqvist E., and Barbel Hahn-Hagerdal. 2000. Fermentation of lignocellulosic hydrolysates. II: inhibitors and mechanisms of inhibition. Bioresource Technology 74: 25-33

Panagiotoua G., P. Christakopoulosb, L. Olssona. 2005. Simultaneous saccharification and fermentation of cellulose by *Fusarium oxysporum* F3—growth characteristics and metabolite profiling. Enzyme and Microbial Technology 36: 693-699

Patrick, C., Hallenbeck and Dipankar Ghosh. 2009. Advances in fermentative biohydrogen production: the way forward? Trends in Biotechnology. In Press.

Pinzi S., I. L. Garcia, F. J. Lopez-Gimenez, M. D. Luque de Castro, G. Dorado and M. P. Dorado. 2009. The Ideal Vegetable Oil-based Biodiesel Composition: A Review of Social, Economical and Technical Implications. Energy Fuels Ruiz E., I. Romero M. Moya S. Sanchez V. Bravo E. Castro. 2007. Sugar fermentation by *Fusarium oxysporum* to produce ethanol. World J Microbiol Biotechnol. 23:259-267

Seo H., Kim H., Lee O., Ha J., Lee H., and K. Jung. 2009. Measurement of ethanol concentration using solvent extraction and dichromate oxidation and its application to bioethanol production process. Journal of Industrial Microbiology and Biotechnology. 36: 285-292.

Seraphim P., Michael K., A. George. 2004. Single cell oil (SCO) production by *Mortierella isabellina* grown on high-sugar content media. Bioresour Technol. 95:287-91.

Smith S. N. 2007. An Overview of Ecological and Habitat Aspects in the Genus *Fusarium* with Special Emphasis on the Soil-Borne Pathogenic Forms Plant Pathology Bulletin. 16: 97-120, Starkey, R. L. 1973. Effect of pH on tocicity of copper to *Scytalidium* sp., a copper-tolerant fungus, and some other fungi. J. gen. Microbiol. 78: 217-225.

Tebo, B. M., W. C. Ghiorse, L. G. van Waasbergen, P. L. Siering, and R. Caspi. 1997. Bacterially-mediated mineral formation: Insights into manganese(II) oxidation from molecular genetic and biochemical studies. In: J. F. Banfield and K. H. Nealson (Eds.) Geomicrobiology: Interactions Between Microbes and Minerals. Reviews in Mineralogy. 35:225-266.

White J. S., Yohannan B. K., Walker G. M. 2008. Bioconversion of brewer's spent grains to bioethanol. FEMS Yeast Res. 8(7):1175-84. Epub 2008 Jun. 10.

Xiros, C., and P. Christakopoulos. 2009. Enhanced ethanol production from brewer's spent grain by a *Fusarium oxysporum* consolidated system. Biotechnol Biofuels. 10:4.

Xiros C., Topakas E, Katapodis P, Christakopoulos P. 2008. Evaluation of *Fusarium oxysporum* as an enzyme factory for the hydrolysis of brewer's spent grain with improved biodegradability for ethanol production. Ind Crops Prod. 28:213-224.

Ya. E. Sergeeva, L. A. Galanina, D. A. Andrianova, and E. P. Feofilova. 2008. Lipids of Filamentous Fungi as a Material for Producing Biodiesel Fuel. Applied Biochemistry and Microbiology. 44:523-527.

---

The invention claimed is:

1. A method of producing an energy-rich substrate, said method comprising contacting a carbon source with isolated *Fusarium oxysporum* strain MK7 (ATCC Accession Deposit No. PTA-10698) to form a mixture, incubating said mixture at pH 1.0-4.5 for a period of time under aerobic conditions, and obtaining the energy-rich substrate following such contact, wherein the energy-rich substrate is a total lipid fraction comprising at least 95% C16:0, C18:0, C18:1, and C18:2 triacylglycerides.

2. The method of claim 1, wherein the carbon source is a cellulosic biomass product.

3. The method of claim 1, wherein the carbon source is a lignocellulosic feedstock or lignocellulosic waste.

4. The method of claim 1, wherein the carbon source is a carbohydrate.

5. The method of claim 4, wherein the carbohydrate is selected from the group consisting of glucose, dextrose, maltose, sucrose, monosaccharides, polysaccharides, oligosaccharides, and starch.

6. The method of claim 1, wherein the *Fusarium oxysporum* strain and the carbon source are incubated in microaerobic conditions.

7. The method of claim 1, comprising a pretreatment step, wherein said pretreatment step is selected from the group consisting of: reducing the pH of the carbon source and *Fusarium oxysporum* mixture, adding manganese to the carbon source and *Fusarium oxysporum* mixture and adding a nutrient to the carbon source and *Fusarium oxysporum* mixture before the incubation step.

8. The method of claim 1, wherein the pH is 2.5.

9. The method of claim 1, wherein about 44% of the total lipid content comprises oleic acid (18:1).

10. The method of claim 1, wherein the energy-rich substrate further comprises a total lipid content of about 46% palmitic (16:0) and stearic (18:0) acids.

11. The method of claim 1, wherein the C16:0 triglyceride comprises at least hexadecanoic acid, methyl ester.

12. The method of claim 1, wherein the C16:0 triglyceride comprises about 29% palmitic acid.

13. The method of claim 1, wherein the total lipid fraction further comprises about 50% C18:1-3 triglycerides.

14. The method of claim 13, wherein the C18:1-3 triglycerides comprise a combination of oleic acid, linoleic acid, conjugated linoleic acids, and linolenic acid.

15. The method of claim 1, wherein the energy-rich substrate further comprises at least one fatty acid methyl ester selected from the group consisting of methyl tetradecanoate; methyl hexadec-9-enoate; hexadecanoic acid, methyl ester; oleic acid; linoleic acid; conjugated linoleics; linolenic acid; methyl 11-octadecenoate; octadecanoic acid, methyl ester; eicosanoic acid, methyl ester; docosanoic acid, methyl ester; and tetracosanoic acid, methyl ester.

16. The method of claim 15, wherein the energy-rich substrate further comprises at least one fatty acid selected from the group consisting of methyl tetradecanoate; eicosanoic acid, methyl ester; docosanoid acid, methyl ester; and tetracosanoic acid, methyl ester.

17. The method of claim 1, further comprising extracting lipids from the energy-rich substrate.

18. The method of claim 17, wherein the incubation time is at about 10 days and the total yield in grams of the extracted lipids is about 5% of the initial mass in grams of the carbon source.

19. The method of claim 18, wherein the total yield in grams of the extracted lipids is about 12% of the initial mass in grams of the carbon source.

20. The method of claim 1, wherein the total lipid fraction produced is about 0.05 g/g feedstock.

* * * * *

UNITED STATES PATENT AND TRADEMARK OFFICE
CERTIFICATE OF CORRECTION

PATENT NO. : 9,796,989 B2  
APPLICATION NO. : 14/790948  
DATED : October 24, 2017  
INVENTOR(S) : Mark A. Kozubal et al.

Page 1 of 1

It is certified that error appears in the above-identified patent and that said Letters Patent is hereby corrected as shown below:

In the Claims

At Column 64, Claim 16, Line number 41, should read:
-- The method of claim 15, wherein the energy-rich substrate further comprises at least one fatty acid selected from the group consisting of methyl tetradecanoate; eicosanoic acid, methyl ester; docosanoic acid, methyl ester; and tetracosanoic acid, methyl ester. --

At Column 64, Claim 18, Line number 48, should read:
-- The method of claim 1, wherein the incubation time is about 10 days and the total yield in grams of the extracted lipids is about 12% of the initial mass in grams of the carbon source. --

At Column 64, Claim 19, Line number 52, should read:
-- The method of claim 18, wherein the total yield in grams of the extracted lipids is about 5% of the initial mass in grams of the carbon source. --

Signed and Sealed this  
Tenth Day of April, 2018

Andrei Iancu  
*Director of the United States Patent and Trademark Office*